(12) United States Patent
Becker et al.

(10) Patent No.: US 12,187,844 B2
(45) Date of Patent: Jan. 7, 2025

(54) BLOCK COPOLYMERS OF LACTONES AND POLY(PROPYLENE FUMARATE)

(71) Applicant: THE UNIVERSITY OF AKRON, Akron, OH (US)

(72) Inventors: Matthew Becker, Stow, OH (US); James Wilson, Wolverhampton (GB); Shannon Petersen, Youngwood, PA (US)

(73) Assignee: The University of Akron, Akron, OH (US)

( * ) Notice: Subject to any disclaimer, the term of this patent is extended or adjusted under 35 U.S.C. 154(b) by 436 days.

(21) Appl. No.: 16/483,208

(22) PCT Filed: Mar. 20, 2018

(86) PCT No.: PCT/IB2018/051867
§ 371 (c)(1),
(2) Date: Aug. 2, 2019

(87) PCT Pub. No.: WO2018/142384
PCT Pub. Date: Aug. 9, 2018

(65) Prior Publication Data
US 2020/0231760 A1 Jul. 23, 2020

Related U.S. Application Data

(60) Provisional application No. 62/561,722, filed on Sep. 22, 2017, provisional application No. 62/541,889, filed on Aug. 7, 2017, provisional application No. 62/509,340, filed on May 22, 2017, provisional application No. 62/500,777, filed on May 3, 2017, provisional application No. 62/453,724, filed on Feb. 2, 2017, provisional application No. 62/453,786, filed on Feb. 2, 2017.

(51) Int. Cl.

| | |
|---|---|
| C08G 63/52 | (2006.01) |
| B33Y 70/00 | (2020.01) |
| C08G 63/08 | (2006.01) |
| C08G 63/682 | (2006.01) |
| C08G 63/685 | (2006.01) |
| C08G 63/82 | (2006.01) |
| C08G 63/91 | (2006.01) |
| C08G 65/332 | (2006.01) |
| C08G 81/02 | (2006.01) |
| C08L 63/10 | (2006.01) |
| A61L 27/18 | (2006.01) |
| B33Y 80/00 | (2015.01) |

(52) U.S. Cl.
CPC .............. *C08G 63/52* (2013.01); *B33Y 70/00* (2014.12); *C08G 63/08* (2013.01); *C08G 63/682* (2013.01); *C08G 63/6858* (2013.01); *C08G 63/823* (2013.01); *C08G 63/918* (2013.01); *C08G 65/3322* (2013.01); *C08G 81/027* (2013.01); *C08L 63/10* (2013.01); *A61L 27/18* (2013.01); *B33Y 80/00* (2014.12)

(58) Field of Classification Search
CPC .......... C08L 67/06; C08L 63/10; B33Y 70/00; B33Y 80/00; C08G 63/08; C08G 63/52; C08G 63/682; C08G 63/6858; C08G 63/688; C08G 63/823; C08G 63/83; C08G 63/91; C08G 63/918; C08G 65/3322; C08G 81/027
See application file for complete search history.

(56) References Cited

U.S. PATENT DOCUMENTS

| | | |
|---|---|---|
| 3,538,043 A | 11/1970 | Herold |
| 6,124,373 A | 9/2000 | Peter et al. |
| 6,306,821 B1 | 10/2001 | Mikos et al. |
| 6,652,835 B1 | 11/2003 | Lauffer et al. |

(Continued)

FOREIGN PATENT DOCUMENTS

| | | |
|---|---|---|
| WO | 95/29710 A1 | 11/1995 |
| WO | 2006/055940 A2 | 5/2006 |
| WO | 2016/081587 A1 | 5/2016 |

OTHER PUBLICATIONS

Adam L. Sisson et "The contemporary role of .s-caprolactone chemistry to create advanced polymer architectures", Polymer 54 (2013) 4333-4350 (Year: 2013).*

(Continued)

*Primary Examiner* — Frances Tischler
*Assistant Examiner* — Gennadiy Mesh
(74) *Attorney, Agent, or Firm* — Renner, Kenner, Greive, Bobak, Taylor & Weber Co., LPA

(57) ABSTRACT

In various embodiments, the present invention provides well-defined biodegradable poly(lactone-b-propylene fumarate) diblock and triblock polymers formed using a novel one-pot, scalable ring-opening block-order copolymerization (ROBOCOP) technique that utilizes magnesium 2,6-di-tert-butyl-4-methylphenoxide (Mg(BHT)$_2$(THF)$_2$) to "switch" from the ROP of cyclic esters to the ROCOP of maleic anhydride (MAn) and propylene oxide (PO) to produce PPF based block copolymers for application in additive manufacturing and patient specific regenerative medicine. These block copolymers are fully resorbable and can be photochemically crosslinked in a number of applications, including 3D printing. By adding the lactone block to the PPF polymer, the viscosity of the resulting block copolymer at working temperatures can be precisely controlled and the quantity of the reactive diluent in printable resins can be reduced or eliminated.

17 Claims, 24 Drawing Sheets

(56) References Cited

U.S. PATENT DOCUMENTS

| | | | |
|---|---|---|---|
| 7,649,022 | B2 | 1/2010 | Gomurashvili et al. |
| 8,445,007 | B2 | 5/2013 | Gomurashvili et al. |
| 8,652,504 | B2 | 2/2014 | Li et al. |
| 8,765,164 | B2 | 7/2014 | Katsarava et al. |
| 8,809,212 | B1 | 8/2014 | Dirk et al. |
| 8,974,815 | B2 | 3/2015 | Chu et al. |
| 2008/0004368 | A1 | 1/2008 | Wang et al. |
| 2008/0138317 | A1 | 6/2008 | Fung |
| 2010/0094338 | A1 | 4/2010 | Stopek et al. |
| 2014/0256596 | A1 | 9/2014 | Tite et al. |

OTHER PUBLICATIONS

Raphae Riva et al "Combination of Ring-Opening Polymerization and "Click Chemistry": Toward Functionalization and Grafting of Poly(e-caprolactone)", Macromolecules 2007, 40, 796-803 (Year: 2007).*

Licheng Tan et al "Antimicrobial Hydantoin-grafted Poly(e-caprolactone) by Ring-opening Polymerization and Click Chemistry", Macromol. Biosci. 2012, 12, 1721-1730 (Year: 2012).*

Shyeni Paul et al "Ring-opening copolymerization (ROCOP): synthesis and properties of polyesters and polycarbonates", Chem. Commun., 2015, 51, 6459-6479 (Year: 2015).*

Shanfeng Wang et al "Synthesis and characterizations of biodegradable and crosslinkable poly( 8-caprolactone fumarate ), poly(ethylene glycol fumarate ), and their amphiphilic copolymer", Biomateria Is 27 (2006) 832 841 (Year: 2006).*

E. Martin et al ""In Situ" Formation of Yttrium Alkoxides: A Versatile and Efficient Catalyst for the ROP of Caprolactone", Macromolecules 2003, 36, 5934-5941 (Year: 2003).*

W.Yao et al "Efficient ring-opening polymerization of c:-caprolactone using anilido-iminealuminum complexes in the presence of benzyl alcohol", Polymer 49 (2008) 2486-2491 (Year: 2008).*

International Search Report and Written Opinion of the International Searching Authority in PCT/IB2018/051867 mailed Apr. 6, 2018.

Shung A.K. et al., "Kinetics of poly(propylene fumarate) synthesis by step polymerization of diethyl fumarate and propylene glycol using zinc chloride as a catalyst," Journal of Biomaterials Science. Polymer Edition vol. 13, No. 1, p. 95 (2002).

Angela M. DiCiccio and Geoffrey W. Coates, "Ring-Opening Copolymerization of Maleic Anhydride with Epoxides: A Chain-Growth Approach to Unsaturated Polyesters," J. Am. Chem. Soc. 201, 133, 10724-10727.

Shigenobu Takenouchi, Akinori Takasu, Yoshihito Inai, and Tadamichi Hirabayashi, "Effects of Geometrical Difference of Unsaturated Aliphatic Polyesters on Their Biodegradability II. Isomerization of Poly(maleic anhydride-co-propylene oxide) in the Presence of Morpholine," Polymer Journal, vol. 34, No. 1, pp. 36-42 (2002).

Sobczak, M., "Ring-opening polymerization of cyclic esters in the presence of choline/SnOct2 catalytic system," Polym. Bull. (2012) 68:2219-2228 (Published online Dec. 4, 2011).

Lee, et al., "Fabrication and Characterization of Poly(Propylene Fumarate) Scaffolds with Controlled Pore Structures Using 3-Dimensional Printing and Injection Molding", University of South Carolina Scholar Commons Oct. 2006.

Fryhle et al., "Isomerization of Dimethyl Maleate to Dimethyl Fumarate" Journal of Chemical Education, vol. 68 No. 12 Dec. 1991, 1050-1051.

Jayablan, M., "Studies on Poly(propylene fumerate-co-caprolactone diol) Thermoset Composites towards the Development of Biodegradable Bone Fixation Devices", International Journal of Biomaterials, vol. 2009, pp. 1-10.

Wilson, et al., Immortal Ring Opening Polymerization of w-pentadecalactone by Mg(BHT)2(THF)2, Polymerchemistry, Feb. 25, 2014, vol. 5, pp. 2691-2694.

Wang. S. et al. "A Biodegradable and Cross-Linkable Multiblock Copolymer Consisting of Poly(propylene fumarate) and poly(e-caprolactone): Synthesis, Characterization, and Physical Properties" Macromolecules (2005) vol. 38, pp. 1-10.

* cited by examiner

BLOCK COPOLYMERS OF LACTONES AND POLY(PROPYLENE FUMARATE)

CROSS REFERENCE TO RELATED APPLICATIONS

This application claims the benefit of U.S. provisional patent application Ser. No. 62/543,786 entitled "Block Copolymers Of Lactones And Poly(Propylene Fumarate)" filed Feb. 2, 2017, U.S. provisional patent application Ser. No. 62/453,724 entitled "Copolymerization of Propylene Oxide And Maleic Anhydride using Mg Catalysts with Functional Initiators," filed Feb. 2, 2017, U.S. provisional patent application Ser. No. 62/500,777 entitled "Post-3D Printing Functionalization Polymer Scaffolds for Enhanced Bioactivity," filed May 3, 2017, U.S. provisional patent application Ser. No. 62/509,340 entitled "Functionalized Poly(Propylene Fumarate) Polymers and Methods for Their Making," filed May 22, 2017, U.S. provisional patent application Ser. No. 62/541,889 entitled "Synthesis and Characterization of Well Defined Poly(propylene fumarate) and Poly(ethylene glycol) Block Copolymers," filed Aug. 7, 2017, U.S. provisional patent application Ser. No. 62/561, 722 entitled "Mg Catalyzed Production of Poly(propylene fumarate) in Hexanes," filed Sep. 22, 2017, and U.S. patent application entitled "Functionalized Poly(propylene fumarate) Polymers Made by Ring Opening Polymerization Using Magnesium Catalysts," filed herewith by Applicant on Feb. 2, 2018, all of which are incorporated herein by reference in their entirety.

NAMES OF THE PARTIES TO A JOINT RESEARCH AGREEMENT

The present application is subject to a Joint Research Agreement between the University of Akron of Akron, Ohio and 21st Century Medical Technologies, Inc., of Akron, Ohio.

FIELD OF THE INVENTION

One or more embodiments of the present invention relates to novel block copolymers and methods for synthesizing various poly(lactone)s and poly(propylene fumarate) (PPF) polymers. In certain embodiments, the present invention relates to a well-defined biodegradable poly(lactone-b-propylene fumarate) polymers and scalable methods for making and functionalizing same.

BACKGROUND OF THE INVENTION

Aliphatic polyesters are a ubiquitous class of materials that have been studied extensively for sustainable alternatives to petroleum based products and specialized materials for biomedical devices as a consequence of their facile hydrolytic degradation, biocompatibility, and renewably sourced precursors. One of the most common synthetic method for obtaining aliphatic polyesters is the ring-opening polymerization (ROP) of lactones, which offers facile control of molecular mass, molecular mass distribution, and is atom economical in that no small-molecule byproducts are produced. However, limited functional diversity within the lactone monomer family and few options for post-polymerization modification have limited commercial use to a few examples in packaging and passive biomedical devices. An alternative chain-growth route to aliphatic polyesters that has generated substantial interest in the last few years is the ring-opening copolymerization of epoxides and anhydrides. The introduction of two distinct monomer species has allowed for tuning of properties and functionalities not accessible by the ROP of lactones.

To further expand the range of accessible polymers and their associated properties, the synthesis of aliphatic terpolyesters has been of particular interest recently. While the use of a mixed monomer feed has the potential to broaden the range of polymer properties, it also introduces a need for sequence selectivity. Block copolymers of polyesters, in particular, have found application in medicine, nanotechnology, lithography, photonics, and electronics. Numerous one-pot ROP systems based on empirical reactivity ratios have been utilized to produce block copolymers from lactones, and several one-pot ring-opening copolymerization (ROCOP) systems that rely on kinetic control have been reported, particularly with epoxides, anhydrides, and carbonates, to obtain block sequencing. Another method of producing block copolyesters involves linking ROP and ROCOP, a technique that typically relies on sequential additions and tandem catalysis. For example, a metal Salen catalyst has been used for the ROCOP of an epoxide with $CO_2$ prior to chain transfer by water and addition of an organo-catalyst for lactide ROP in a one-pot process. (See. e.g., Wu, G P; Darensbourg, D. J.; Mechanistic Insights into Water-Mediated Tandem Catalysis of Metal-Coordination $CO_2$/Epoxide Copolymerization and Organocatalytic Ring-Opening Polymerization: One-Pot, Two Steps, and Three Catalysis Cycles for Triblock Copolymers Synthesis. *Macromolecules*, 2016, 49 (3), pp 807-814, the disclosure of which in incorporated herein by reference in its entirety.) However, despite the chemical complexity obtained by linking two distinct polymerization cycles, the necessity of two separate catalysts increases cost and thus limits industrial viability.

To address this, a "switch" catalyst approach has been developed to produce sequence defined block copolymers in which ROP and ROCOP are combined in a one-pot system using a homogeneous, di-zinc catalyst. Unlike a standard terpolymerization, these "switch" method involves a mechanistic switch between distinct polymerization cycles using a single catalyst. With this method, a polymer composed of an alternating polycarbonate block and a lactone homopolymer block was produced from a mixture of cyclohexene oxide (CHO), ε-caprolactone (εCL), and $CO_2$. Since then, a small library of sequenced defined block copolymers have been developed using several different combinations of epoxide, anhydride, and lactone monomers with $CO_2$ and this method has been used to produce the only example of higher order block copolymers containing a polyester from the copolymerization of an epoxide and anhydride. Another instance of a "switch" catalyst system has recently reported in which a block copolymer was synthesized from a mixture of CHO, $CO_2$, and β-butyrolactone (BBL) using a di-zinc catalyst coordinated by a β-diiminate ligand. While, in these systems the selective ROCOP of CHO and $CO_2$ took place prior to the ROP of βBL, the sequencing was dependent on a very high $CO_2$ pressure (40 atm), and that at lower pressures a random incorporation occurred. No "switch" system, however, has successfully been developed for the production of polyesters with applications in additive manufacturing and regenerative medicine.

Advancements in additive manufacturing techniques are enabling the development of patient specific scaffolds and devices. However, these advances will be highly dependent on the availability of printable materials that meet the chemical, mechanical and biological requirements of the specific application. Various forms of additive manufacturing, more colloquially known as 3D printing, have been demonstrated in the literature. Fused deposition modelling (FDM) is a layer-by-layer method of extrusion molding solid filaments, such as poly(urethane)s (PUs), poly(L-lactic acid) (PLLA) or poly(ester urea)s (PEUs). Polymeric resins can also be printed using continuous digital light processing (cDLP), wherein photo-crosslinking in specific regions is achieved through high resolution stereolithography. Stereolithographic methods, such as cDLP, have been shown to exhibit much higher resolution compared to FDM techniques, as those are limited by the light source of the printer rather than the materials used. This enables 3D scaffolds to be printed with a controlled porosity that can be tailored to match physiological conditions. Inkjet methods have also been demonstrated in 3D printing and can be used with either powders or resins.

However, it is believed that patient specific devices will require highly specialized polymers that can be easily functionalized and tuned widely for both mechanical and degradation properties. Polyesters such as poly(ε-caprolactone) (PCL), poly(l-lactic acid) (PLLA), and poly(propylene fumarate) (PPF) have all been investigated as tissue engineering scaffolds, but each requires tuning of thermal, mechanical, rheological, and degradation properties before they can be used widely for regenerative medicine. Moreover, to be used to produce 3D scaffolds that are compatible with biological systems, the polymer should be non-toxic, implantable without rejection and completely resorbable upon degradation. While the first two criteria are achieved in a multitude of polymer systems, there are relatively few examples that are also bioresorbable; polylactides, poly(ε-caprolactone) (PCL) and poly(propylene fumarate) (PPF).

Each of these examples are polyesters and thus, able to degrade either enzymatically or through hydrolysis in vivo. However, as a consequence of the rapid degradation of PLLA, acidosis and inflammation of the surrounding tissue area are regularly observed. Conversely, the slow degradation of PCL in the human body limits its use in tissue repair, particularly with regards to reforming vascular tissue. Further, while both PLLA and PCL can be extruded through FDM to produce 3D scaffolds capable of undergoing in vitro degradation, these materials exhibit only moderate mechanical and tensile properties, with the majority of defects in the material are observed at the interface between deposited layers. And as a consequence of the achievable width of the extrusion nozzle in FDM, the resolution of the 3D printed scaffolds made using these polymers is limited.

PPF is an unsaturated polyester that can be formed by the ring-opening (co)polymerization (ROCOP) of maleic anhydride (MAn) and propylene oxide (PO) has been previously reported to produce the PPF cis-alkene isomer poly(propylene maleate) (PPM), which can be transformed into PPF using a weak base at low (60° C.) temperatures. Advantageously, ROCOP allows for a high degree of control over the molecular mass distribution and end-group fidelity through the variance of the ratio of monomer(s) to alcohol initiator. Recent studies of PPF synthesis via ROP, including contact cytotoxicity assays and cell culture results, have shown that PPF polymers produced by ROP are non-toxic and that cells attached and proliferated well on its thin films.

Furthermore, PPF degrades in vivo to form fumaric acid and propylene glycol, which are excreted naturally, and does not cause the acidosis and inflammation of the surrounding tissue area regularly observed with PLLA. PPF has been used for a variety of medical applications, such as vascular stents, nerve grafts, cartilage, drug release vehicles, blood vessel engineering, and bone tissue engineering. As a consequence of the unsaturated alkene in the polymer backbone, intermolecular crosslinking can be achieved in order to strengthen the mechanical properties of the material, giving it tunable mechanical properties better than those seen in conventional PLLA and PCL.

Conventional PPF polymers are not liquids at room temperature and have been formed into printable PPF resins by dissolving them into the reactive diluent diethyl fumarate (DEF), which acts as both solvent and crosslinking agent. These resins has been studied and shown to be able to produce 3D scaffolds with compressive moduli comparable to bone. A major drawback to the use of PPF polymers in these systems is that any excess DEF (i.e. any DEF not actually crosslinking the PPF polymer chains) must be removed before the printed structure can be used in biological systems.

Thus, what is needed in the art is a one-pot, scalable ring-opening block-order copolymerization (ROBOCOP) technique that utilizes catalyst that can "switch" from catalyzing the ROP of cyclic esters to catalyzing the ROCOP of maleic anhydride (MAn) and propylene oxide (PO) to produce lower viscosity PPF based block copolymers that require less solvent for applications in additive manufacturing and patient specific regenerative medicine and that avoid the limits of prior art systems.

SUMMARY OF THE INVENTION

In one or more embodiments, the present invention provide a well-defined biodegradable poly(lactone-b-propylene fumarate) polymers formed using a novel one-pot, scalable ring-opening block-order copolymerization (ROBOCOP) technique that utilizes magnesium 2,6-di-tert-butyl-4-methylphenoxide $(Mg(BHT)_2(THF)_2)$ to "switch" from the ROP of cyclic esters to the ROCOP of maleic anhydride (MAn) and propylene oxide (PO) to produce PPF based block copolymers for application in additive manufacturing and patient specific regenerative medicine. These block copolymers are fully resorbable and PPF based materials are unique in that they can be crosslinked photochemical in a number of applications, including 3D printing. The type and composition of the specific lactone block affords the ability to tune the physical, chemical and degradation properties for specific applications. In particular, it has been found that by adding the lactone block to the PPF polymer, the viscosity of the resulting block copolymer at working temperatures can be precisely controlled and the quantity of the reactive diluent diethyl fumarate (DEF), which acts as both solvent and crosslinking agent, used to form a printable resin can be reduced and in some cases eliminated.

In a first aspect, the present invention is directed to a block co-polymer comprising a poly(lactone) segment and a poly(propylene fumarate) segment. In one or more if these embodiments, the poly(lactone) segment comprises the residue of a lactone selected from the group consisting of δ-valerolactone, ε-caprolactone, α-chloro-ε-caprolactone, 4-chloro-ε-caprolactone, 4-methyl-7-isopropyl-ε-caprolactone (menthide), 2,5-oxepanedione (OPD), 7-methyl-4-(1-methylethenyl)-2-oxepanone (dihydrocarvide), 7-(prop-2-ynyl)oxepan-2-one, alkyl-substituted lactones, γ-methyl-ε-caprolactone, ε-heptalactone, ε-decalactone macrolactones, ω-pentadecalactone (PDL), functional lactones, θ-propargyl-ε-nonalactone (θpεNL), α-propargyl-ε-caprolactone (αpεCL), and combinations thereof.

In one or more embodiments, the block co-polymer of the present invention includes any one or more of the above referenced embodiments of the first aspect of the present invention further comprising a functional end group selected from the group consisting of benzyl groups, alkyne groups, propargyl groups, allyl groups, alkene groups, 4-dibenzocyclooctyne groups, cyclooctyne groups, ketone groups, aldehyde groups, tertiary halogen groups and poly(ethylene glycol) groups, and combinations thereof.

In one or more embodiments, the block co-polymer of the present invention includes any one or more of the above referenced embodiments of the first aspect of the present invention, wherein the poly(propylene fumarate) segment comprises from about 0.1 mole percent to about 99 mole percent of the end functionalized block co-polymer. In one or more embodiments, the block co-polymer of the present invention includes any one or more of the above referenced embodiments of the first aspect of the present invention wherein the poly(lactone) segment comprises from about 0.1 mole percent to about 99 mole percent of the end functionalized block co-polymer.

In one or more embodiments, the block co-polymer of the present invention includes any one or more of the above referenced embodiments of the first aspect of the present invention having a number average molecular weight ($M_n$) as measured by proton NMR of from about 0.5 kDa to about 500 kDa. In one or more embodiments, the block co-polymer of the present invention includes any one or more of the above referenced embodiments of the first aspect of the present invention having a number average molecular weight ($M_n$) as measured by GPC of from about 0.5 kDa to about 500 kDa. In one or more embodiments, the block co-polymer of the present invention includes any one or more of the above referenced embodiments of the first aspect of the present invention having a polydispersity index ($Đ_m$) of from about 1.1 to about 2.3.

In one or more embodiments, the block co-polymer of the present invention includes any one or more of the above referenced embodiments of the first aspect of the present invention having the formula:

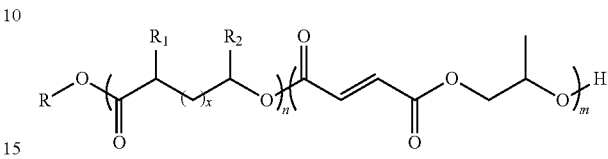

wherein n is an integer from about 1 to about 500; m is an integer from about 1 to about 500; x is an integer from about 1 to about 20; R is an end functional group selected from the group consisting of benzyl groups, alkyne groups, propargyl groups, allyl groups, alkene groups, 4-dibenzocyclooctyne groups, cyclooctyne groups, ketone groups, aldehyde groups, tertiary halogen groups, poly(ethylene glycol) groups, and combinations thereof; $R_1$ is a hydrogen atom, a propargyl group, or a $C_1$-$C_{10}$ alkyl group; and $R_2$ is a hydrogen atom, a methyl group, a butyl group, a propargyl group or a $C_1$-$C_{10}$ alkyl group. In one or more embodiments, the block co-polymer of the present invention includes any one or more of the above referenced embodiments of the first aspect of the present invention having the formula:

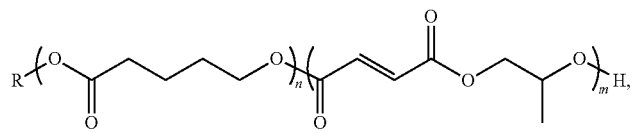

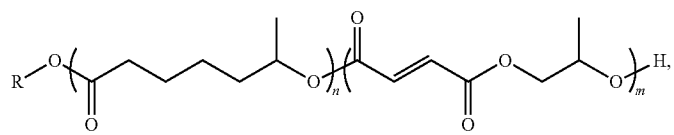

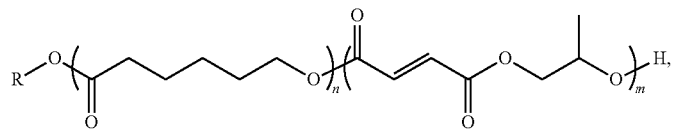

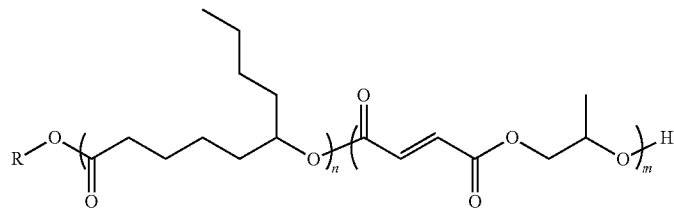

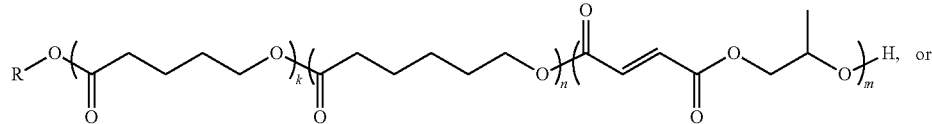

-continued

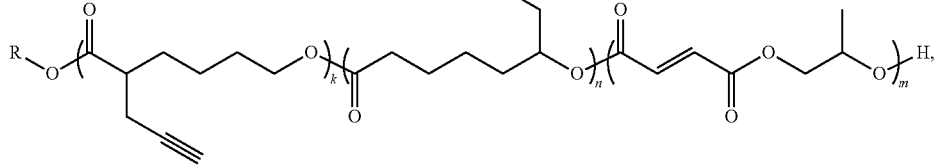

where n is an integer from about 1 to about 500; and m is an integer from about 1 to about; and k is an integer from about 1 to about 500; and R is an end functional group.

In a second aspect, the present invention is directed to a block co-polymer comprising the reaction product of a poly(lactone), maleic anhydride, and propylene oxide. In one or more of these embodiments, the poly(lactone) is an end functionalized poly(lactone). In one or more embodiments, the block co-polymer of the present invention includes any one or more of the above referenced embodiments of the second aspect of the present invention wherein the end functionalized poly(lactone) comprises an end functional group selected from the group consisting of benzyl groups, alkyne groups, propargyl groups, allyl groups, alkene groups, 4-dibenzocyclooctyne groups, cyclooctyne groups, ketone groups, aldehyde groups, tertiary halogen groups and poly(ethylene glycol) groups, and combinations thereof. In one or more embodiments, the block co-polymer of the present invention includes any one or more of the above referenced embodiments of the second aspect of the present invention wherein the poly(lactone) is selected from the group consisting of δ-valerolactone, ε-caprolactone, α-chloro-ε-caprolactone, 4-chloro-ε-caprolactone, 4-methyl-7-isopropyl-ε-caprolactone (menthide), 2,5-oxepanedione (OPD), 7-methyl-4-(1-methylethenyl)-2-oxepanone (dihydrocarvide), 7-(prop-2-ynyl)oxepan-2-one, alkyl-substituted lactones, γ-methyl-ε-caprolactone, ε-heptalactone, ε-decalactone macrolactones, ω-pentadecalactone (PDL), functional lactones, θ-propargyl-ε-nonalactone (θpεNL), α-propargyl-ε-caprolactone (αpεCL), and combinations thereof.

In one or more embodiments, the block co-polymer of the present invention includes any one or more of the above referenced embodiments of the second aspect of the present invention comprising from about 0.1 mole percent to about 99 mole percent of the residue of the end functionalized poly(lactone). In one or more embodiments, the block co-polymer of the present invention includes any one or more of the above referenced embodiments of the second aspect of the present invention having a number average molecular weight ($M_n$) as measured by NMR of from about 0.5 kDa to about 500 kDa. In one or more embodiments, the block co-polymer of the present invention includes any one or more of the above referenced embodiments of the second aspect of the present invention having a number average molecular weight ($M_n$) as measured by GPC of from about 0.5 kDa to about 100 kDa. In one or more embodiments, the block co-polymer of the present invention includes any one or more of the above referenced embodiments of the second aspect of the present invention having a polydispersity index ($Đ_m$) of from about 1.1 to about 2.3.

In a third aspect, the present invention is directed to a method for making the block co-polymers described above comprising: preparing an initiating alcohol; combining the initiating alcohol, a magnesium catalyst, and a lactone in a suitable reaction vessel; dissolving the contents of the reaction vessel with a suitable solvent; sealing and then heating the solution to cause or maintain the ring opening polymerization of the lactone, initiated by the initiating alcohol, thereby forming a poly(lactone) polymer; dissolving maleic anhydride and propylene oxide in a suitable solvent and adding them to the reaction vessel; heating the solution to form a block co-polymer comprising poly(lactone) segments and poly(propylene maleate) segments; and isomerizing the poly(propylene maleate) segments to form the poly(lactone-b-propylene fumarate) polymer. In one or more of these embodiments, the initiating alcohol is selected from the group consisting of benzyl alcohol, propargyl alcohol, allyl alcohol, 4-dibenzylcyclooctanol, 4-hydroxybutan-2-one, 3-hydroxypropan-2-one, 5-hydroxypentan-2-one, 6-hydroxyhexan-2-one, 7-hydroxyheptan-2-one, 8-hydroxyoctan-2-one, 5-norbornen-2-ol, PEG diol, α-bromoisobutyryl 4-methanol benzylmethanoate, and combinations thereof.

In one or more embodiments, the method of making block co-polymer of the present invention includes any one or more of the above referenced embodiments of the third aspect of the present invention wherein the initiating alcohol is end functionalized, the poly(lactone) polymer formed is an end functionalized lactone polymer, the block co-polymer comprising poly(lactone) segments and poly(propylene maleate) segments is end functionalized, and the poly(lactone-b-propylene fumarate) polymer produced is an end functionalized poly(lactone-b-propylene fumarate) polymer. In one or more embodiments, the method of making block co-polymer of the present invention includes any one or more of the above referenced embodiments of the third aspect of the present invention wherein the end functionalized poly(lactone-b-propylene fumarate) polymer comprises an end functional group selected from the group consisting of benzyl groups, alkyne groups, propargyl groups, allyl groups, alkene groups, 4-dibenzocyclooctyne groups, cyclooctyne groups, ketone groups, aldehyde groups, tertiary halogen groups and poly(ethylene glycol) groups and combinations thereof. In one or more embodiments, the method of making block co-polymer of the present invention includes any one or more of the above referenced embodiments of the third aspect of the present invention wherein the lactone is selected from the group consisting of δ-valerolactone, ε-caprolactone, α-chloro-ε-caprolactone, 4-chloro-ε-caprolactone, 4-methyl-7-isopropyl-ε-caprolactone (menthide), 2,5-oxepanedione (OPD), 7-methyl-4-(1-methylethenyl)-2-oxepanone (dihydrocarvide), 7-(prop-2-ynyl)oxepan-2-one, alkyl-substituted lactones, γ-methyl-ε-caprolactone, ε-heptalactone, ε-decalactone macrolactones, ω-pentadecalactone (PDL), functional lactones, θ-propargyl-ε-nonalactone (θpεNL), α-propargyl-ε-caprolactone (αpεCL), and combinations thereof.

In one or more embodiments, the method of making block co-polymer of the present invention includes any one or more of the above referenced embodiments of the third aspect of the present invention wherein the magnesium catalyst is Mg(BHT)$_2$(THF)$_2$. In one or more embodiments, the method of making block co-polymer of the present invention includes any one or more of the above referenced embodiments of the third aspect of the present invention wherein the concentration of the lactone in the solution is from about 0.5 M to about 10 M. In one or more embodiments, the method of making block co-polymer of the present invention includes any one or more of the above referenced embodiments of the third aspect of the present invention wherein the total concentration of the maleic anhydride and the propylene oxide in the solution is from about 0.5 M to about 10 M. In one or more embodiments, the method of making block co-polymer of the present invention includes any one or more of the above referenced embodiments of the third aspect of the present invention wherein the lactone solution is heated to a temperature of from about 40° C. to about 100° C. In one or more embodiments, the method of making block co-polymer of the present invention includes any one or more of the above referenced embodiments of the third aspect of the present invention wherein the lactone solution of is heated for from about 1 hour to about 96 hours.

In one or more embodiments, the method of making block co-polymer of the present invention includes any one or more of the above referenced embodiments of the third aspect of the present invention wherein the poly(lactone) polymer, maleic anhydride, propylene oxide solution is heated to a temperature of from about 40° C. to about 100° C. In one or more embodiments, the method of making block co-polymer of the present invention includes any one or more of the above referenced embodiments of the third aspect of the present invention wherein the poly(lactone) polymer, maleic anhydride, propylene oxide solution is heated for from about 1 hours to about 96 hours.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF THE ILLUSTRATIVE EMBODIMENTS

Figure 1:
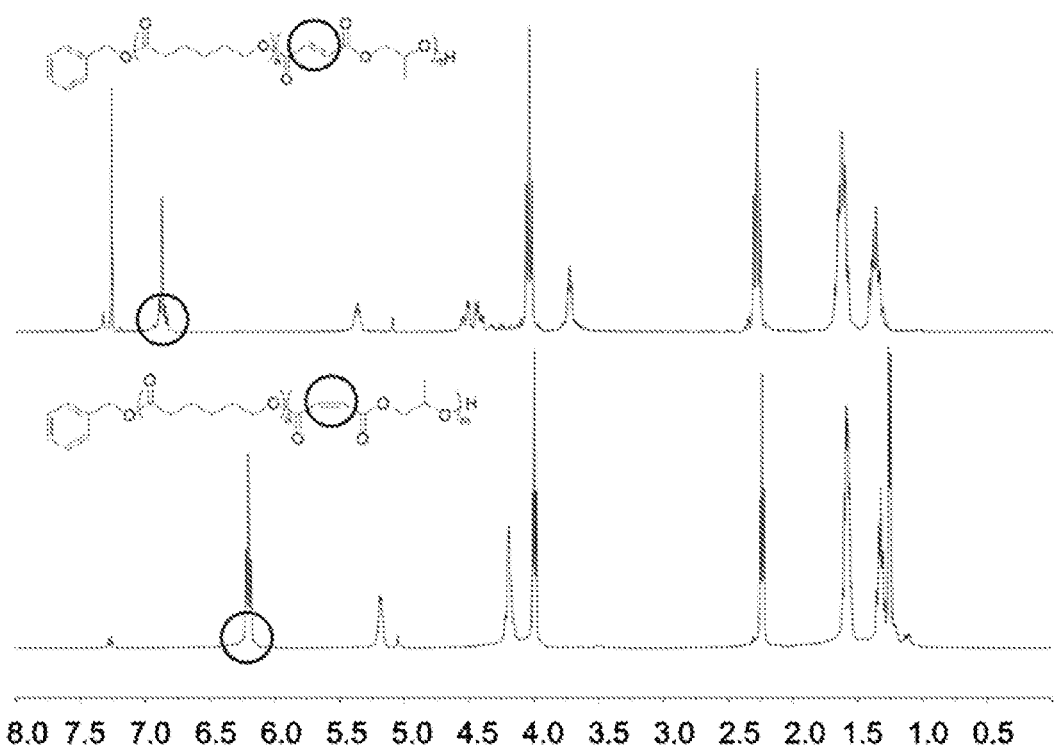
FIG. 1 is a $^1$H NMR spectra of DP 50 Poly(ε-caprolactone-b-propylene maleate) (bottom) and Poly(ε-caprolactone-b-propylene fumarate) (top) (300 MHz, CDCl$_3$, 303 K).

One or more embodiments of the present invention provide a well-defined, non-toxic, resorbable end functionalized poly(lactone-b-propylene fumarate) block copolymers (and related methods for their making and use) having constrained and predictable material properties suitable for 3D printing and other regenerative medicine applications. These block copolymers are fully resorbable and PPF based materials are unique in that they can be crosslinked photochemical in a number of applications, including 3D printing. The type and composition of the specific lactide block affords the ability to tune the physical, chemical and degradation properties for specific applications. In particular, it has been found that by adding the lactone block to the PPF polymer, the viscosity of the resulting block copolymer and can be precisely controlled. Moreover, it has been found that the amount of DEF required to formulate 3D printable resin is greatly reduced, both because less DEF is required to dilute the PPF and because the presence of the lactone block allow for longer PPF blocks, reducing the amount of DEF necessary for crosslinking. In certain embodiments, the present invention relates to a well-defined biodegradable poly(lactone-b-propylene fumarate) polymers and scalable methods for making and functionalizing same.

In various embodiments, the poly(lactone-b-propylene fumarate) block copolymers of the present invention will have a poly(lactone) segment (block) and a poly(propylene fumarate) segment (block), and may optionally include an end functional group introduced through the initiating alcohol and/or one or more other functional groups introduced through a functionalized lactone monomer.

In various embodiments, the poly(lactone) segment (block) of poly(lactone-b-propylene fumarate) block copolymers of the present invention are formed through ring opening polymerization of one or more lactone monomers from an initiating alcohol, which may, or may not, include an end functional group, as described below. The poly(lactone) segment (block) will comprise a polymer chain formed of the residues of the lactones from which it was formed and will be bonded on one end to the residue of the initiating alcohol and on the other end to the poly(propylene fumarate) segment (block). As used herein, the term "residue(s)" is used to refer generally to the part of a monomer or other chemical unit that has been incorporated into a polymer or other large molecule. Any lactone capable of ring opening polymerization from an alcohol using a suitable catalyst may be used. In one or more embodiments, the poly(lactone) segment (block) may include the residue of lactones such as δ-valerolactone (δVL), ε-caprolactone (εCL), α-chloro-ε-caprolactone, 4-chloro-ε-caprolactone, 4-methyl-7-isopropyl-ε-caprolactone (menthide), 2,5-oxepanedione (OPD), 7-methyl-4-(1-methylethenyl)-2-oxepanone (dihydrocarvide), 7-(prop-2-ynyl)oxepan-2-one, alkyl-substituted lactones including, but not limited to, γ-methyl-ε-caprolactone (γmεCL), ε-heptalactone (EHL), ε-decalactone (EDL) macrolactones, including, but not limited to, ω-pentadecalactone (PDL), functional lactones including, but not limited to, θ-propargyl-ε-nonalactone (θpεNL), α-propargyl-ε-caprolactone (αpεCL), and isomeric mixtures thereof.

In various embodiments, the poly(lactone) segment will comprise from about 0.1 mole percent to about 99 mole percent of said end functionalized block co-polymer. In some embodiments, the poly(lactone) segment will comprise from about 0.1 mole percent to about 90 mole percent, in other embodiments, from about 0.1 mole percent to about 75 mole percent, in other embodiments, from about 0.1 mole percent to about 50 mole percent, in other embodiments, from about 0.1 mole percent to about 40 mole percent, in other embodiments, from about 0.1 mole percent to about 25 mole percent, and in other embodiments, from about 0.1 mole percent to about 10 mole percent, of said end functionalized block co-polymer.

As set forth above, the poly(lactone-b-propylene fumarate) block copolymers of the present invention also comprise a the poly(propylene fumarate) (PPF) segment (block). As will be appreciated by those of skill in the art, the PPF segment (block) is formed by the isomerization of a poly(propylene maleate) segment formed by ring opening polymerization of maleic anhydride and propylene oxide onto the end of the poly(lactone) segment (block) and will comprise the isomerized residue of those maleic anhydride and propylene oxide monomers. In various embodiments, the PPF segment of the poly(lactone-b-propylene fumarate) block copolymers of the present invention will comprise from about 0.1 mole percent to about 99 mole percent of said end functionalized block co-polymer. In some embodiments, the PPF segment will comprise from about 0.1 mole percent to about 90 mole percent, in other embodiments, from about 0.1 mole percent to about 75 mole percent, in other embodiments, from about 0.1 mole percent to about 50 mole percent, in other embodiments, from about 0.1 mole percent to about 40 mole percent, in other embodiments, from about 0.1 mole percent to about 25 mole percent, in other embodiments, from about 0.1 mole percent to about 10 mole percent, in other embodiments, from about 10 mole percent to about 99 mole percent, in other embodiments, from about 25 mole percent to about 99 mole percent of said end functionalized block co-polymer, in other embodiments, from about 50 mole percent to about 99 mole percent, in other embodiments, from about 75 mole percent to about 99 mole percent.

Further, while the block copolymers of the present invention will have at least one lactone segment and at least one PPF segment, in some other embodiments, the block copolymers of the present invention may have more than one lactone block and/or more than one PPF block. In addition, in one or more of these embodiments, more than one type of lactone block may be used, either in the same block as a terpolymer or in separate lactone blocks. In some other embodiments, a single lactone block may contain a mixture of the residues of more than one different lactone. In some of these embodiments, the block copolymers of the present invention may have two or more lactone or two or more PPF blocks that have different chain lengths.

As set forth above, the poly(lactone-b-propylene fumarate) block copolymers of the present invention may in some embodiments include one or more functional groups to facilitate post polymerization addition of desirable materials, such as bioactive materials or other functional species, to the polymer. As used herein, the terms "bioactive molecule(s)" and "bioactive material(s) are used interchangeably to refer to substances that influence cellular function and may include, without limitation, peptides, carbohydrates, proteins, oligonucleotides and small molecule drugs. As used in the context of substances that may be attached to the functionalized PPF polymers of the present invention, the term "functional species" refers to substances other than bioactive materials that may be added to the functionalized PPF polymers of the present invention to provide an added benefit and may include such things as fluorescent and other markers, small molecule dyes, and/or drugs.

In some embodiments, the poly(lactone-b-propylene fumarate) block copolymers of the present invention may include an end functional group introduced through the initiating alcohol. These end functional groups are not particularly limited provided that they maintain at least some of their reactivity after the polymerization and isomerization reactions discussed below, and may include without limitation, benzyl groups, alkyne groups, propargyl groups, allyl groups, alkene groups, 4-dibenzocyclooctyne groups, cyclooctyne groups, ketone groups, aldehyde groups, tertiary halogen groups or a combination thereof.

In some other embodiments, the PPF block of the poly(lactone-b-propylene fumarate) block copolymers of the present invention may also include one or more monomer functional groups introduced through a functionalized monomer. In these embodiments, the PPF segment (block) will comprise the isomerized residue of the maleic anhydride monomer and the residue of a functionalized propylene oxide monomer used in its formation. As will be apparent, when the maleic anhydride monomer and the functionalized propylene oxide monomer react to form the polymer, the maleic anhydride monomer and functionalized propylene oxide will form the backbone of the PPM/PPF polymer, with the functional group of the functionalized propylene oxide monomer forming an active side chain. In various embodiments, the functional group on the residue of the functionalized propylene oxide monomer may include, without limitation, an alkyne group, a propargyl group, an alkene group, a hydroxyl group, a ketone group, a thiol group, a halide group, a nitrobenzyl group, or a group that can easily be converted into such a functional group such as a halide group, or a nitrobenzyl group. In the same way, in other embodiments, functional groups may be introduced into the block co polymers of the present invention through the lactone monomers, which may contain, or be functionalized to contain, additional functional groups.

As used herein, the term "residue(s)" is used to refer generally to the part of a monomer or other chemical unit that has been incorporated into a polymer or large molecule. By extension, the terms "residue of the maleic anhydride monomer" and the "residue of functionalized propylene oxide monomer" are used to refer to the parts of the maleic anhydride monomer and functionalized propylene oxide monomer, respectively, that has been incorporated into the PPM and PPF block of the poly(lactone-b-propylene fumarate) block copolymers of the present invention. The term "isomerized residue of a maleic anhydride monomer" specifically refers to the residue of the maleic anhydride monomer in the PPF block of the poly(lactone-b-propylene fumarate) block copolymers of the present invention wherein the double bond has been isomerized from the cis configuration to the trans configuration with the formation of the functionalized PPF polymer.

In various embodiments, the functional group on the residue of the functionalized propylene oxide monomer may include, without limitation, an alkyne group, a propargyl group, an alkene group, a hydroxyl group, a ketone group, a thiol group, a halide group, a nitrobenzyl group, or a group that can easily be converted into such a functional group such as a halide group or a nitrobenzyl group. It has been found that using the monomer functionalization method increases the quantity of available functional groups compared to only end-group functionalization, even with less functional groups surviving processing. It has also been found that the monomer of the PPF polymers of the present invention to not significantly affect the desired mechanical, thermal, degradation, and/or toxicity properties of the polymers.

In some embodiments, the functional groups added to the poly(lactone-b-propylene fumarate) block copolymers of the present invention will be groups capable of well known "click" reactions to facilitate post polymerization addition of desirable materials, such as bioactive compounds, to the polymer. As used herein, the terms "click reaction," "click chemistry," "click chemistry methods," "click chemistry reactions," are used interchangeably to refer to a group of orthogonal conjugation reactions, generally referred to in the art as "click" reactions, that fulfill the following prerequisites: (i) high yield, nearly quantitative conversion; (ii) biologically benign conditions (aqueous solution, ambient temperature, and near physiologic pH); (iii) limited or no residual byproduct. These reactions are typically simple to perform, high yielding, stereospecific, wide in scope, create only byproducts that can be removed without chromatography, and can be conducted in easily removable or benign solvents. Similarly, the term "clickable" refers to a molecule or functional group capable of bonding via a click reaction.

The "click" chemistry concept currently represents a number of orthogonal reactions, which are robust, selective, efficient, and high yielding, including, without limitation, copper (I) catalyzed azide-alkyne cycloaddition (CuAAC) reactions (a.k.a. Huisgen cycloaddition reactions), thiol-ene radical addition reactions, oxime ligation reactions, Michael-addition reactions, thiol-Michael-addition reactions, Mannich-type addition reactions, "ene-type" addition reactions, thiol-ene radical addition, strain promoted azide-alkyne cycloaddition (SPAAC) reactions, non-traceless Staudinger ligation, traceless Staudinger ligation, Diels-Alder reactions, hetero Diels-Alder reactions, inverse electron demand Diels-Alder reactions, tandem [3+2] cycloaddition-retro-Diels-Alder (tandem crD-A) reactions, thiol-alkyne reactions, thiol-pyridyl disulfide reactions, thiol-halogen ligation, native chemical ligation, and thiazolidine ligation reactions. In one or more embodiments, suitable "clickable" moieties may include, without limitation, alkyne groups, alkene groups, azide groups, ketones or strained cyclooctyne groups In one or more of these embodiments, the bioactive or other material to be attached to the polymer is functionalized with a moiety known to bond the functional group used via a click reaction. The clickable moiety chosen and means for its attachment will, of course, depend upon the bioactive or other material to be attached and the specific click reaction to be used. One of ordinary skill in the art will be able to attach the appropriate clickable moiety to the bioactive or other material to be attached without undue experimentation.

In one or more embodiments, the block co-polymer of present invention will have the formula:

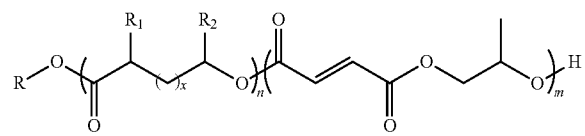

wherein n is an integer from about 1 to about 500; m is an integer from about 1 to about 500; x is an integer from about 1 to about 20; R is an end group comprising the residue of the initiating alcohol and preferably comprises an end functional group; $R_1$ is a hydrogen atom, a propargyl group, or a $C_1$-$C_{10}$ alkyl group; and $R_2$ is a hydrogen atom, a methyl group, a butyl group, a propargyl group or a $C_1$-$C_{10}$ alkane.

In one or more of these embodiments, R may be a benzyl group, alkyne group, propargyl group, allyl group, alkene group, 4-dibenzocyclooctyne group, cyclooctyne group, ketone group, aldehyde group, tertiary halogen group and poly(ethylene glycol) group, and combinations thereof. In some of these embodiments, n is an integer from about 1 to about 400, in other embodiments, from about 1 to about 300, in other embodiments, from about 1 to about 200, in other embodiments, from about 1 to about 100, in other embodiments, from about 500 to about 500, in other embodiments, from about 150 to about 500, in other embodiments, from about 250 to about 500, and in other embodiments, from about 350 to about 500. In some of these embodiments, m is an integer from about 1 to about 400, in other embodiments, from about 1 to about 300, in other embodiments, from about 1 to about 200, in other embodiments, from about 1 to about 100, in other embodiments, from about 500 to about 500, in other embodiments, from about 150 to about 500, in other embodiments, from about 250 to about 500, and in other embodiments, from about 350 to about 500.

In some of these embodiments, x is an integer from about 1 to about 20, in other embodiments, from about 1 to about 15, in other embodiments, from about 1 to about 10, in other embodiments, from about 1 to about 5, in other embodiments, from about 1 to about 3. In some of these embodiments, $R_1$ may be a hydrogen atom, a propargyl group or a $C_1$-$C_{10}$ alkyl group. In some of these embodiments, $R_2$ may be a hydrogen atom, a methyl group, a butyl group, a propargyl group or a $C_1$-$C_{10}$ alkyl group.

In some embodiments, the block co-polymers of the present invention may have the formula:

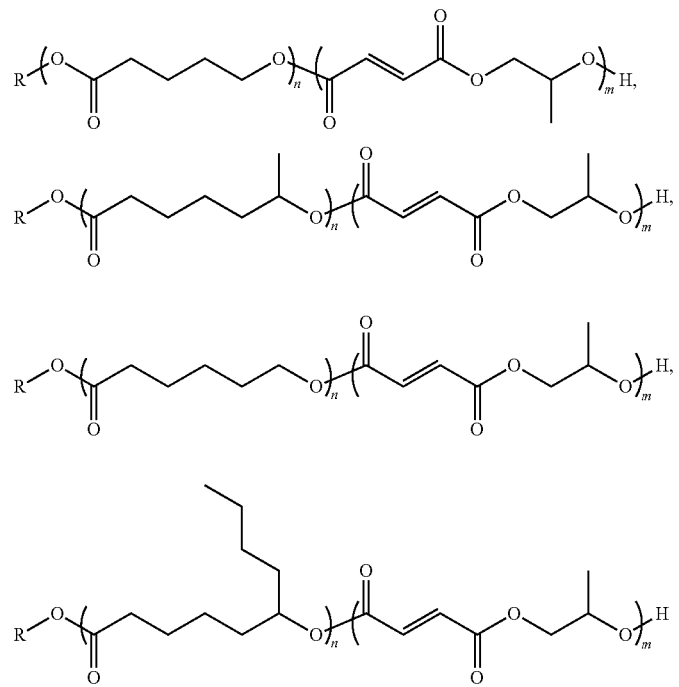

-continued

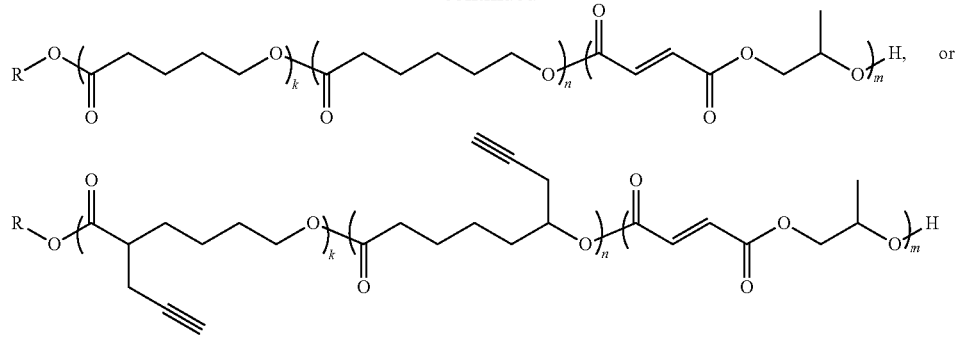

where n is an integer from about 1 to about 500; m is an integer from about 1 to about 500; k is an integer from about 1 to about 500; and R is an end group comprising the residue of the initiating alcohol, and preferably comprises an end functional group, as described above.

In one or more of these embodiments, R may be a benzyl group, alkyne group, propargyl group, allyl group, alkene group, 4-dibenzocyclooctyne group, cyclooctyne group, ketone group, aldehyde group, tertiary halogen group and poly(ethylene glycol) group, or a combination thereof. In some of these embodiments, n is an integer from about 1 to about 400, in other embodiments, from about 1 to about 300, in other embodiments, from about 1 to about 200, in other embodiments, from about 1 to about 100, in other embodiments, from about 500 to about 500, in other embodiments, from about 150 to about 500, in other embodiments, from about 250 to about 500, and in other embodiments, from about 350 to about 500. In some of these embodiments, m is an integer from about 1 to about 400, in other embodiments, from about 1 to about 300, in other embodiments, from about 1 to about 200, in other embodiments, from about 1 to about 100, in other embodiments, from about 500 to about 500, in other embodiments, from about 150 to about 500, in other embodiments, from about 250 to about 500, and in other embodiments, from about 350 to about 500. In some of these embodiments, k is an integer from about 1 to about 400, in other embodiments, from about 1 to about 300, in other embodiments, from about 1 to about 200, in other embodiments, from about 1 to about 100, in other embodiments, from about 500 to about 500, in other embodiments, from about 150 to about 500, in other embodiments, from about 250 to about 500, and in other embodiments, from about 350 to about 500.

In some embodiments, the block copolymers of the present invention may have a number average molecular weight ($M_n$) of from about 0.5 kDa to about 500 kDa, as determined by end-group analysis using $^1$H NMR spectroscopic analysis. In some embodiments, the poly(lactone-b-propylene fumarate) block copolymers of the present invention will have a number average molecular weight ($M_n$) of from about 0.5 kDa to about 400 kDa, in other embodiments, from about 0.5 kDa to about 300 kDa, in other embodiments, from about 0.5 kDa to about 200 kDa, in other embodiments, from about 0.5 kDa to about 100 kDa, in other embodiments, from about 50 kDa to about 500 kDa, in other embodiments, from about 150 kDa to about 500 kDa, and in other embodiments, from about 250 kDa to about 500 kDa, as determined by end-group analysis using $^1$H NMR spectroscopic analysis.

In some embodiments, the block copolymers of the present invention may have a number average molecular weight ($M_n$) of from about 0.5 kDa to about 500 kDa, as determined by size exclusion chromatography (SEC) in THF against poly(styrene) standards. In some embodiments, the poly(lactone-b-propylene fumarate) block copolymers of the present invention will have a number average molecular weight ($M_n$) of from about 0.5 kDa to about 400 kDa, in other embodiments, from about 0.5 kDa to about 300 kDa, in other embodiments, from about 0.5 kDa to about 200 kDa, in other embodiments, from about 0.5 kDa to about 100 kDa, in other embodiments, from about 50 kDa to about 500 kDa, in other embodiments, from about 150 kDa to about 500 kDa, and in other embodiments, from about 250 kDa to about 500 kDa, as determined by size exclusion chromatography (SEC) in THF against poly(styrene) standards.

In some embodiments, the block copolymers of the present invention may have a weight average molecular weight ($M_w$) of from about 2 kDa to about 500 kDa, as determined by SEC in THF against poly(styrene) standards. In some embodiments, the poly(lactone-b-propylene fumarate) block copolymers of the present invention will have a weight average molecular weight ($M_w$) of from about 2 kDa to about 250 kDa, in other embodiments, from about 2 kDa to about 100 kDa, in other embodiments, from about 2 kDa to about 50 kDa, in other embodiments, from about 2 kDa to about 25 kDa, in other embodiments, from about 2 kDa to about 10 kDa, as determined by size exclusion chromatography (SEC) in THF against poly(styrene) standards.

In various embodiments, the poly(lactone-b-propylene fumarate) block copolymers of the present invention may have a polydispersity ($Đ_M$) of from about 1.1 to about 2.3, as determined by SEC in THF against poly(styrene) standards. In some embodiments, the poly(lactone-b-propylene fumarate) block copolymers of the present invention will have a polydispersity ($Đ_M$) of from about 1.1 to about 2.1, in other embodiments, from about 1.1 to about 1.8, in other embodiments, from about 1.1 to about 1.5, in other embodiments, from about 1.3 to about 2.3, in other embodiments, from about 1.5 to about 2.3, in other embodiments, from about 1.8 to about 2.3, and in other embodiments, from about 2.0 to about 2.3, as determined by SEC in THF against poly(styrene) standards.

As will be apparent, the poly(lactone-b-propylene fumarate) block copolymers of the present invention may be photochemically crosslinked using diethyl fumarate (DEF) in the same manner as other poly(propylene fumarate) polymers, making them useful for the production of polymer structures such as tissue scaffolds. In one or more of these embodiments, the poly(lactone-b-propylene fumarate) block copolymers of the present invention may be are formed into a 3-D printable resin. In these embodiments, the poly (lactone-b-propylene fumarate) block copolymer is dissolved into diethyl fumarate (DEF) and conventional photoinitiators and light scattering agents are mixed evenly throughout the resin. It has been found that the amount of DEF required to formulate 3D printable resin is greatly reduced for the poly(lactone-b-propylene fumarate) block copolymers of the present invention, both because less DEF is required to dilute the PPF and because the presence of the lactone block allow for longer PPF blocks, reducing the amount of DEF necessary for crosslinking. The resin is then 3-D printed and photo-crosslinked with a cDLP printer or other suitable 3-D printer to form a scaffold or other polymer structure.

In another aspect, the present invention is directed to a method of making the poly(lactone-b-propylene fumarate) block copolymers described above. In various embodiments, the end functionalized poly(lactone-b-propylene fumarate) block copolymers of the present invention are made using a three step process: (i) formation of the end functionalized poly(lactone) segment (block) (which may or may not be end functionalized) via ring opening polymerization of a lactone using a starting alcohol and a magnesium catalyst; (ii) formation of a poly(propylene maleate) segment (block) on the end of the end functionalized poly(lactone) segment (block) via ring opening polymerization of maleic anhydride and propylene oxide; and (iii) isomerization of the poly (propylene maleate) segment (block) into its trans-isomer (poly(propylene fumarate)) form using any method known in the art for that purpose to form a poly(lactone-b-propylene fumarate) block copolymer.

In the first step, an initiating alcohol, a lactone monomer, and a magnesium catalyst, preferably $Mg(BHT)_2(THF)_2$, are placed in an ampule or other suitable reaction vessel and dissolved in a suitable solvent, such as toluene. The choice of solvent is not particularly limited and one of ordinary skill in the art will be able to select a suitable solvent without undue experimentation.

As set forth above, any lactone may be used as the lactone monomer provided it is capable of ring opening polymerization from an alcohol initiator using a suitable catalyst such as $Mg(BHT)_2(THF)_2$. Suitable lactone monomers may include, without limitation, δ-valerolactone (δVL), ε-caprolactone (εCL), α-chloro-ε-caprolactone, 4-chloro-ε-caprolactone, 4-methyl-7-isopropyl-ε-caprolactone (menthide), 2,5-oxepanedione (OPD), 7-methyl-4-(1-methylethenyl)-2-oxepanone (dihydrocarvide), 7-(prop-2-ynyl)oxepan-2-one, alkyl-substituted lactones including, but not limited to, γ-methyl-ε-caprolactone (γmεCL), ε-heptalactone (EHL), ε-decalactone (EDL), macrolactones, including, but not limited to, ω-pentadecalactone (PDL), functional lactones including, but not limited to, θ-propargyl-ε-nonalactone (θpεNL), α-propargyl-ε-caprolactone (αpεCL) and isomeric mixtures thereof, or any combination thereof.

The initiating alcohol is not particularly limited, but it should be noted that different initiating alcohols will have different rate constants and will drive the reaction at different rates. In one or more embodiment, suitable initiating alcohols may include, without limitation, benzyl alcohol, ethanol, isopropanol, glycerol, propargyl alcohol, allyl alcohol, 4-dibenzylcyclooctanol, 4-hydroxybutan-2-one, 3-hydroxypropan-2-one, 5-hydroxypentan-2-one, 6-hydroxyhexan-2-one, 7-hydroxyheptan-2-one, 8-hydroxyoctan-2-one, 5-norbornen-2-ol, α-bromoisobutyryl 4-methanol benzylmethanoate, poly(ethylene glycol)s or a combination thereof.

As set forth above, a functional end group may be added to the polymer through the initiating alcohol. These materials have a hydroxyl group that initiates the ring open polymerization reaction and a functional end group useful for post polymerization reactions that survives both the polymerization and isomerization reactions. These functional end groups are not particularly limited provided that they maintain at least some of their reactivity after the polymerization and isomerization reactions, and may include without limitation, benzyl groups, alkyne groups, propargyl groups, allyl groups, alkene groups, 4-dibenzocyclooctyne groups, cyclooctyne groups, ketone groups, aldehyde groups, and tertiary halogen groups or a combination thereof.

In various embodiments, the magnesium catalyst may be any magnesium or other organometallic catalyst that is substantially non-toxic and capable of catalyzing the ROP of lactones and the ROP of maleic anhydride and propylene oxide monomers without out being consumed, but is preferably $Mg(BHT)_2(THF)_2$.

The reaction solvent used is not particularly limited, and may be any suitable solvent or solvent combination that can dissolve not only the lactone monomers in step 1, but also the maleic anhydride and propylene oxide monomers of step 2 and is miscible with the solvent used to dissolve the maleic anhydride and propylene oxide monomers. In various embodiments, suitable solvents may include, without limitations, toluene, hexanes, heptane, hexane, octane, or a combination thereof. One of ordinary skill in the art will be able to select a suitable solvent without undue experimentation.

In various embodiments, the concentration of the lactone monomer in the starting solution will be from about 0.5 M to about 10 M. In some embodiments, the lactone monomer concentration is from about 1 M to about 7 M, in other embodiments, from about 2 M to about 5 M, in other embodiments, from about 3 M to about 5 M, in other embodiments, from about 0.5 M to about 4 M, in other embodiments, from about 0.5 M to about 3 M, and in other embodiments, from about 0.5 M to about 2 M. Next, the reaction vessel is then sealed and the lactone solution heated to a temperature of from about 40° C. to about 100° C. to begin and/or maintain a ring opening polymerization reaction of the lactone, initiated by the initiating alcohol and catalyzed by the magnesium catalyst, to form a poly(lactone) polymer intermediate. In some embodiments, the lactone solution is heated to a temperature of from about 40° C. to about 50° C., in other embodiments from about 40° C. to about 60° C., in other embodiments from about 40° C. to about 70° C., in other embodiments from about 40° C. to about 80° C., and in other embodiments from about 40° C. to about 90° C. As will be apparent, these poly(lactone) polymer intermediates will have the functional end group from the initiating alcohol, if any, on one end and a hydroxyl (OH) group on the other end. In some embodiments, the lactone solution is heated until substantially all (98% or more) of the lactone has reacted.

In various embodiments, the lactone solution may be heated for from about 1 hour to about 96 hours. In some embodiments, the lactone solution is heated for from about 1 hour to about 84 hours, in other embodiments, from about 1 hour to about 72 hours, in other embodiments, from about 1 hour to about 60 hours, in other embodiments, from about 1 hour to about 48 hours, in other embodiments, from about 1 hour to about 36 hours, in other embodiments, from about 1 hour to about 24 hours, and in other embodiments, from about 1 hour to about 12 hours.

In the second step, a maleic anhydride monomer and a propylene oxide monomer are dissolved in a suitable solvent, such as toluene, to a total monomer concentration of from about 0.5 M to about 10 M and added to the reaction vessel containing the poly(lactone) polymer intermediate. In some embodiments, the total monomer concentration is from about 1 M to about 7 M, in other embodiments, from about 2 M to about 5 M, in other embodiments, from about 3 M to about 5 M, in other embodiments, from about 0.5 M to about 4 M, in other embodiments, from about 0.5 M to about 3 M, and in other embodiments, from about 0.5 M to about 2 M.

As will be apparent, no additional catalyst or initiating alcohol is required in this step since the poly(lactone) polymer intermediate functions as the initiating alcohol for the ROP of the maleic anhydride and propylene oxide monomers and the magnesium catalyst simply switches from catalyzing the ROP of the lactone to the ROP of the maleic anhydride and propylene oxide monomers. In some embodiments, functionalized propylene oxide monomers may be used to introduce monomer functional groups to the PPF block of the block co-polymer.

The resulting solution is then heated to a temperature of from about 40° C. to about 100° C. to begin and/or maintain a ring opening polymerization reaction of the maleic anhydride monomer and propylene oxide monomer to the terminal OH group on the poly(lactone) polymer intermediate to form a poly(lactone-b-propylene maleate) block copolymer intermediate. In some embodiments, the solution is heated to a temperature of from 40° C. to about 50° C., in other embodiments from about 40° C. to about 60° C., in other embodiments from about 40° C. to about 70° C., in other embodiments from about 40° C. to about 80° C., and in other embodiments from about 40° C. to about 90° C. In some embodiments, the solution is heated until substantially all (80% or more) of the monomer has reacted. In some embodiments, the solution is heated for from about 1 hour to about 96 hours, in other embodiments, from about 12 hour to about 96 hours, in other embodiments, from about 24 hour to about 96 hours, in other embodiments, from about 48 hour to about 96 hours, in other embodiments, from about 62 hour to about 96 hours, in other embodiments, from about 1 hour to about 62 hours, and in other embodiments, from about 1 hour to about 48 hours.

In one or more embodiments, an end functionalized poly(lactone-b-propylene maleate) block copolymer intermediate may be formed as shown in Scheme 1, below:

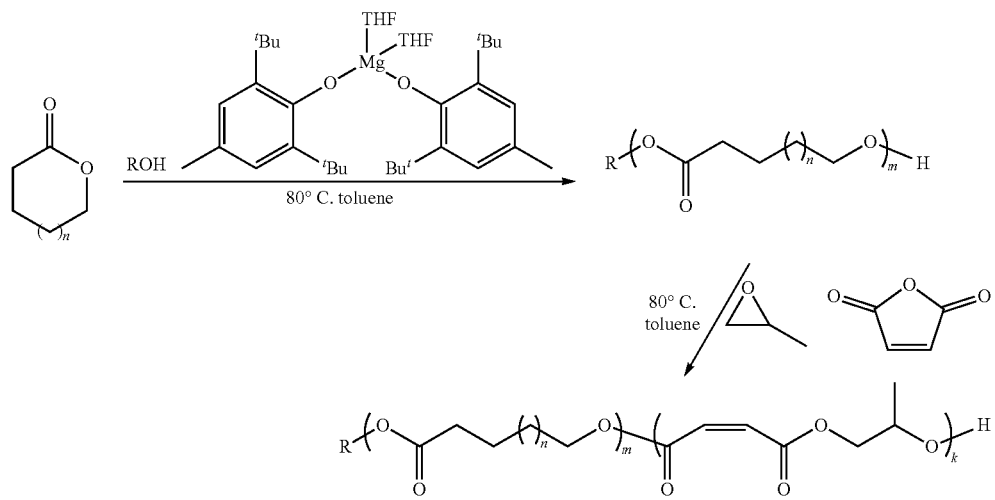

Scheme 1
Proposed synthetic method for block copolymers containing lactones and poly(propylene maleate)

where R is an end group or end functional group as described above; n is an integer from about 1 to about 20; m is an integer from about 1 to about 500; and k is an integer from about 1 to about 100. In various embodiments, R may be a an alkyne group, a propargyl group, an alkene group, a hydroxyl group, a ketone group, a thiol group, a halide group, a nitrobenzyl group, or a group that can easily be converted into such a functional group such as a halide group or a nitrobenzyl group.

In some embodiments, n may be an integer from about 1 to about 15, in other embodiments, from about 1 to about 10, in other embodiments, from about 1 to about 8, in other embodiments, from about 1 to about 6, in other embodiments, from about 1 to about 4, in other embodiments, from about 5 to about 20, and in other embodiments, from about 10 to about 20. In some embodiments, m may be an integer from about 1 to about 400, in other embodiments, from about 1 to about 300, in other embodiments, from about 1 to about 200, in other embodiments, from about 1 to about 100, in other embodiments, from about 1 to about 50, in other embodiments, from about 1 to about 25, in other embodiments, from about 100 to about 400, and in other embodiments, from about 200 to about 400. In some embodiments, k may be an integer from about 1 to about 80, in other embodiments, from about 1 to about 60, in other embodiments, from about 1 to about 40, in other embodiments, from about 1 to about 20, in other embodiments, from about 1 to about 10, in other embodiments, from about 20 to about 80, in other embodiments, from about 40 to about 80, in other embodiments, from about 50 to about 80, and in other embodiments, from about 60 to about 100.

In some embodiments, poly(lactone-b-propylene maleate) block copolymer intermediate may be synthesized as shown in Scheme 2, below.

Scheme 2

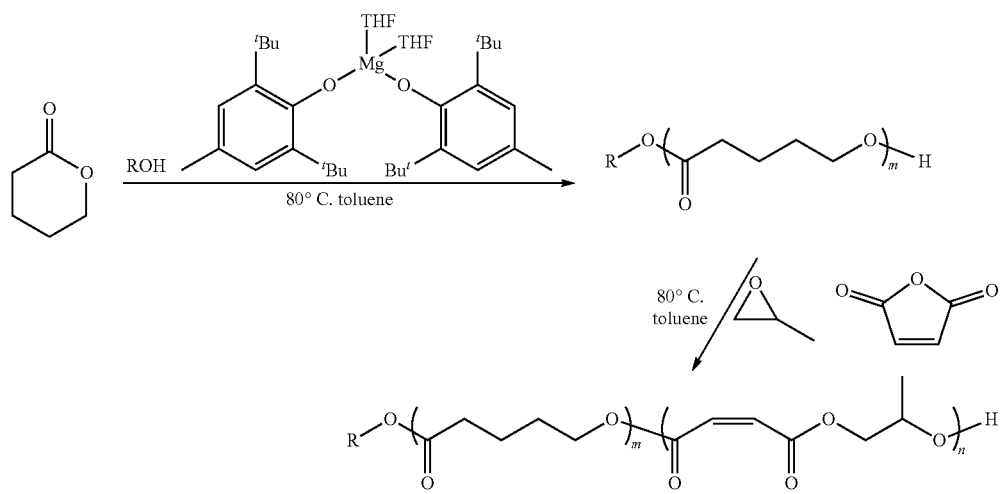

where m and n are each an integer from about 1 to about 500; and R is an end group or end functional group as described above.

In some embodiments, poly(lactone-b-propylene maleate) block copolymer intermediate may be synthesized as shown in Scheme 3, below:

where m and n are each an integer from about 1 to about 500; and R is an end group or end functional group as described above.

In some embodiments, poly(lactone-b-propylene maleate) block copolymer intermediate may be synthesized as shown in Scheme 4, below:

Scheme 3

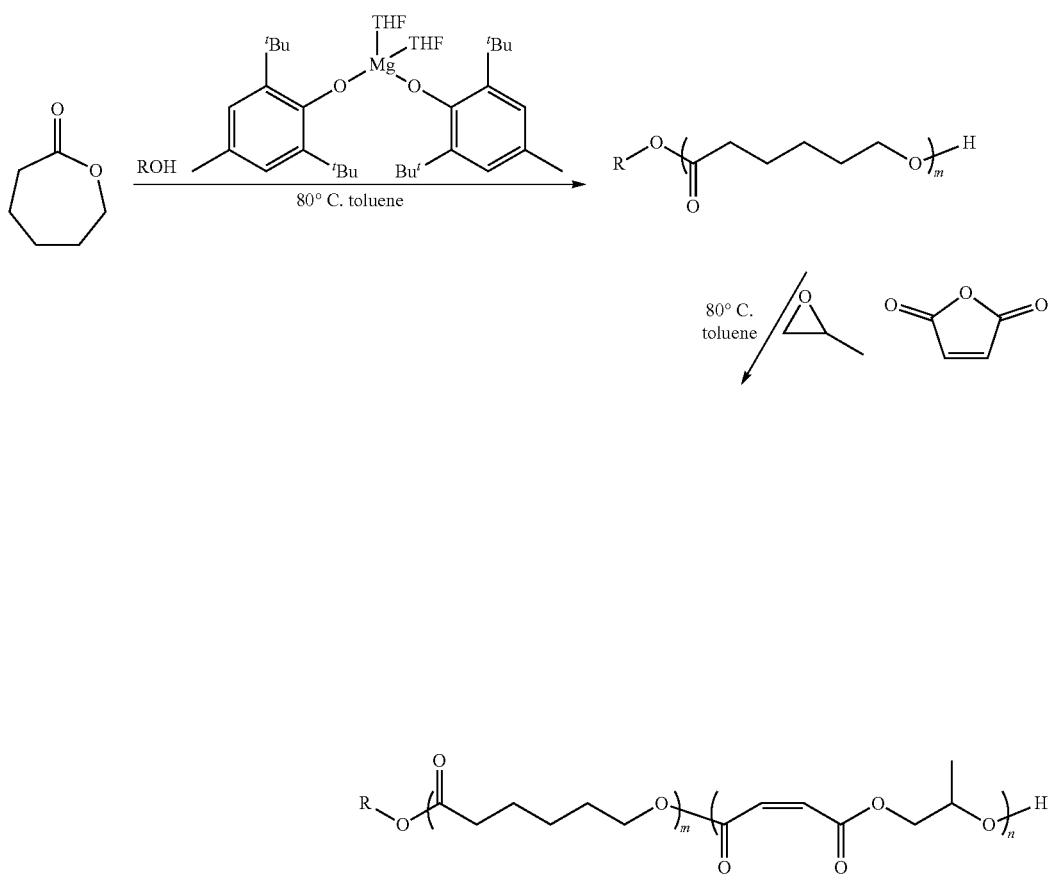

Scheme 4

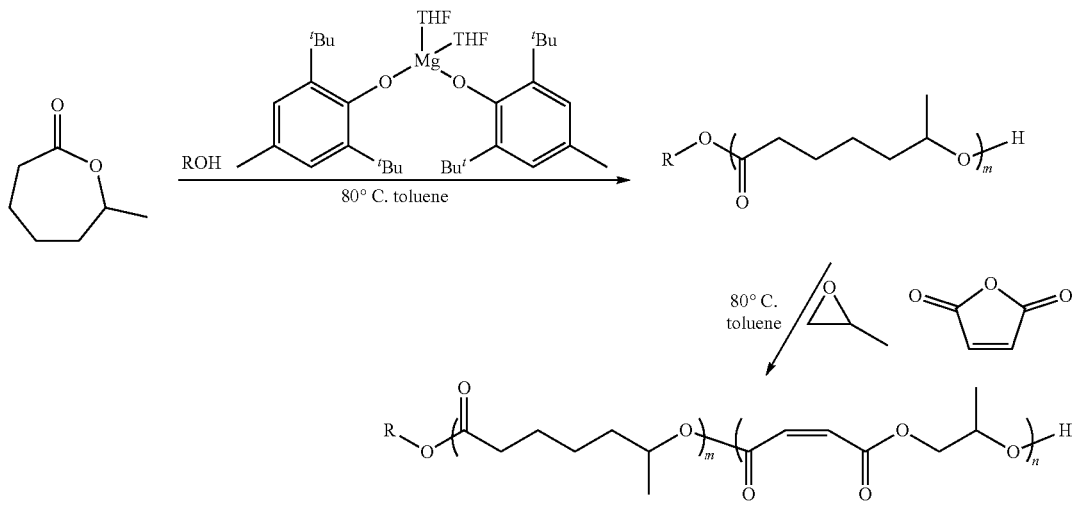

where m and n are each an integer from about 1 to about 500; and R is an end group or end functional group as described above.

In some embodiments, poly(lactone-b-propylene maleate) block copolymer intermediate may be synthesized as shown in Scheme 5, below:

Scheme 5

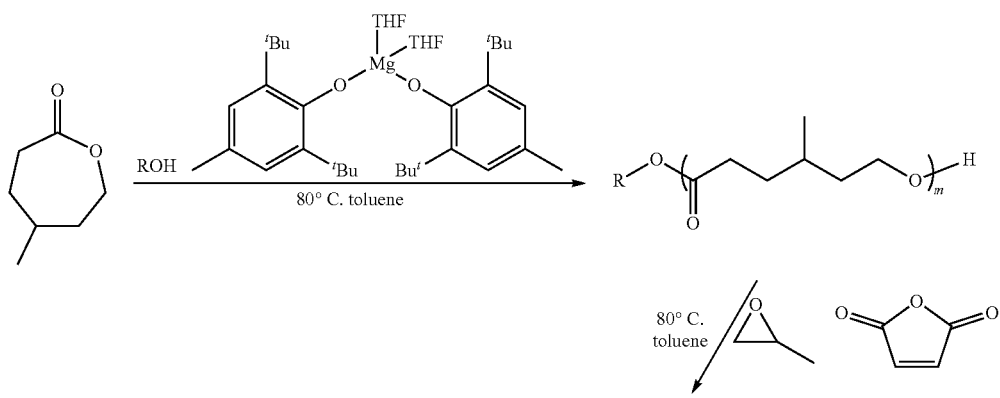

where m and n are each an integer from about 1 to about 500; and R is an end group or end functional group as described above.

In some embodiments, poly(lactone-b-propylene maleate) block copolymer intermediate may be synthesized as shown in Scheme 6, below.

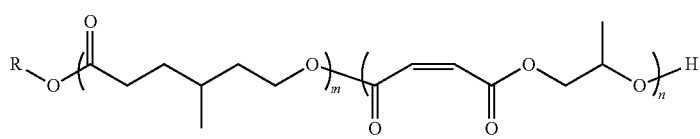

Scheme 6

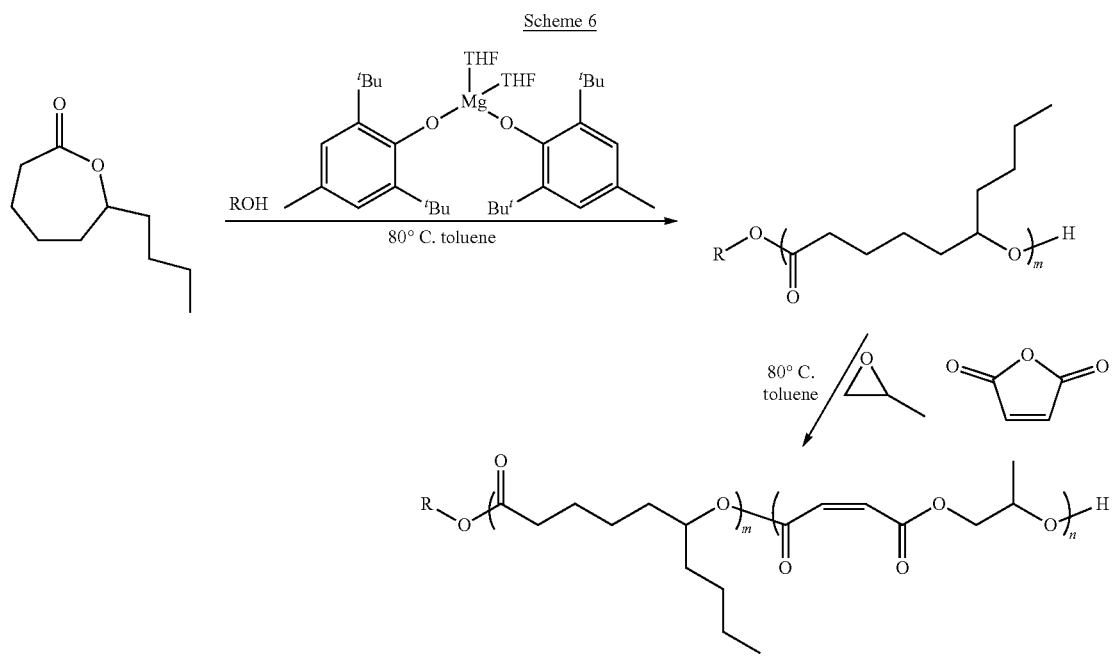

where m and n are each an integer from about 1 to about 500; and R is an end group or end functional group as described above.

In some embodiments, a poly(lactone-b-lactone-b-propylene maleate) triblock polymer intermediate may be synthesized as shown in Scheme 7, below:

where m n and k are each an integer from about 1 to about 500; and R is an end group or end functional group as described above.

In some embodiments, poly(lactone-b-lactone-b-propylene maleate) triblock polymer intermediate may be synthesized as shown in Scheme 8, below:

Scheme 7

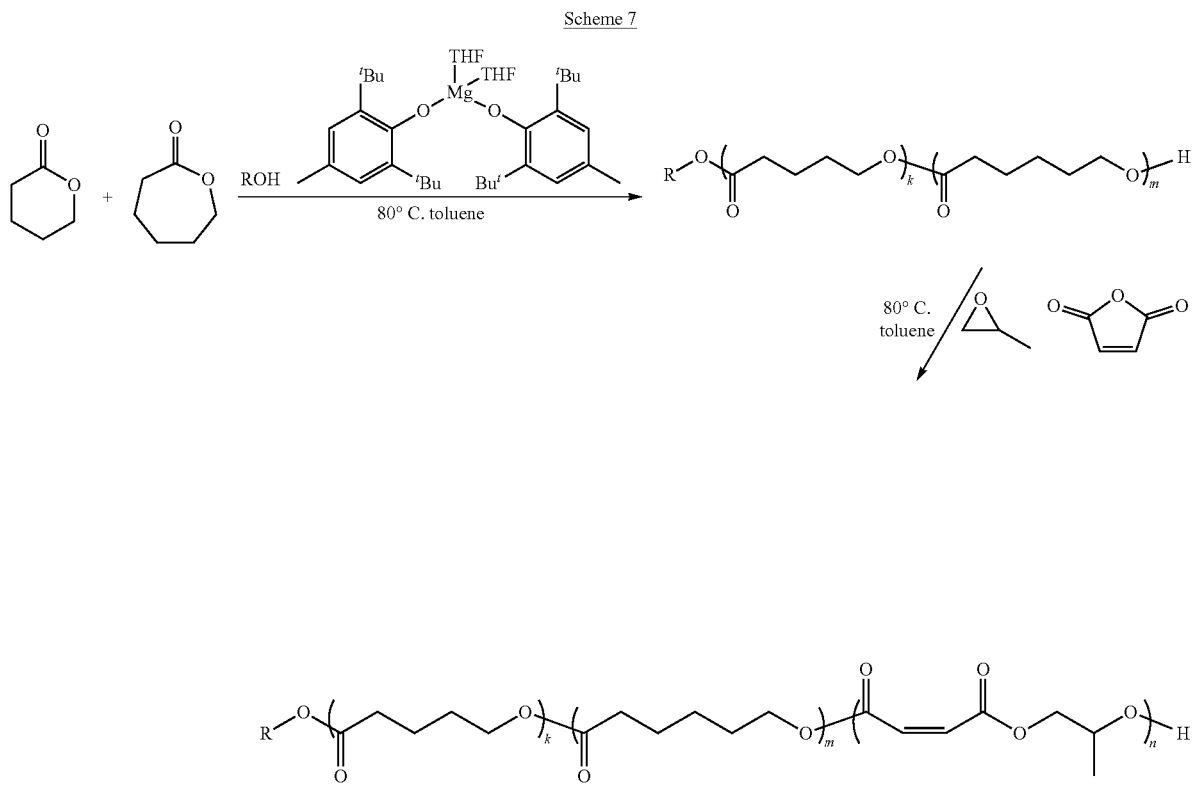

Scheme 8

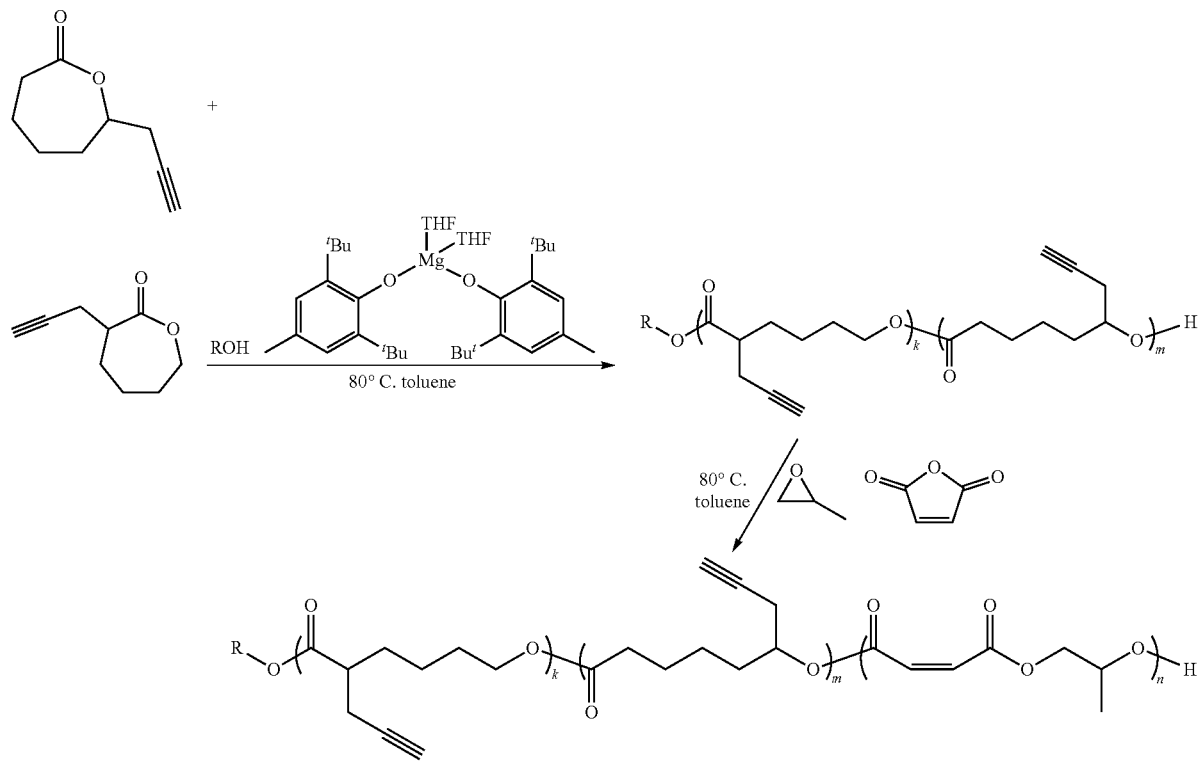

where m n and k are each an integer from about 1 to about 1000; and R is an end group or end functional group as described above.

The poly(lactone-b-propylene maleate) block copolymer and/or poly(lactone-b-lactone-b-propylene maleate)triblock polymer intermediates may be isolated and purified using any known method. In some embodiments, the poly(lactone-b-propylene maleate) block copolymer and/or poly(lactone-b-lactone-b-propylene maleate)triblock polymer intermediates may be recovered by precipitation in excess diethyl ether.

In the third step, the poly(propylene maleate) segment (block) of the poly(lactone-b-propylene maleate) block copolymer and/or poly(lactone-b-lactone-b-propylene maleate)triblock polymer intermediates is isomerized into its trans-isomer (poly(propylene fumarate)) to form a poly (lactone-b-propylene fumarate) block copolymer according to embodiments of the present invention. (See FIG. 1). The term isomerization is used herein to refer to a reaction that converts the cis-isomer (PPM) to the trans-isomer (PPF) form. While the isomerization step does result in some other changes to the polymer, it will be apparent that most general aspects of the end functionalized PPF polymers of embodiments of the present invention, such as the approximate $M_n$, $Đ_M$, and $T_g$ ranges, are determined before the isomerization step. However, it has been found that if even a relatively small amount of PPM polymer chains remain in the polymer, it will adversely affect the ability of the polymer to cross link, rendering it unsuitable for 3D printing and other similar applications. Accordingly, it is important that essentially all of the poly(propylene maleate) be converted to poly(propylene fumarate) if the polymer is to be used for these applications The poly(propylene maleate) segment (block) may be isomerized using any conventional method including, but not limited to the methods described in International Application No. PCT/US2015/061314, published as WO 2016/081587, the disclosure of which is incorporated herein by reference in its entirety. In some embodiments, poly(propylene maleate) segment (block) of these block copolymers may be isomerized as shown in Example 11, below.

In various embodiments, the end functionalized poly (lactone-b-propylene maleate) block copolymer intermediate is placed in a suitable container, such as a round bottom flask, and dissolved in a suitable solvent such as chloroform, tetrahydrofuran (THF), dioxane, diethyl ether, or a combinations thereof, under an inert atmosphere. It is envisioned that whichever solvent is selected can be removed without undue difficulty or expense, and in some embodiments, the solvent is chloroform. Once the PPM intermediate has been dissolved, a catalyst, preferably diethylamine, is added and the container is connected to a condenser and the heated to a reaction temperature of from about 5° C. to about 80° C. In some embodiments, the reaction temperature is from about 5° C. to about 70° C., in other embodiments, from about 5° C. to about 65° C., in other embodiments, from about 5° C. to about 55° C., in other embodiments, from about 20° C. to about 80° C., in other embodiments, from about 40° C. to about 80° C., and in other embodiments, from about 60° C. to about 80° C. In some embodiments, the reaction temperature is from about 55° C. to about 65° C.

In these embodiments, the solution is heated for from about 5 to about 100 hours, from about 5 hours to about 80 hours, in other embodiments, from about 5 hours to about 60 hours, in other embodiments, from about 5 hour to about 50 hours, in other embodiments, from about 5 hours to about 40 hours, in other embodiments, from about 20 hours to about 100 hours, in other embodiments, from about 40 hours to about 100 hours, and in other embodiments, from about 60 hours to about 100 hours to produce the isomerized polymer. (See FIG. 1). In some embodiments, the solution is heated for from about 24 to about 48 hours. When the isomerization reaction is complete, the end functionalized poly(lactone-b-propylene fumarate) block copolymers of the present invention may be isolated and purified by any suitable methods known in the art for that purpose.

While the methods of the present invention have been discussed primarily with reference to poly(lactone-b-propylene fumarate) diblock copolymers, it should be apparent that these methods may be used to form block co polymers having three or more blocks by the sequential addition of lactone monomers (to form an additional lactone block) or propylene oxide/maleic anhydride monomers (to form an additional PPF block) when reagents used to form the prior block have been depleted, as set forth above for the poly (lactone-b-propylene fumarate) diblock copolymers. As with the diblock copolymers discussed above, no additional catalyst or initiating alcohol is required since the hydroxyl group at the end of the previous block functions as the initiator for the next either lactone or the maleic anhydride/propylene oxide ROP, and the magnesium catalyst simply switches to catalyzing ROP for the new block. In some other embodiments, ABA block copolymers may be formed using a di-functional initiating alcohol. In these embodiments, the first block (B) will have two active functional groups and two (A) blocks can be added as described above to form the ABA block copolymer.

In various embodiments, poly(lactone-b-propylene fumarate) block copolymers of the present invention may be used in numerous applications such as 3D printable resins, medical devices, tissue engineering, wound healing, cosmetics, and drug and protein delivery.

EXPERIMENTAL

Figure 3:
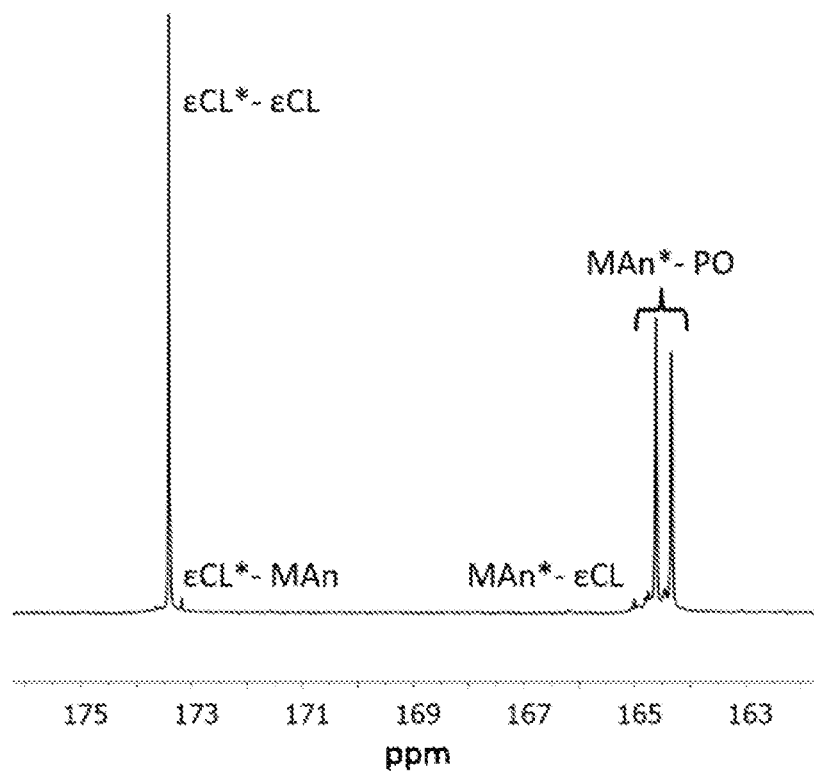
FIG. 3 is a $^{13}$C NMR spectrum showing the carbonyl diad resonance peaks of DP 100 poly(ε-caprolactone-b-propylene maleate) (125 MHz, CDCl$_3$, 303 K).
Figure 4:
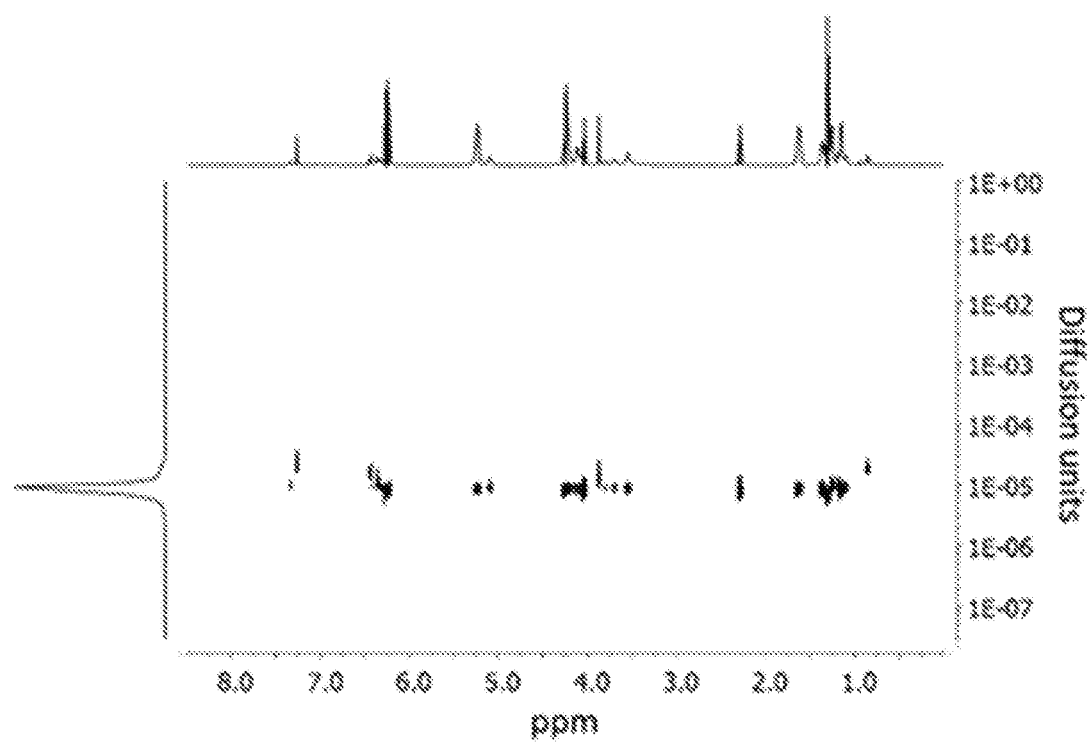
FIG. 4 is a diffusion-ordered NMR spectroscopy ("DOSY" or "DOSY NMR") spectrum (500 MHz, 298 K, CDCl$_3$) for poly(ε-caprolactone-b-propylene maleate).

To further define and reduce embodiments of the present invention to practice, the ROP of εCL and subsequent ROCOP of an equimolar mixture of MAn and PO was investigated. Homopolymerization of εCL using $Mg(BHT)_2(THF)_2$ as a catalyst and benzyl alcohol (BnOH) as a primary alcohol initiator was conducted at a concentration of 2 M in toluene at 80° C. in a sealed, $N_2$ atmosphere. The homopolymerization was allowed to continue for 1 h before a 2 M solution of MAn and PO in toluene was injected into the reaction. The preparation of the MAn and PO solution and its subsequent injection into the PCL reaction solution both occurred in a dry $N_2$ environment in order to maintain the atmosphere of the initial reaction. The polymerization continued for 5 days post injection, after which the polymer was recovered by precipitation in cold hexanes. The monomer conversion of εCL and MAn were determined using $^1H$ NMR spectroscopic analysis of the crude reaction solution taken immediately upon termination of the polymerization. The low vapor pressure and boiling point of PO result in unreliable integration of resonance peaks at the reaction temperature, thus the PO conversion is not reported. $^1H$ NMR spectroscopic analysis of the recovered material showed proton resonances corresponding to PCL, PPM, and the BnOH initiator. No resonances corresponding to the methylene protons of homopolymerized PO were observed ($\delta$=3.3-3.5 ppm), confirming a preference for the alternating copolymerization of MAn and PO afforded with the $Mg(BHT)_2(THF)_2$. (See FIGS. 2-4).

Figure 5:
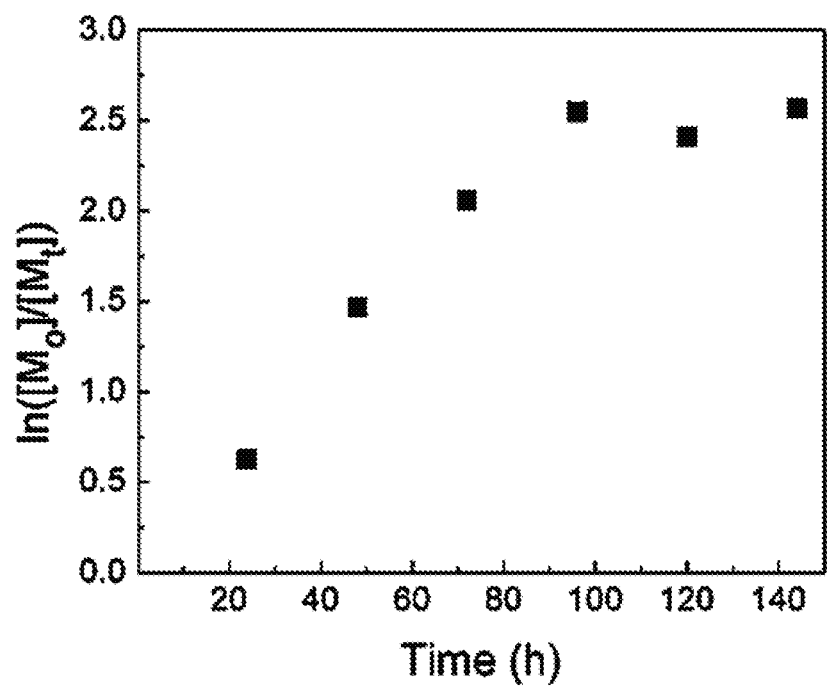
FIG. 5 is a kinetic plot for the copolymerization of maleic anhydride and propylene oxide onto DP 50 poly(ε-caprolactone), conducted at 80° C. in toluene with [εCL]$_0$:[MAn]$_0$:[PO]$_0$:[BnOH]$_0$:[Cat.]$_0$=50:50:50:1:1, total initial monomer concentration=2 M.
Figure 6:
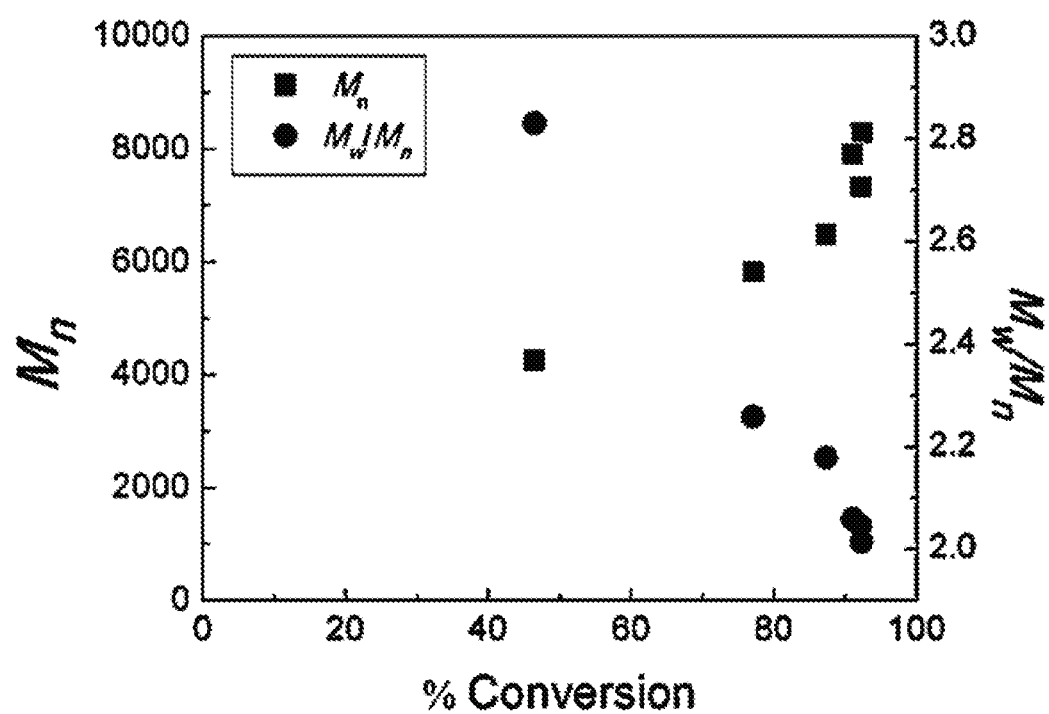
FIG. 6 is a graph showing changes in M$_n$ and Đ$_M$ with increasing MAn conversion for the same copolymerization, determined by SEC against poly(styrene) standards.
Figure 7:
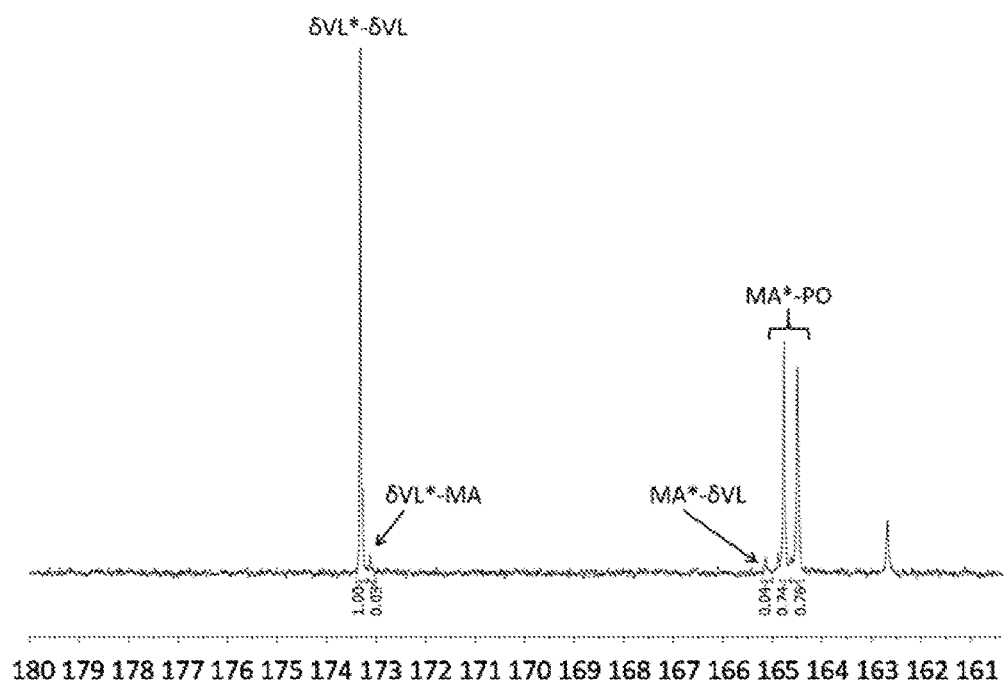
FIG. 7 is a $^{13}$C NMR spectra of the carbonyl diad region of poly(δ-valerolactone-b-propylene maleate) (125 MHz, CDCl$_3$, 303 K).
Figure 8:
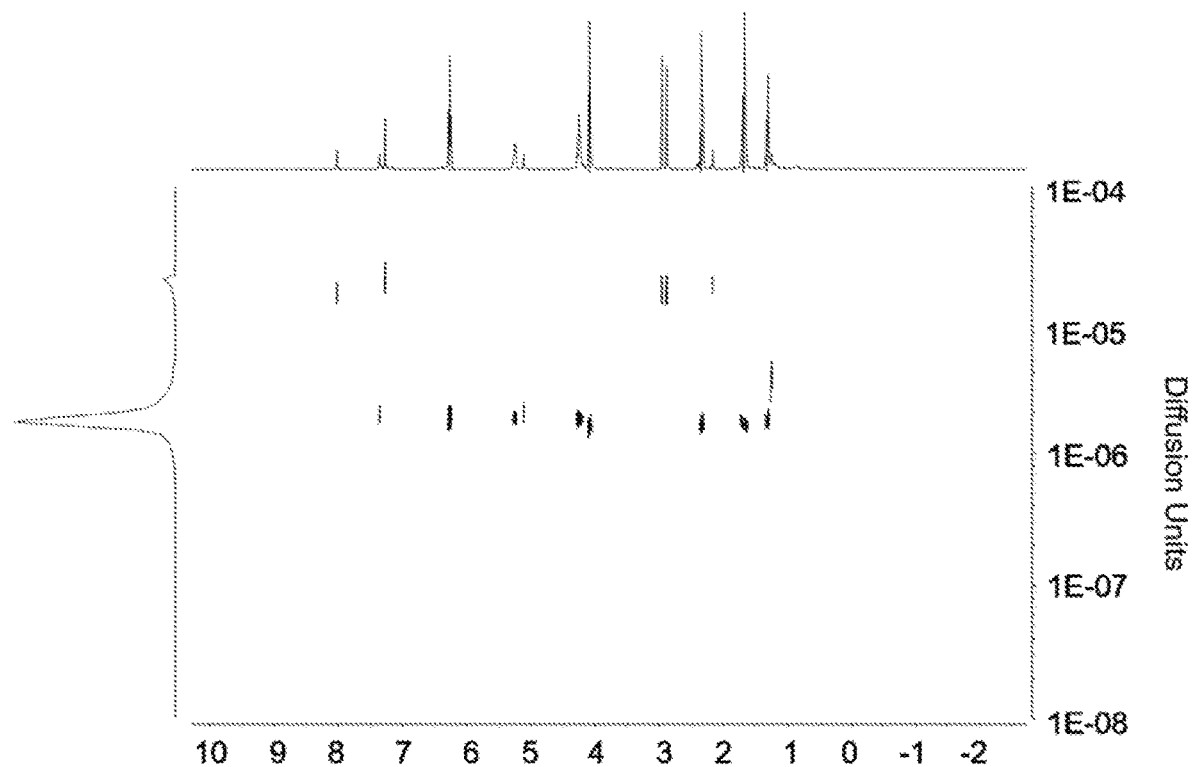
FIG. 8 is a DOSY NMR spectra of poly(δ-valerolactone-b-propylene maleate) (500 MHz, 298 K, CDCl$_3$).
Figure 9:
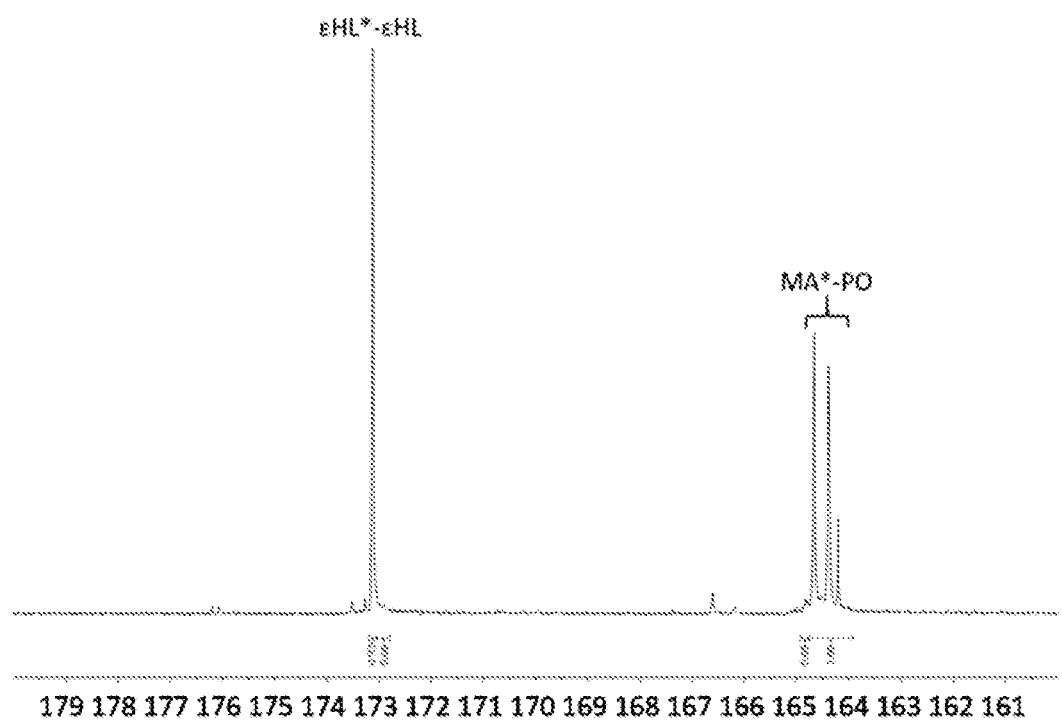
FIG. 9 is a $^{13}$C NMR spectra of the carbonyl diad region of poly(ε-heptalactone-b-propylene maleate) (125 MHz, CDCl$_3$, 303 K).
Figure 10:
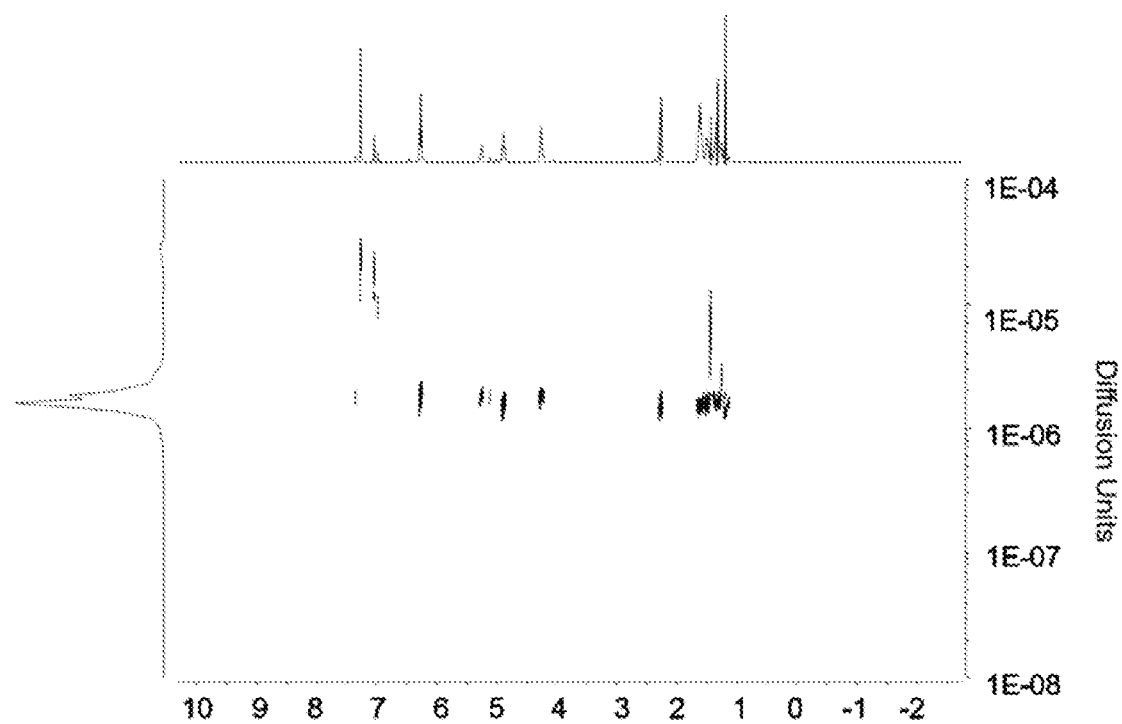
FIG. 10 is a DOSY NMR spectra of poly(ε-heptalactone-b-propylene maleate) (500 MHz, 298 K, CDCl$_3$).
Figure 11:
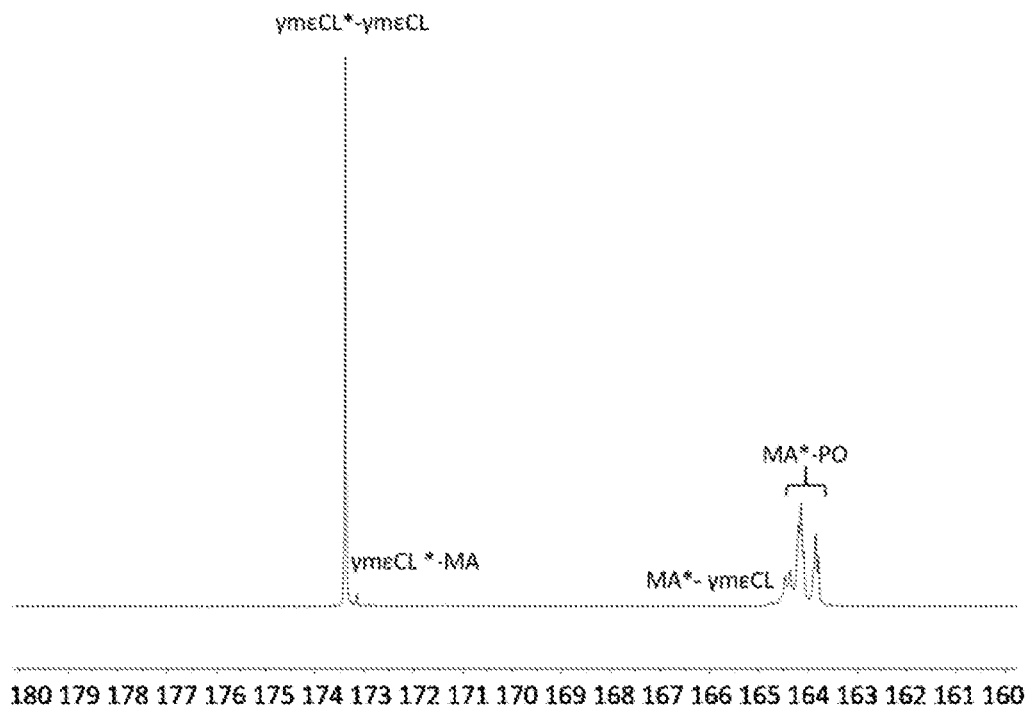
FIG. 11 is a $^{13}$C NMR spectra of the carbonyl diad region of poly(γ-methyl-ε-caprolactone-b-propylene maleate) (125 MHz, CDCl$_3$, 303 K).
Figure 12:
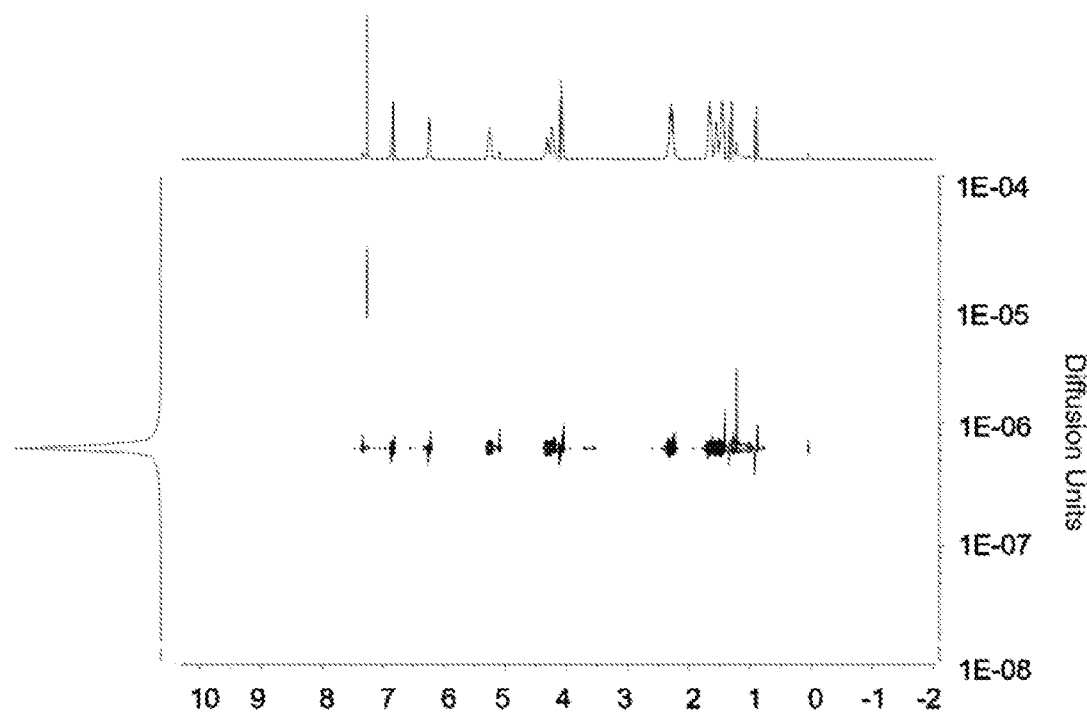
FIG. 12 is a DOSY NMR spectra of poly(γ-methyl-ε-caprolactone-b-propylene maleate) (500 MHz, 298 K, CDCl$_3$).
Figure 13:
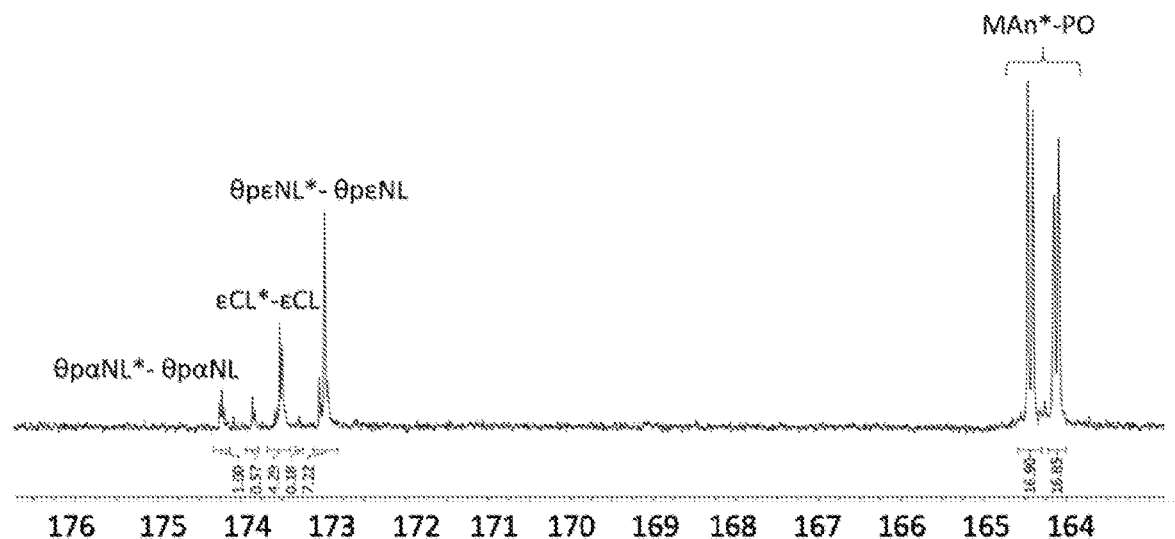
FIG. 13 is a $^{13}$C NMR spectra of the carbonyl diad region of poly(α-propargyl-ε-caprolactone-b-O-propargyl-ε-nonalactone-b-ε-caprolactone-b-propylene fumarate) (125 MHz, CDCl$_3$, 303 K).
Figure 14:
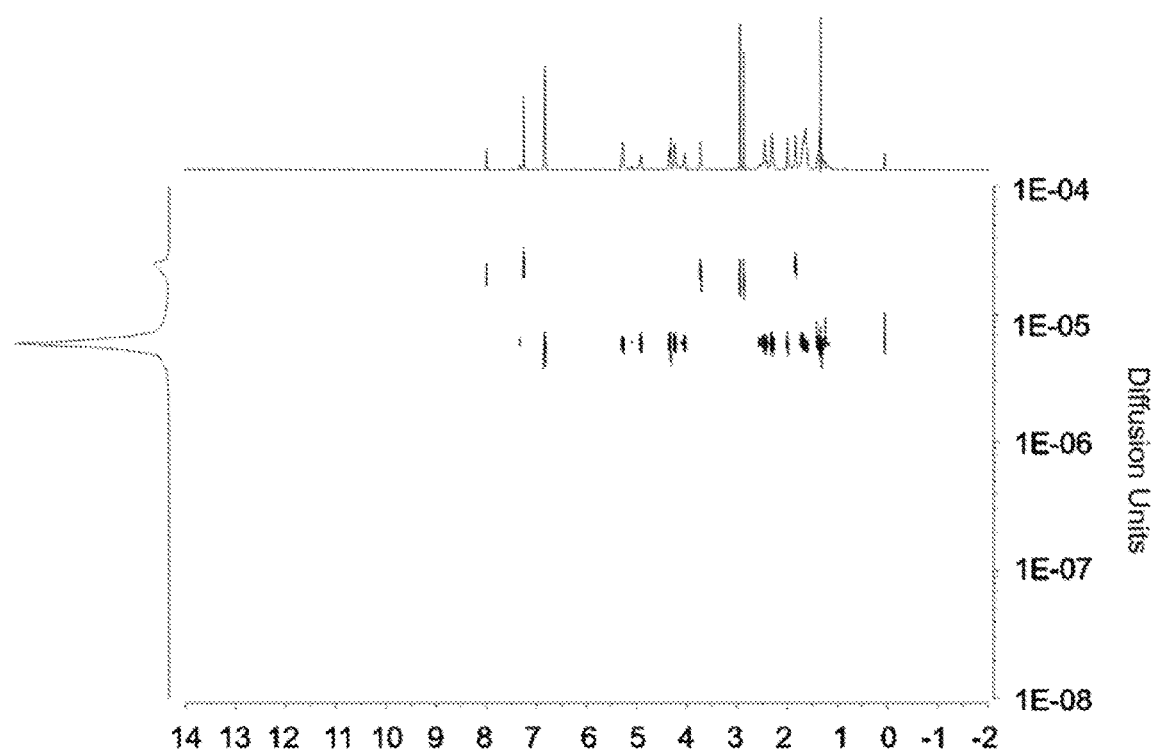
FIG. 14 is a DOSY NMR spectra of poly(α-propargyl-ε-caprolactone-b-O-propargyl-ε-nonalactone-b-ε-caprolactone-b-propylene fumarate) (500 MHz, 298 K, CDCl$_3$).
Figure 15:
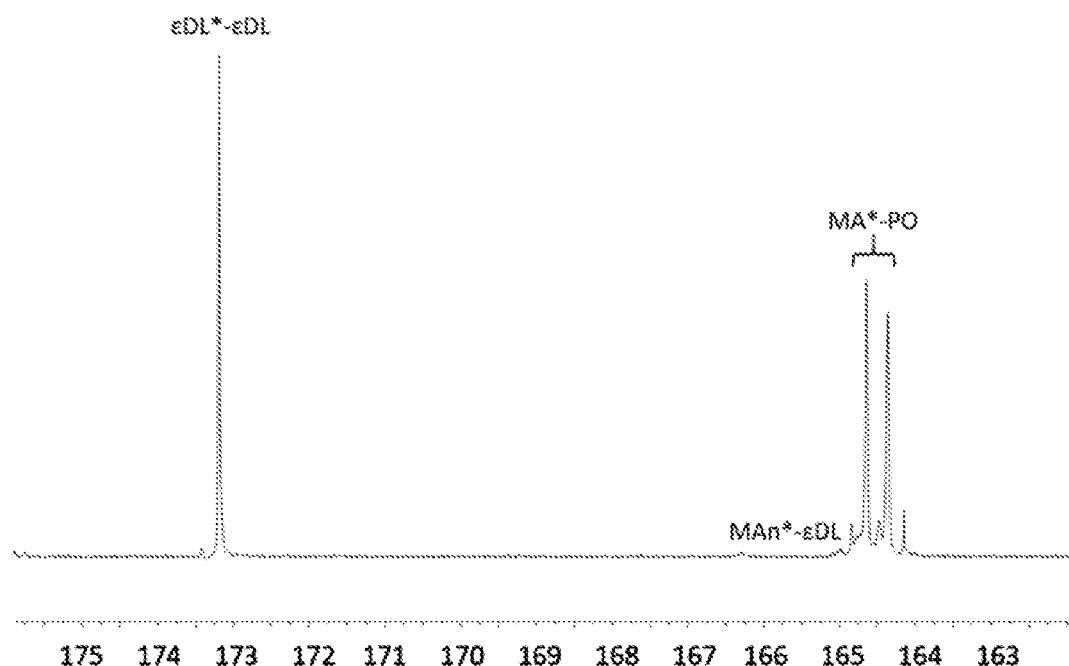
FIG. 15 is a $^{13}$C NMR spectra of the carbonyl diad region of poly(ε-decalactone-b-propylene maleate) (125 MHz, CDCl$_3$, 303 K).
Figure 16:
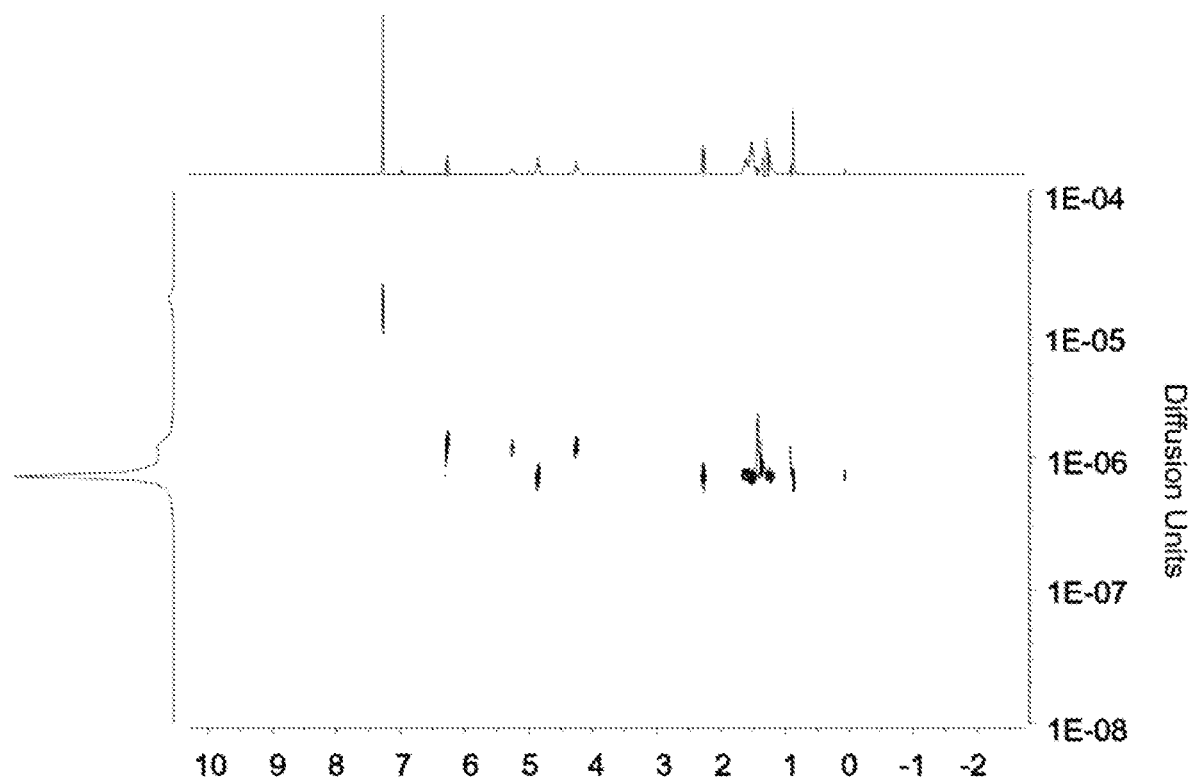
FIG. 16 is a DOSY NMR spectra of poly(ε-decalactone-b-propylene maleate) (500 MHz, 298 K, CDCl$_3$).
Figure 17:
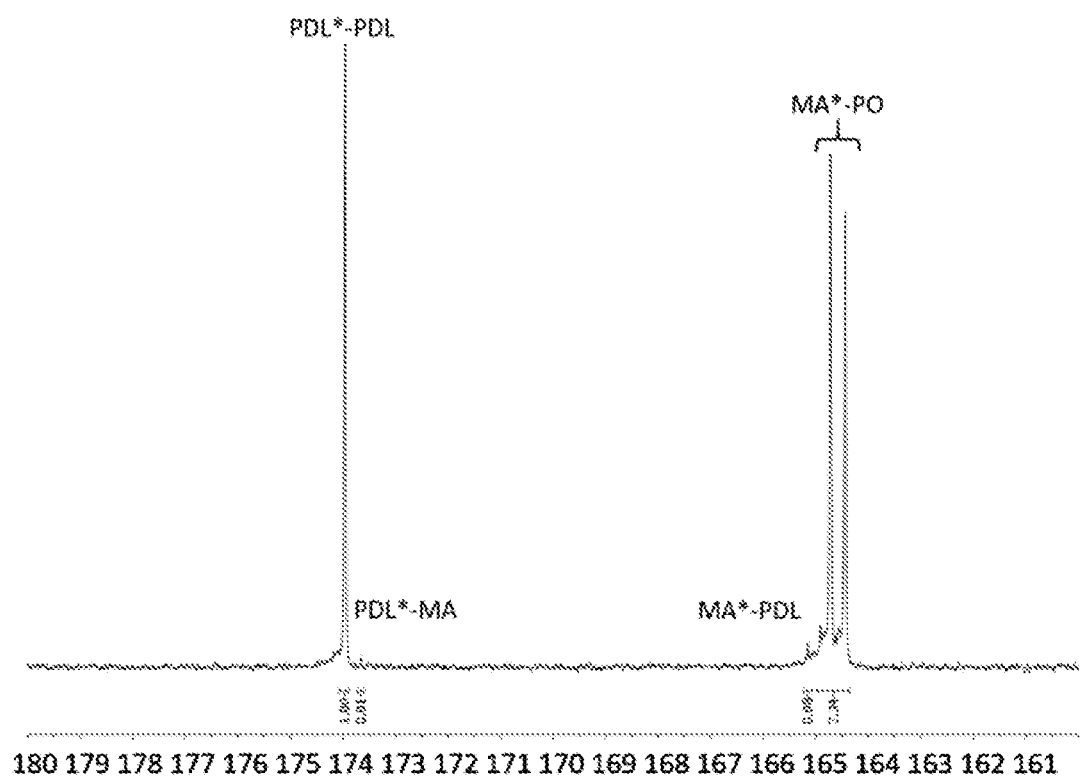
FIG. 17 is a $^{13}$C NMR spectra of the carbonyl diad region of poly(co-pentadecalactone-b-propylene maleate) (125 MHz, CDCl$_3$, 303 K).
Figure 18:
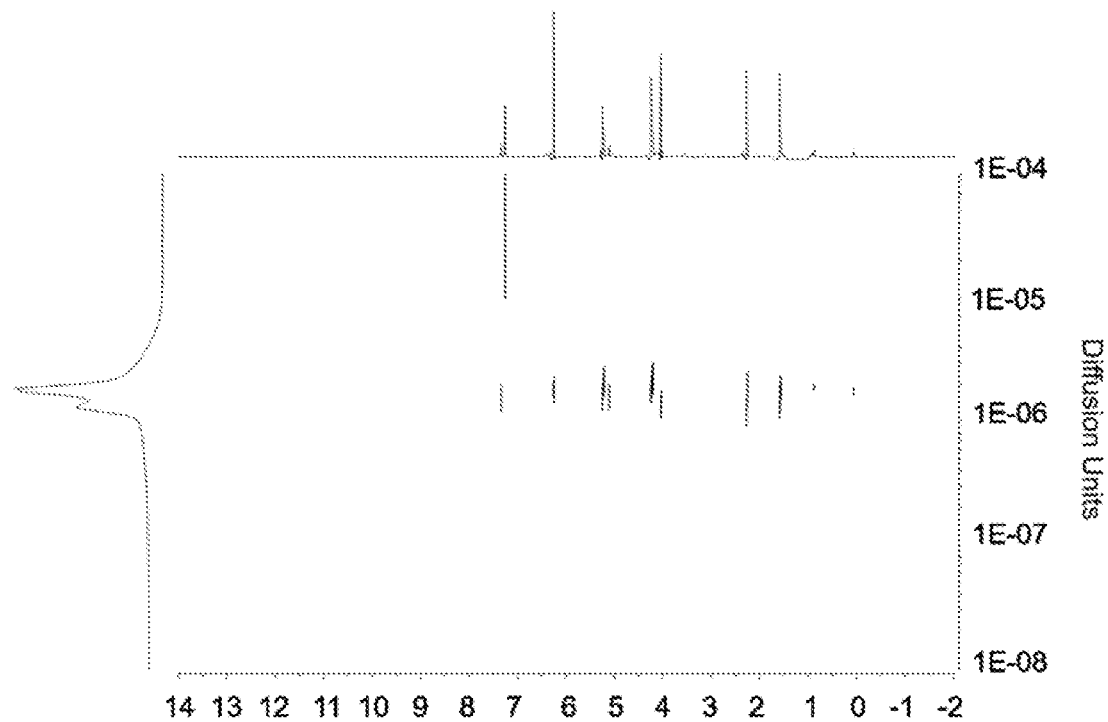
FIG. 18 is a DOSY NMR spectra of poly(ω-pentadecalactone-b-propylene maleate) (500 MHz, 298 K, CDCl$_3$).
Figure 19:
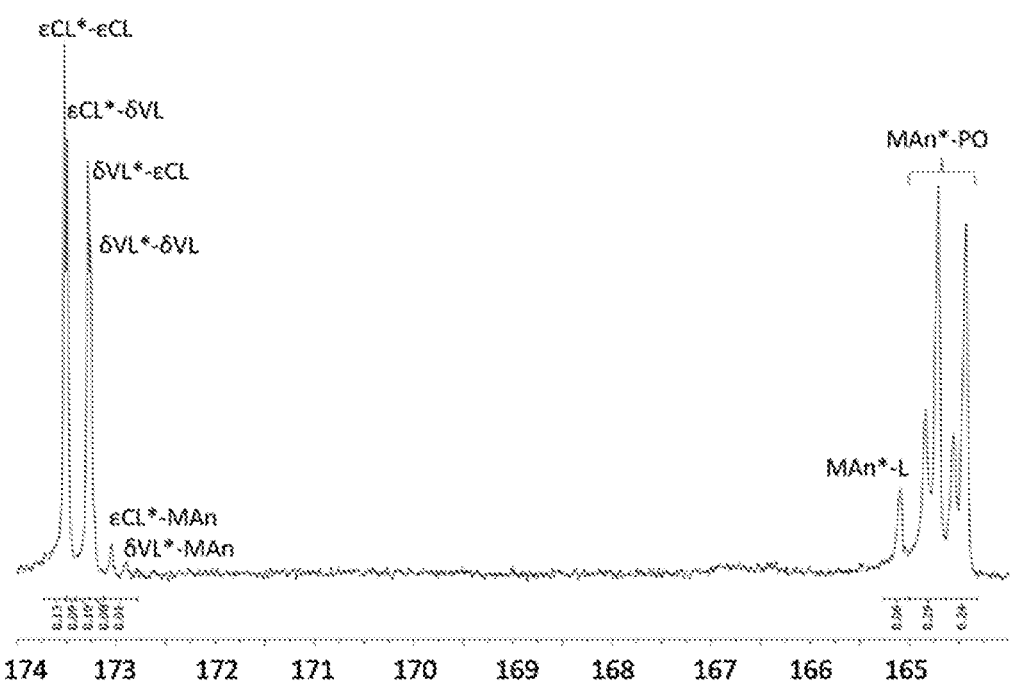
FIG. 19 is a $^{13}$C NMR spectra of the carbonyl diad region of poly(δ-valerolactone-co-ε-caprolactone-b-propylene maleate) (125 MHz, CDCl$_3$, 303 K).
Figure 20:
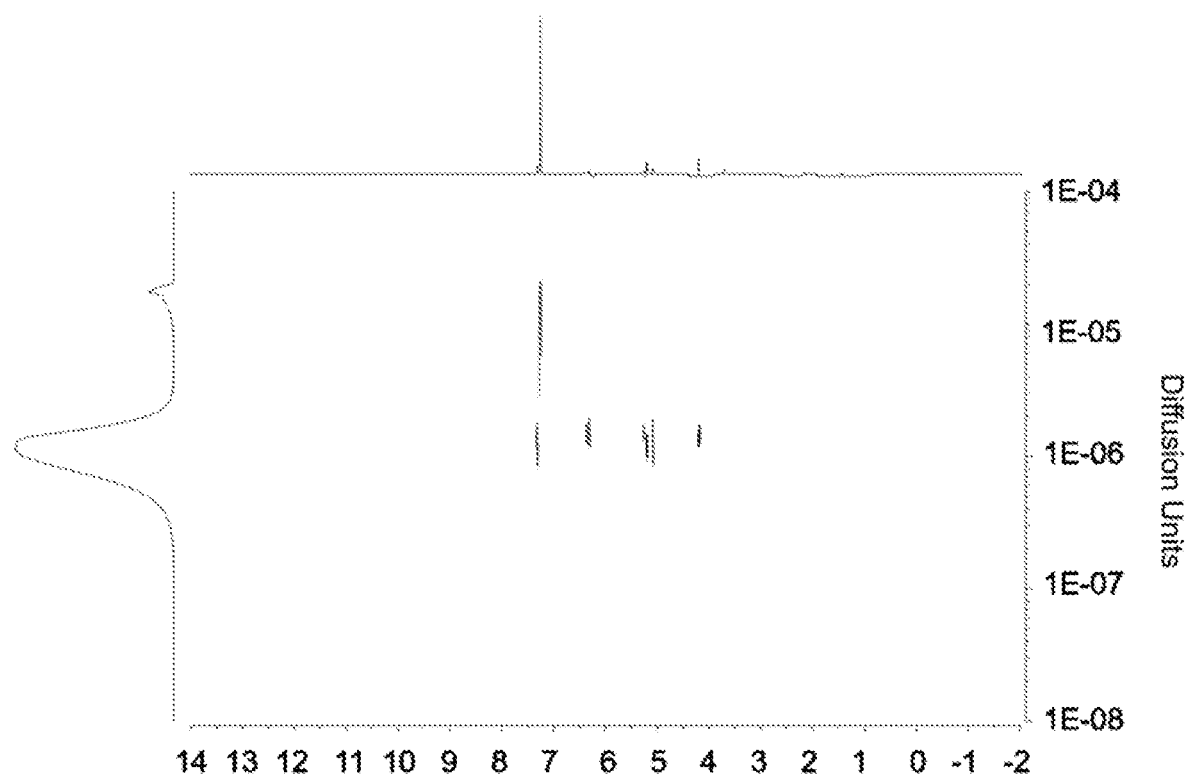
FIG. 20 is a DOSY NMR spectra of poly(δ-valerolactone-co-ε-caprolactone-b-propylene maleate) (500 MHz, 298 K, CDCl$_3$).
Figure 21:
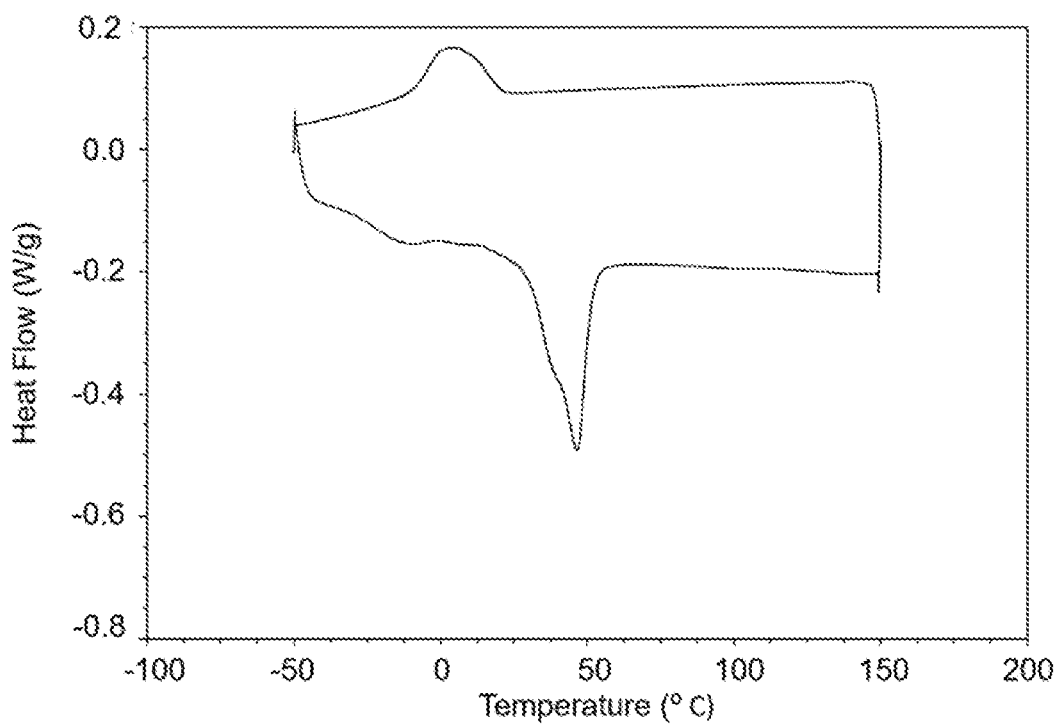
FIG. 21 is a DSC thermogram (second heating curve, between −50 and 150° C.) for poly(δ-valerolactone-b-propylene maleate).
Figure 22:
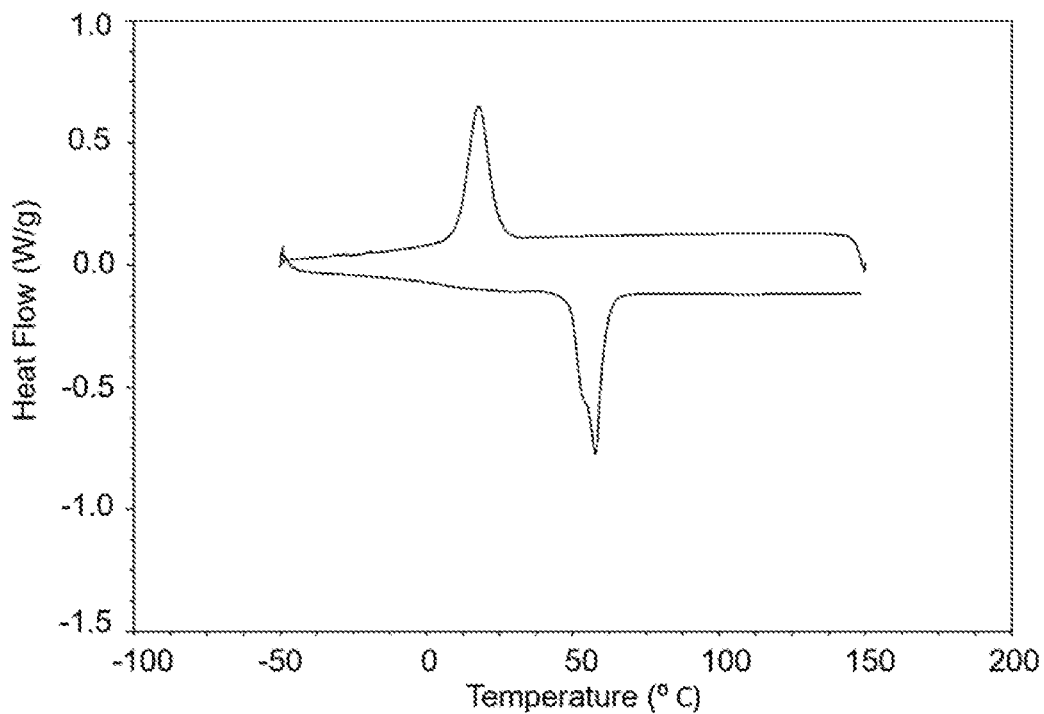
FIG. 22 is a DSC thermogram (second heating curve, between −50 and 150° C.) for poly(ε-caprolactone-b-propylene maleate).
Figure 23:
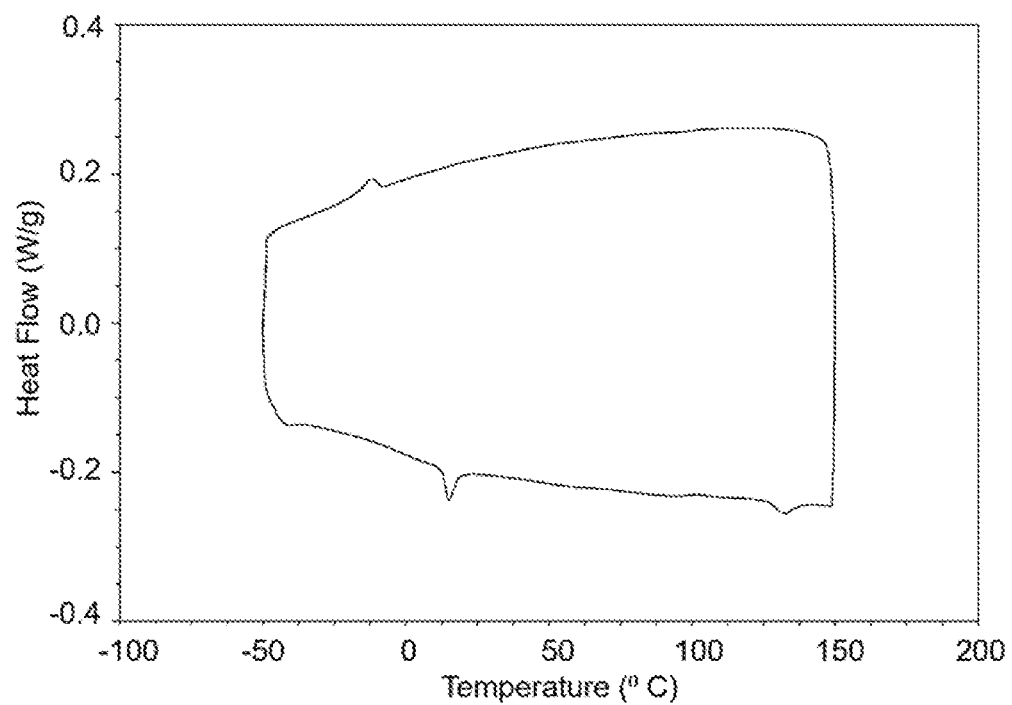
FIG. 23 is a DSC thermograms (second heating curve, between −50 and 150° C.) for poly(ε-heptalactone-b-propylene maleate).
Figure 24:
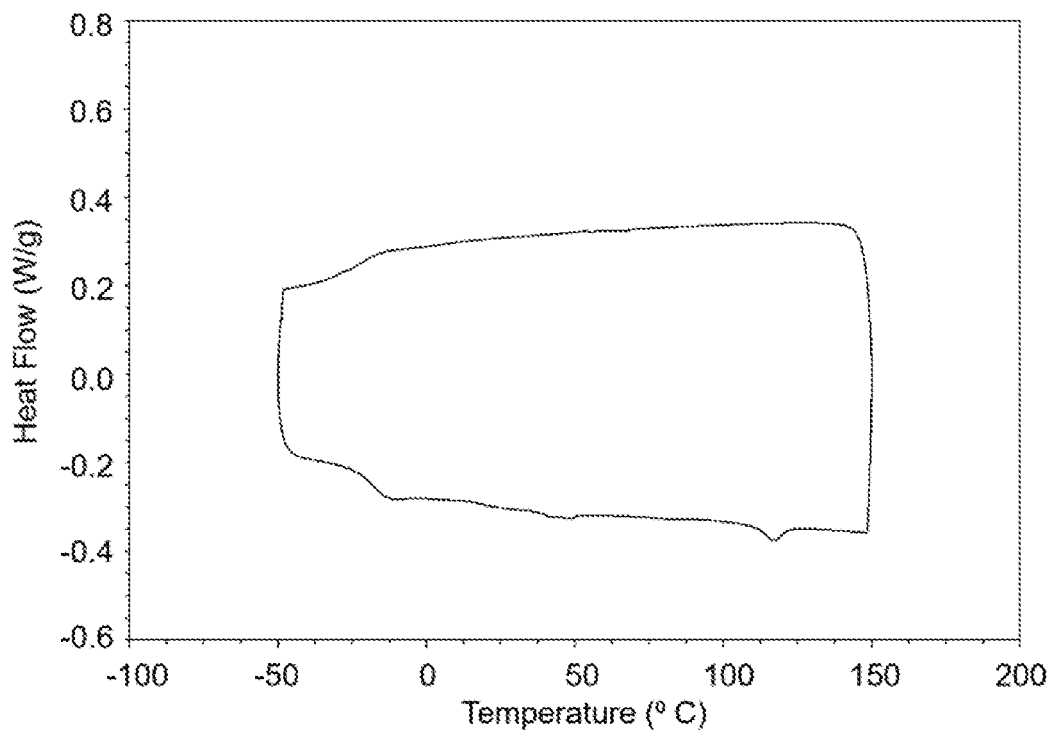
FIG. 24 is a DSC thermograms (second heating curve, between −50 and 150° C.) for poly(γ-methyl-ε-caprolactone-b-propylene maleate).
Figure 25:
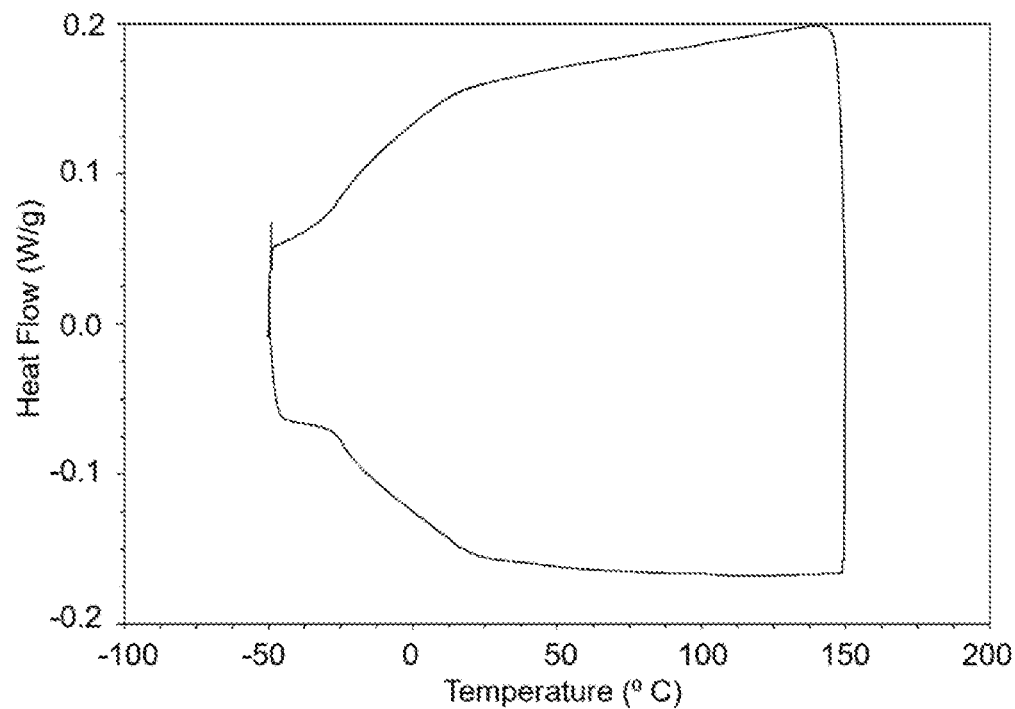
FIG. 25 is a DSC thermograms (second heating curve, between −50 and 150° C.) for poly(α-propargyl-ε-caprolactone-b-O-propargyl-ε-nonalactone-b-ε-caprolactone-b-propylene fumarate).
Figure 26:
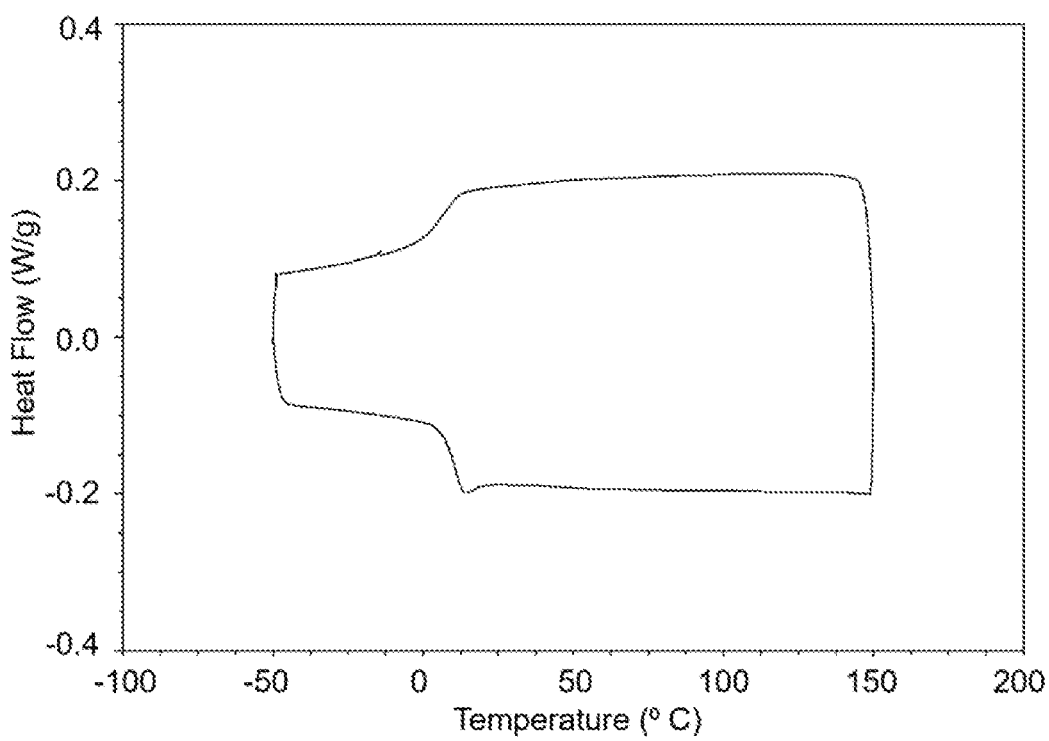
FIG. 26 is a DSC thermograms (second heating curve, between −50 and 150° C.) for poly(ε-decalactone-b-propylene maleate).
Figure 27:
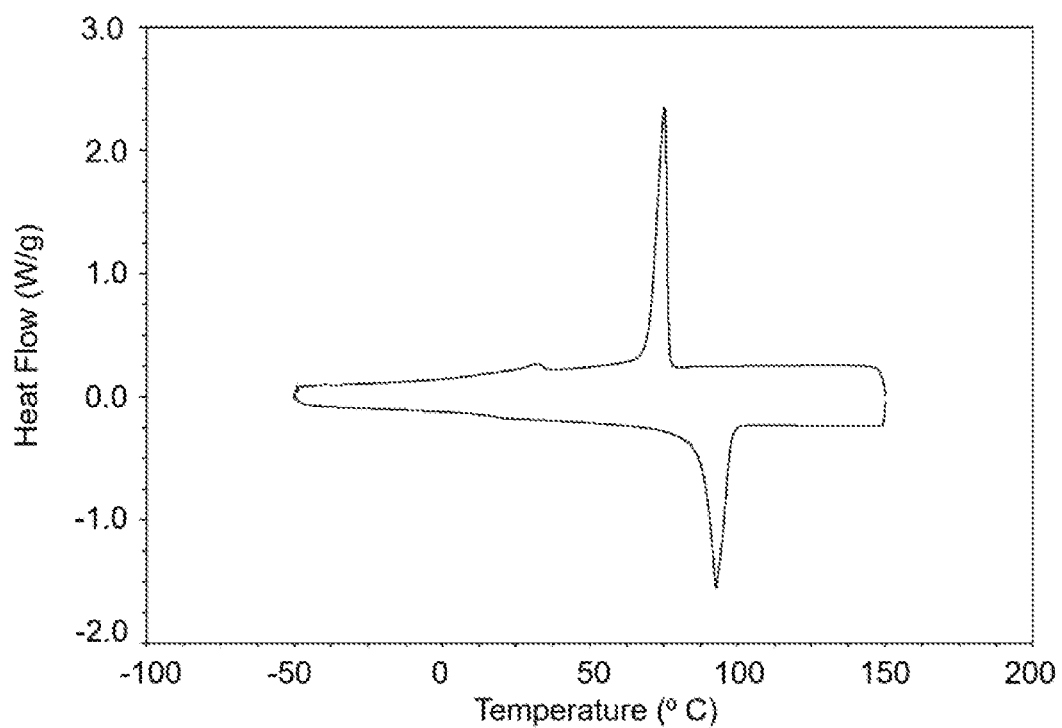
FIG. 27 is a DSC thermograms (second heating curve, between −50 and 150° C.) for poly(ω-pentadecalactone-b-propylene maleate).
Figure 28:
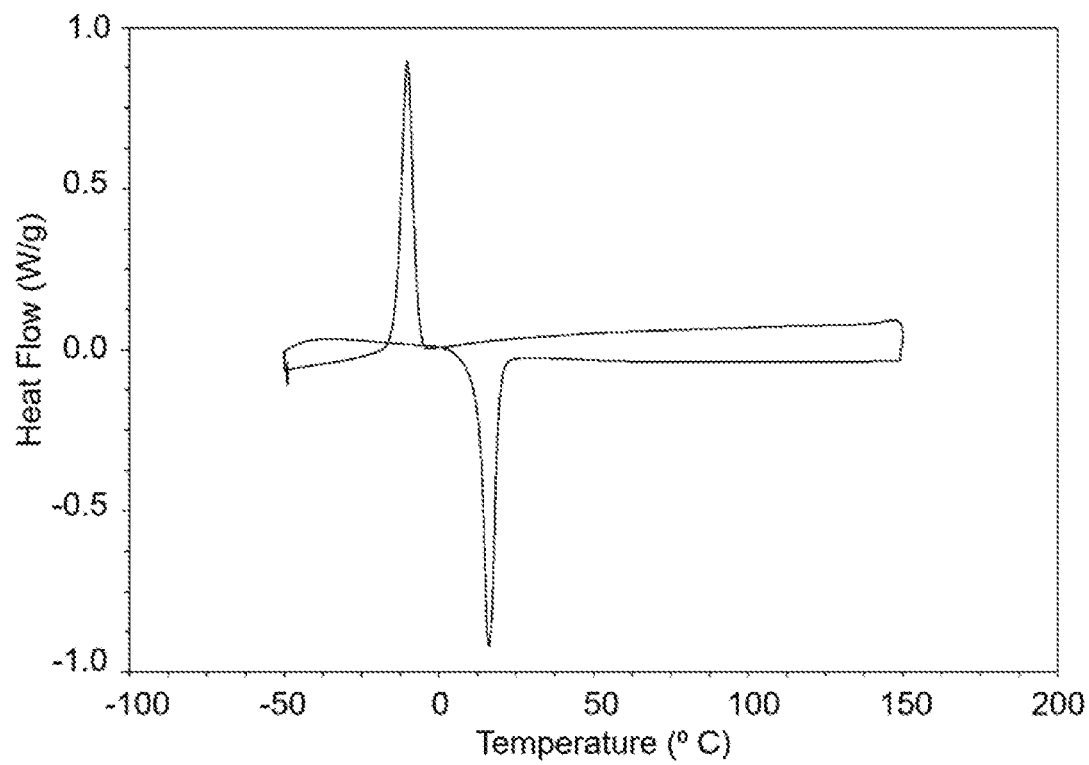
FIG. 28 is a DSC thermograms (second heating curve, between −50° C. and 150° C.) for poly(δ-valerolactone-co-ε-caprolactone-b-propylene maleate).

The structure and regioregularity of the recovered polymer was investigated further using quantitative $^{13}C$ NMR spectroscopy and diffusion-ordered NMR spectroscopy (DOSY). The $^{13}C$ NMR spectra revealed a prominent carbonyl diad resonance at $\delta$=173.4 ppm, corresponding to an εCL carbonyl adjacent to another εCL repeat unit (ECL*-ECL, in which the * denotes the observed carbonyl), and two prominent diad resonance peaks at $\delta$=164.57 ppm and $\delta$=164.19 ppm, which correspond to MAn*-PO. Two very small resonances are also present at $\delta$=173.2 ppm and $\delta$=164.9 ppm, which correspond to εCL*-MAn and MAn*-εCL, respectively. Integration of the carbonyl diad resonance peaks denote a block like sequencing in which one block is a PCL homopolymer and the other block is poly (propylene maleate) (PPM). See, FIG. 3. DOSY NMR spectroscopy revealed only one polymer species, confirming the block like sequencing of poly(ε-caprolactone-block-propylene maleate) (P(CL-b-PM)) as opposed to individual PCL and PPM chains. (See FIGS. 5 and 6).

In order to exploit the alkene functionality present in the PPF block for stereolithographic printing, isomerization of P(CL-b-PM) into poly(ε-caprolactone-b-propylene fumarate) (P(CL-b-PF)) without cleavage or side reactions must occur. Hence, a 0.5 M solution of P(CL-b-PM) in $CHCl_3$ with diethylamine (0.15 molar equivalents per alkene) was heated at reflux overnight, as reported previously. (See, Luo, Y.; Dolder, C. K.; Walker, J. M.; Mishra, R.; Dean, D.; Becker, M. L., Synthesis and Biological Evaluation of Well-Defined Poly(propylene fumarate) Oligomers and Their Use in 3D Printed Scaffolds. *Biomacromolecules* 2016, 17 (2), 690-697, the disclosure of which is incorporated herein in by reference in its entirety.) The diethylamine was removed by washing with 0.5 M sodium phosphate buffer solution prior to solvent removal via rotary evaporation. A complete reduction of the cis-alkene resonance ($\delta$=6.2 ppm) and a new resonance corresponding to the trans-alkene protons ($\delta$=6.7 ppm) was shown using $^1H$ NMR spectroscopy. See, FIG. 1.

The kinetics of the ROCOP of MAn and PO onto an εCL block were studied under the same conditions with a targeted degree of polymerization (DP) of 50 repeat units for both PCL and PPM blocks. Aliquots were withdrawn every 24 h over a period of 6 d after the injection of propylene oxide and maleic anhydride into the polymerization solution. $^1H$ NMR spectroscopic analysis of the crude mixture was used to determine MAn conversion. SEC of the recovered material was used to determine molecular mass and molecular mass distribution ($Đ_M$). Like the ROCOP of MAn and PO from a primary alcohol initiator, the polymerization also follows pseudo-first order kinetics. The rate of monomer conversion is dramatically hindered as a consequence of catalyst affinity with the lactone macroinitiator competing with the propagation of the ROCOP. This is similar to the polymerization kinetics observed in the copolymerization of lactones and macrolactones in previous reports using $Mg(BHT)_2(THF)_2$ as a catalyst. (See, Wilson, J. A.; Hopkins, S. A.; Wright, P. M.; Dove, A. P, 'Immortal' ring-opening polymerization of ω-pentadecalactone by $Mg(BHT)_2(THF)_2$. *Polym. Chem.* 2014, 5 (8), 2691-2694, the disclosure of which is incorporated herein in by reference in its entirety. $Đ_M$ values immediately post injection are indicative of transesterification during the εCL homopolymerization, but decreasing $Đ_M$ and linear molecular mass propagation during the ROCOP provide evidence of a controlled polymerization and preference for the ROCOP of MAn and PO as opposed to further transesterification side reactions. (See Scheme 9, below)

Scheme 9 Polymerization cycles involved in ring-opening block ordered copolymerization

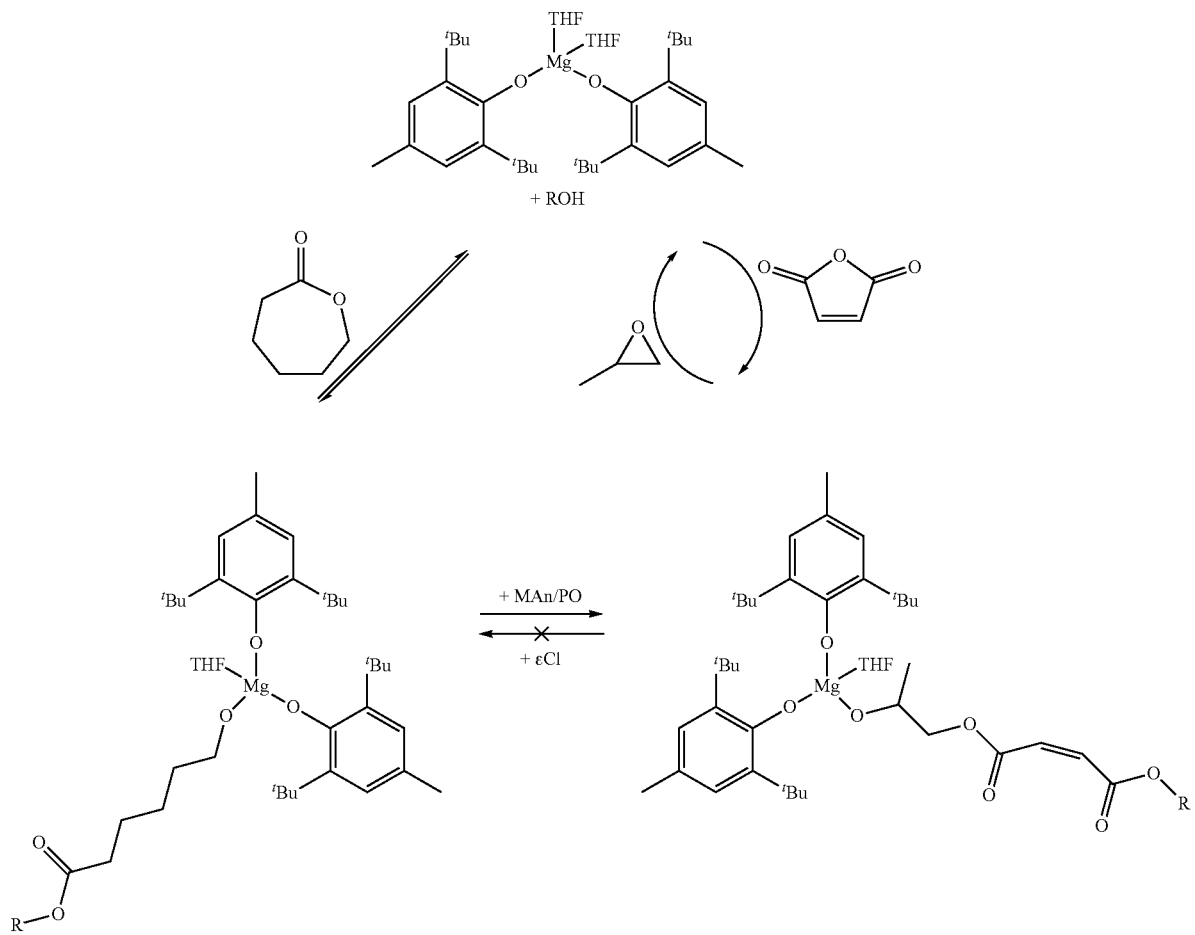

Using the same catalyst, primary alcohol initiator, and temperature stated previously, the copolymerization of εCL, MAn, and PO was also investigated using a single step synthesis and a ROCOP of MAn and PO subsequently followed by injection of εCL. An equimolar ratio of εCL, MAn, and PO was used in both reactions. $^1$H NMR spectroscopic analysis of the recovered material did not reveal εCL incorporation into the polymer produced in either of these reactions. We suspect this to be a consequence of neither the carboxylic acid chain-end of ring-opened MAn nor the secondary alcohol chain-end of ring-opened PO being able to initiate the ring-opening of εCL. As a consequence of this selectivity, copolymers produced by the sequential lactone ROP and MAn and PO ROCOP should contain no gradation region between the blocks. This also suggests a high degree of regioregularity in the copolymerization of MAn and PO catalyzed by Mg(BHT)$_2$(THF)$_2$.

In order to further explore the viability of Mg(BHT)$_2$(THF)$_2$ as a catalyst for the ROP "switch" ROCOP of polyesters with MAn and PO, syntheses using a smaller lactone (δ-valerolactone (δVL)), alkyl-substituted lactones (γ-methyl-ε-caprolactone (γmεCL), ε-heptalactone (εHL) and ε-decalactone (εDL)), macrolactones (PDL), and functional lactones (an isomeric mixture of θ-propargyl-ε-nonalactone (θpεNL) and α-propargyl-ε-caprolactone (αpεCL)) were investigated. (See Scheme 10, below).

Scheme 10
Lactone monomers used for copolymerization with poly(propylene fumarate)

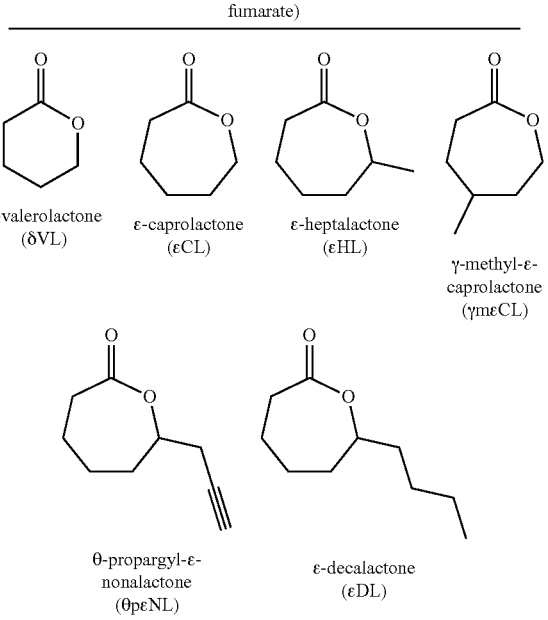

δ-valerolactone (δVL)

ε-caprolactone (εCL)

ε-heptalactone (εHL)

γ-methyl-ε-caprolactone (γmεCL)

θ-propargyl-ε-nonalactone (θpεNL)

ε-decalactone (εDL)

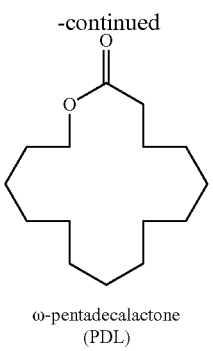

ω-pentadecalactone
(PDL)

With the exception of δVL, γmεCL and PDL all lactones were homopolymerized for 24 h at 80° C. at a 2 M concentration in toluene, utilizing Mg(BHT)$_2$(THF)$_2$ as a catalyst and BnOH as a primary alcohol initiator in a sealed N$_2$ atmosphere. δVL, γmεCL, and PDL were homopolymerized using the same conditions for 1 h, 1 h, and 8 h respectively. After the homopolymerization, a dry, 2 M solution of MAn and PO in toluene was injected into each reaction. $^1$H NMR spectroscopy was conducted on the crude reaction mixture 5 days after the injection of PO and MAn in order to determine monomer conversion prior to precipitation of the resultant polymer in hexanes. The results of these experiments are summarized in Table 1, below.

tions as the previous polymerization. $^1$H NMR spectroscopy confirmed the presence of each monomer species and quantitative $^{13}$C NMR spectroscopy once again suggested block sequencing of θpεNL, αpεCL, and εCL in addition to the alternating block of MAn and PO. Though the exact mechanism behind this sequencing is beyond the scope of this disclosure and not necessary to understand and practice the invention, the stereoselectivity and isomeric selectivity seen with these monomers in this polymerization is worth noting, as all previous polymerizations of εCL with other ε-substituted ε-lactones (εSεLs) have been reported to have random sequencing. This may be a consequence of the propargyl group readily co-ordinating with the catalyst leading to preferential polymerization compared to εCL and ultimately producing the first example of a one-step εCL block copolymer with another lactone.

The ROCOP synthesis of δVL and εCL followed by the ROCOP of MAn and PO was also explored. Once again utilizing Mg(BHT)$_2$(THF)$_2$ as a catalyst and BnOH as an initiator, δVL and εCL were copolymerized for 24 h at 80° C. at a 2 M concentration in toluene. $^1$H NMR spectroscopy revealed equal incorporation of δVL and εCL into the polymer chain in addition to the incorporation of MAn and PO. Analysis of the carbonyl diad resonance peaks by $^{13}$C NMR spectroscopy showed block like sequencing with random incorporation of δVL and εCL into one block and alternating MAn and PO incorporation into the second

TABLE 1

Properties of PPF based block copolymers produced using Mg(BHT)$_2$(THF)$_2$ as a catalyst with varied lactone monomer feed and targeted DPs

| Lactone monomer (L) | Target [L]:[PM] | Time (h) | Lactone conv. (%)$^a$ | MAn conv. (%)$^a$ | Actual [L]:[PM]$^b$ | M$_n$ (kDa)$^b$ NMR | M$_n$ (kDa)$^c$ SEC | M$_w$ (kDa)$^c$ SEC | Đ$_M$$^c$ SEC | T$_m$ (° C.)$^d$ DSC | T$_c$ (° C.)$^d$ DSC | T$_g$ (° C.)$^d$ DSC |
|---|---|---|---|---|---|---|---|---|---|---|---|---|
| δVL | [50]:[50] | 1 | 94 | 84 | [42]:[33] | 9.4 | 6.5 | 8.3 | 1.85 | 47 | 4 | — |
| εCL | [50]:[50] | 1 | 85 | 90 | [46]:[41] | 11.6 | 7.0 | 15.0 | 2.14 | 58 | 18 | — |
| εHL | [50]:[50] | 24 | 95 | 90 | [48]:[42] | 12.7 | 4.5 | 9.8 | 1.80 | 15 | −12 | — |
| γmεCL | [50]:[50] | 1 | 94 | 81 | [46]:[47] | 13.2 | 4.5 | 9.2 | 2.02 | — | — | −18 |
| θpεNL | [50]:[50] | 24 | 89 | 84 | [35]:[38] | 11.3 | 7.4 | 14.6 | 1.97 | — | — | −11 |
| εDL | [50]:[50] | 8 | 90 | 81 | [40]:[29] | 11.3 | 2.6 | 4.0 | 1.56 | — | — | 11 |
| ωPDL | [50]:[50] | 24 | 82 | 78 | [30]:[25] | 11.1 | 5.5 | 7.8 | 1.41 | 93 | 75 | — |
| δVL/εCL | [50]:[50] | 24 | 92 | 72 | [50]:[29] | 9.9 | 1.6 | 3.2 | 1.97 | 16 | −10 | — |

$^a$Determined by $^1$H NMR spectroscopic analysis of the crude reaction mixture and comparison of the monomer proton resonance to the corresponding polymer proton resonance (δ = 6.26 ppm).
$^b$Determined by end-group analysis by $^1$H NMR spectroscopic analysis of the crude reaction mixture.
$^c$Determined by SEC in THF against poly(styrene) standards.
$^d$Determined by differential scanning calorimetry.

Both $^{13}$C and DOSY NMR spectroscopy confirmed the presence of a polylactone block and a PPM block in all recovered products. (See FIGS. 3, 4 and 7-20). $^1$H NMR spectroscopy revealed that the PPM blocks did not reach the target DP, which is likely a consequence of hindered kinetics onto a lactone-based macroinitiator resulting in incomplete monomer conversion. However, no polymerizations were observed to reach less than 70% conversion of maleic anhydride.

Interestingly, integration of the carbonyl diad resonance peaks in the quantitative $^{13}$C NMR spectra of the polymer containing θpεNL revealed a block like sequencing of the θpεNL, αpεCL, and a small amount of εCL that was produced during monomer synthesis, in addition to the separate PM block. In order to confirm this effect, a polymer targeting 25 propargyl substituted lactone units, 25 εCL units, and 50 PM units was synthesized by polymerizing an isomeric mixture of θpεNL and αpεCL with εCL and subsequently injecting MAn and PO using the same condiblock. DOSY NMR spectroscopy confirmed the presence of a single diffusing polymer species.

Thermal analysis using differential scanning calorimetry (DSC) revealed a broad range of properties. (See FIGS. 21-28). As expected, polymers containing aliphatic lactone blocks had melting temperatures above room temperature and crystallization temperatures above 0° C., both of which increased with increasing carbon chain length in the backbone. The exception to this is P(δVL-co-εCL-b-PM) which had a melting temperature (T$_m$) below room temperature and a crystallization temperature (T$_C$) below 0° C. This suppression is a consequence of the random distribution of esters along the backbone disrupting the regular packing structure seen in poly(δ-valerolactone) (PVL) or PCL chains. This is an unexpected result as most random lactone copolymers have been observed to produce T$_m$s and T$_c$s between those of the corresponding lactone homopolymers, based on molar ratio. P(εHL-b-PM) had thermal characteristics between those containing aliphatic lactone blocks and those containing substituted lactone blocks, with a melting temperature just below room temperature and a crystallization temperature below 0° C.

As expected, P(γmεCL-b-PM), P(θpεNL-b-αpεCL-b-εCL-b-PM), and P(εDL-b-PM) showed no crystalline behavior and were all viscous liquids at room temperature, as a consequence of the pendent side chains disrupting any crystallization of the main chain. (See FIGS. 24, 25, 26). Interestingly, while γmεCL and εHL are isomeric εSεLs, the placement of the methyl-substitution has a large effect on the crystallization of the copolymer to the extent that all crystallization is disrupted in γmεCL but not εHL. The size of the substitution is also observed to effect the $T_g$ of the amorphous copolymers, with longer chain lengths showing an increased $T_g$. This is likely a consequence of increased flexibility in the longer chains of εDL allowing better chain packing rather than the short inflexible methyl substitutions of γmεCL creating pockets of poor packing in the network.

Figure 29:
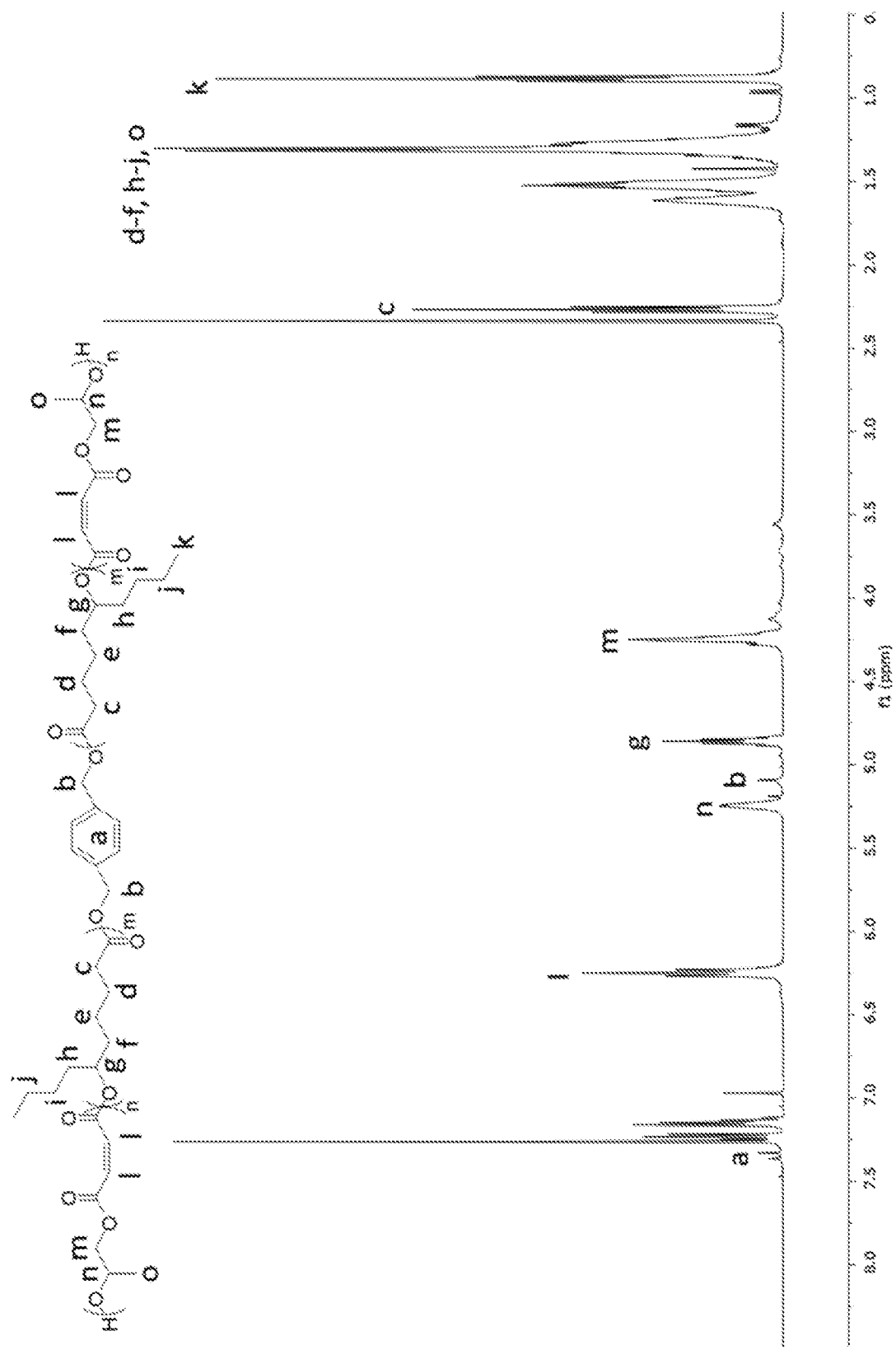
FIG. 29 is a $^1$H NMR spectra of poly(propylene maleate-b-ε-decalactone-b-propylene maleate) (300 MHz, CDCl$_3$, 303 K).
Figure 30:
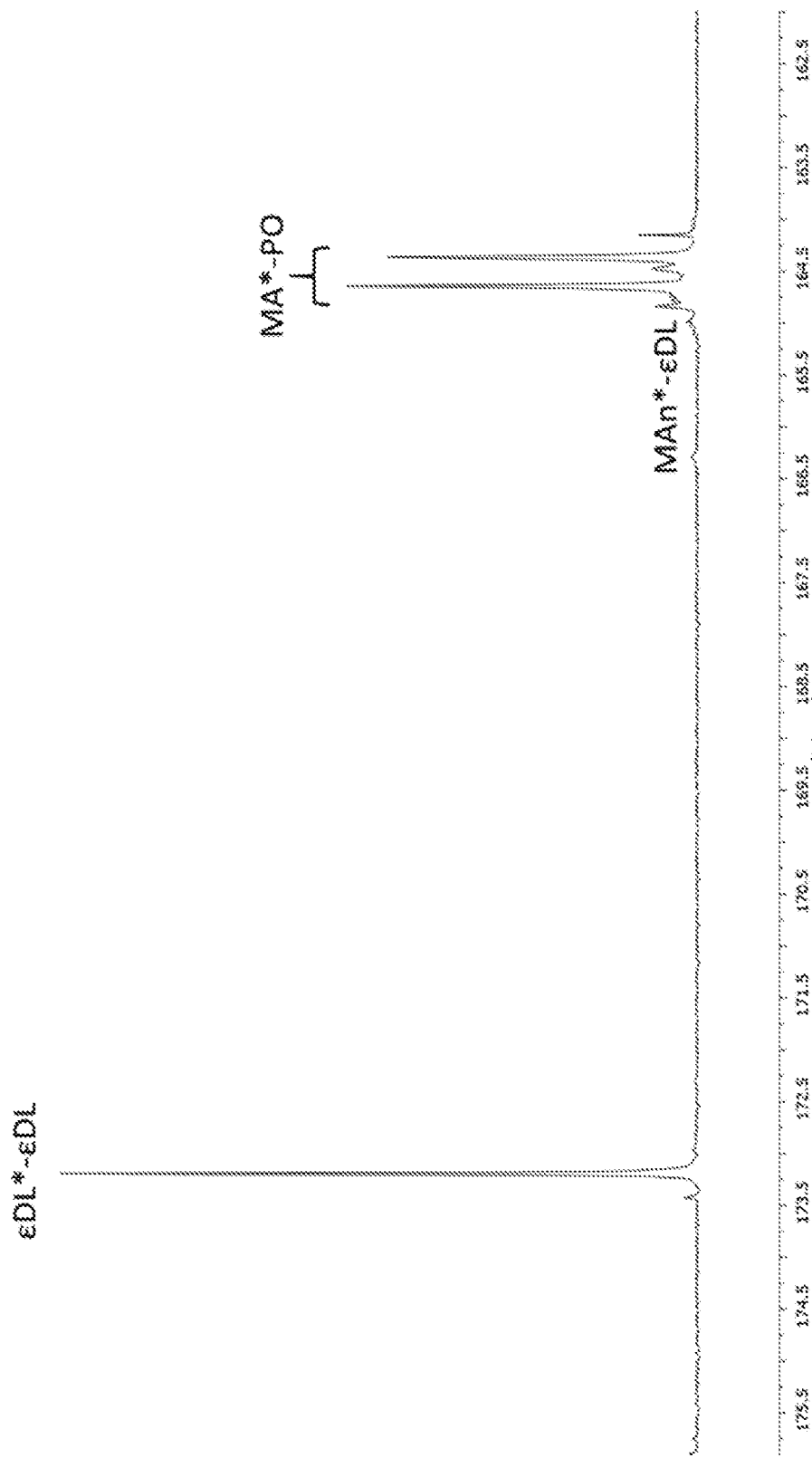
FIG. 30 is a $^{13}$C NMR spectra of the carbonyl diad region of poly(propylene maleate-b-ε-decalactone-b-propylene maleate) (125 MHz, CDCl$_3$, 303 K).
Figure 31:
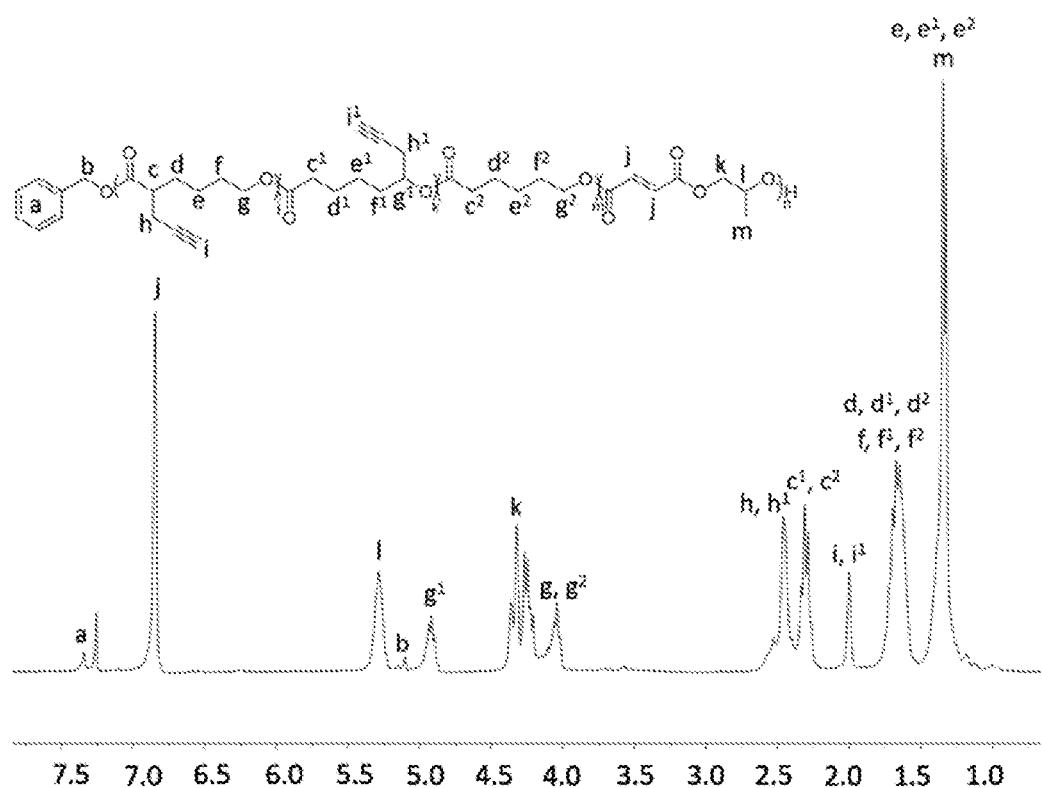
FIG. 31 is a ¹H NMR spectra of poly(α-propargyl-ε-caprolactone-b-O-propargyl-ε-nonalactone-b-ε-caprolactone-b-propylene fumarate) (300 MHz, CDCl₃, 303 K).
Figure 32:
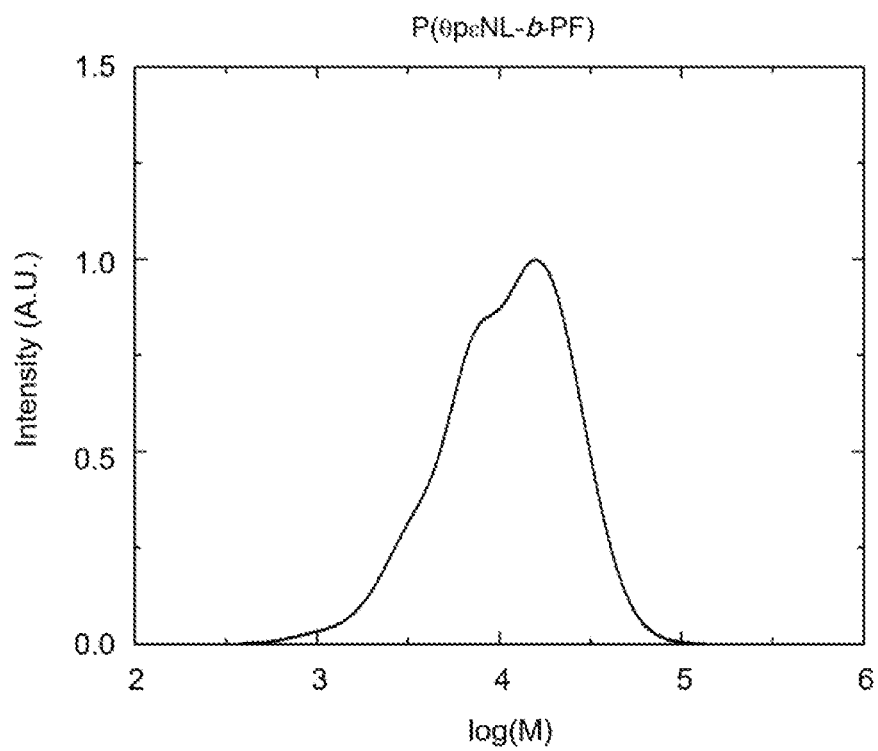
FIG. 32 is a SEC chromatogram for poly(α-propargyl-ε-caprolactone-b-O-propargyl-ε-nonalactone-b-ε-caprolactone-b-propylene fumarate). The molecular mass determined against poly(styrene) standards.

Since ROBOCOP using $Mg(BHT)_2(THF)_2$ allowed for the production of well-defined, diblock copolymers, the synthesis of an ABA type triblock copolymers was briefly investigated. The homopolymerization of εDL using $Mg(BHT)_2(THF)_2$ as a catalyst and 1,4-benzenedimethanol (BDM) as an initiator was conducted at a total monomer concentration of 2 M in toluene at 80° C. in a sealed, $N_2$ atmosphere. The homopolymerization was allowed to continue for 24 h before an equimolar quantity of MAn and PO in toluene was injected into the reaction. This monomer addition resulted in the growth of a triblock copolymer as a consequence of the bifunctionality of the sole initiating species. $^1H$ NMR spectroscopic analysis of the recovered material showed individual proton resonances corresponding to PDL (δ=4.86, 2.27, 0.88 ppm), PPM, (δ=6.27, 5.27, 4.26 ppm) and BDM (5.10 ppm). (See FIG. 29). Block sequencing was confirmed by analysis of the carbonyl diad resonance peaks from quantitative $^{13}C$ NMR spectroscopy. (See FIG. 30).

Lastly, the P(θpεNL-b-αpεCL-b-εCL-b-PM) polymer was made into a resin to introduce some of the potential applications of these polymers. (See FIGS. 13, 14, 25, 31 and 32). To make the resin, 11.3 kDA polymer was dissolved in an equal weight percent of diethyl fumarate with a previously reported mixture of photoinitiators and light scattering agents (4.1 wt. %). A stamp was printed using an EnvisionTEC Micro continuous digital light processing (cDLP) printer prior to attachment of Chromeo® 546-azide dye via copper-mediated azide-alkyne cycloaddition (CuAAC). It should be noted that cDLP printing of PPF with this resin composition has only been reported for $M_n$ less than 3.2 kDA. In order to attach the dye, the stamp was stamped into a solution containing the Chromeo® 546-azide dye, copper sulfate, and sodium ascorbate in an isopropyl alcohol and water mixture for 1 h. The film was washed three times with deionized water prior to imaging with a fluorescence microscope which confirmed the attachment of the Chromeo® 546-azide dye to the stamp.

The synthesis of chemically complex, sequence defined polyesters is necessary to diversify the properties needed for more demanding applications, but few available techniques offer this selectivity without reducing industrial viability. Thus, we introduce $Mg(BHT)_2(THF)_2$ as a cheap, catalyst for the ROBOCOP of a library of lactones with MAn and PO. To our knowledge, this is the first example of a "switch" system with a magnesium based catalyst. The ubiquity of the technique has been demonstrated through polymerization with various lactones of different size, substitution, and functionality. Though additional investigation is necessary to determine the tunability of these polymers, the ability to expand the polymerization to tri-block copolymers, print via stereolithographic methods and post-polymerization and post-print modify with functional groups demonstrates the utility of the materials in a wide variety of applications.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Abbreviations

ROP, ring-opening polymerization; ROCOP, ring-opening copolymerization; CHO, cyclohexene oxide; εCL, ε-caprolactone; βBL, β-butyrolactone; PCL, poly(ε-caprolactone); PLLA, poly(l-lactic acid); PPF, poly(propylene fumarate); ROBOCOP, ring-opening block-order copolymerization; $Mg(BHT)_2$ $(THF)_2$, 2,6-di-tert-butyl-4-methylphenoxide; MAn, maleic anhydride; PO, propylene oxide; BnOH, benzyl alcohol; DOSY, diffusion-order NMR spectroscopy; PPM, poly(propylene maleate); δVL, δ-valerolactone; γmεCL, γ-methyl-ε-caprolactone; εHL, ε-heptalactone; εDL, ε-decalactone; θpεNL, θ-propargyl-ε-nonalactone; αpεCL, α-propargyl-ε-caprolactone; εSεLs, ε-substituted ε-lactones; DSC, differential scanning calorimetry; BDM, 1,4-benzenedimethanol; CuAAC, copper-mediated azide-alkyne cycloaddition, cDLP, continuous digital light processing.

Materials

All reagents were purchased from Sigma-Aldrich, with the exception of 2,6-di-tert-4-methylphenol, which was purchased from Acros. $Mg(BHT)_2(THF)_2$ was synthesized according to a previously reported procedure. See, Calabrese, J.; Cushing, M. A.; Ittel, S. D.; Sterically hindered magnesium aryloxides. *Inorg. Chem.* 1988, 27, 867-870, the disclosure of which is incorporated herein by reference in its entirety. ε-heptalactone, γmεCL, and θ-propargyl-ε-nonalactone were synthesized using Baeyer-Villager oxidation reactions according to modified versions of previously reported procedures. See, van der Mee, L.; Helmich, F.; de Bruijn, R.; Vekemans, J. A. J. M., Palmans, A. R. A.; Meijer, E. W.; Investigation of Lipase-Catalyzed Ring-Opening Polymerizations of Lactones with Various Ring Sizes: Kinetic Evaluation. *Macromolecules* 2006, 39, 5021-5027; Jazkewitsch, O.; Mondrzyk, A.; Staffel, R.; Ritter, H.; Cyclodextrin-Modified Polyesters from Lactones and from Bacteria: An Approach to New Drug Carrier Systems. *Macromolecules* 2011, 44 (6), 1365-1371; and Wegener, M.; Huber, F.; Bolli, C.; Jenne, C.; Kirsch, S. F.; Silver-Free Activation of Ligated Gold(I) Chlorides: The Use of

[Me$_3$NB$_{12}$Cl$_{11}$]$^-$ as a Weakly Coordinating Anion in Homogeneous Gold Catalysis. *Chem. Eur. J.* 2015, 21, 1328-1336, the disclosure of which are incorporated by reference in their entirety. All solvents were purchased from Fisher and dried using an Innovative Technology Inc. Pure Solv MD-3 solvent purification system. Benzyl alcohol, propylene oxide, δ-valerolactone, ε-caprolactone, and ε-decalactone were dried over calcium hydride overnight prior to vacuum distillation. ω-pentadecalactone was dissolved in 75 wt. % toluene and dried over 3 Å molecular sieves. Maleic anhydride was sublimated and then dried in vacuo over P$_2$O$_5$ for 5 d. All other reagents were used as received.

Instrumental Methods

Proton ($^1$H) NMR spectra were recorded using a Varian Mercury 300 spectrometer. Carbon ($^{13}$C) NMR spectra were recorded using a Varian NMRS 500 spectrometer. All chemical shifts were recorded in parts per million (ppm) relative to the reference peak of chloroform solvent at δ=7.26 and 77.16 ppm for $^1$H and $^{13}$C NMR spectra, respectively. Molecular masses were determined through size exclusion chromatography (SEC) using a Tosoh EcoSEC HLC-8320GPC on TSKgel GMH$_{HR}$-M columns in series with refractive index (RI) detection. Molecular masses were calculated using a calibration curve determined from polystyrene standards with tetrahydrofuran (THF) as the eluent flowing at 1.0 mL min$^{-1}$ and a sample concentration of 10 mg mL$^{-1}$. DSC heating and cooling curves were obtained using a TA Instruments DSC 2910. Heating and cooling curves were run in triplicate in series under a nitrogen atmosphere at a heating rate of ±10° C. per min in a 40 µL aluminum crucible. The stamp was printed using an Envisiontec™ Micro Plus Advantage® continuous digital light processing (cDLP) printer.

Example 1

Synthesis of ε-heptalactone and
γ-methyl-ε-caprolactone

A single neck round bottom flask containing 250 mL methylene chloride was cooled in an ice bath prior to addition of 223 mmol of either 2-methylcyclohexanone or 4-methylcyclohexanone and 275 mmol of m-chloroperoxybenzoic acid. After refluxing for 3 days, the reaction mixture was cooled in an ice bath and filtered over Celite and washed with 10% Na$_2$S$_2$O$_3$ solution, saturated Na$_2$CO$_3$ solution, and brine. The organic layer was then dried with MgSO$_4$ and filtered prior to removal of solvent via rotary evaporation. Both products were dried over calcium hydride overnight and distilled under vacuum prior to use.

ε-heptalactone:

The presence of ε-heptalactone was confirmed by $^1$H NMR (300 MHz, 303 K, CDCl$_3$): δ=4.44 (m, CH$_2$(CH$_3$)O), 2.64 (m, C(=O)CH$_2$), 1.73 (m, CH$_2$CH(CH$_3$)), 1.42 (m, CH$_2$CH$_2$CH(CH$_3$)).

γ-Methyl-ε-Caprolactone:

The presence of γ-methyl-ε-caprolactone was confirmed by $^1$H NMR (300 MHz, 303 K, CDCl$_3$): δ=4.23 (m, CH$_2$O), 2.75 (m, C(=O)CH$_2$), 1.73 (m, CH$_2$CH(CH$_3$)), 1.40 (m, CH$_2$CH(CH$_3$)), 0.96 (m, CH$_2$CH(CH$_3$)).

Example 2

Figure 33:
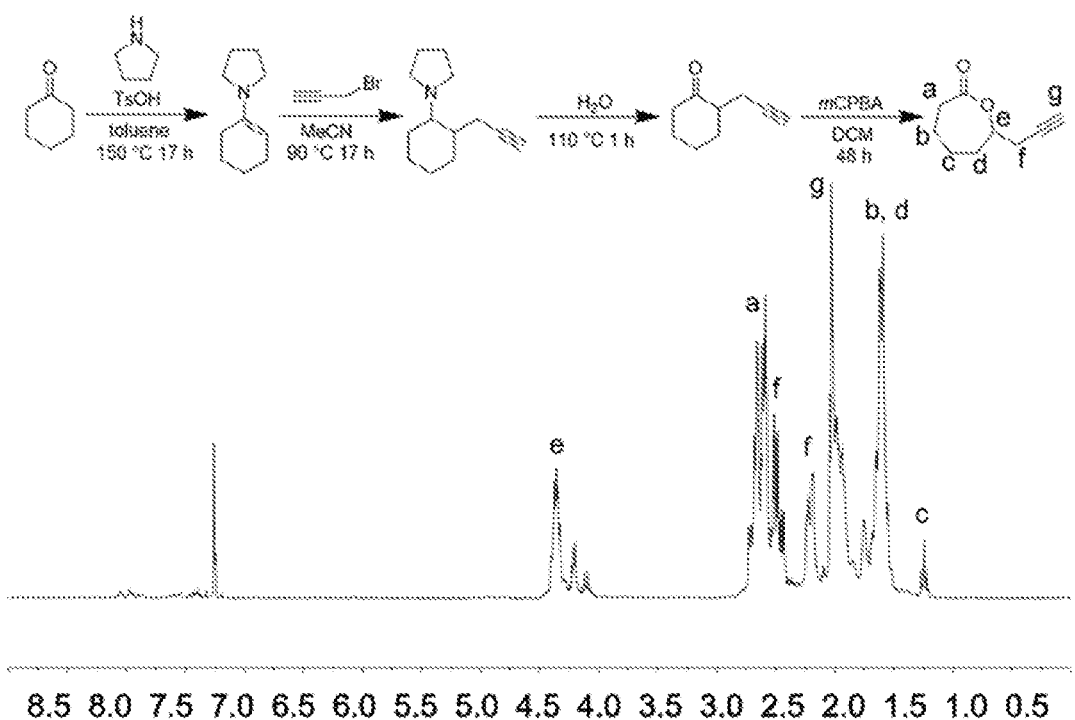
FIG. 33 is a ¹H NMR spectra of an isomeric mixture of α-propargyl-ε-caprolactone and θ-propargyl-ε-nonalactone (300 MHz, CDCl₃, 303 K).

Synthesis of θ-propargyl-ε-nonalactone 30.0 mL cyclohexanone (28.4 g, 289 mmol), 28.5 mL pyrrolidine (24.7 g, 347 mmol), and 55.0 mg p-toluenesulfonic acid monohydrate (0.289 mmol) were dissolved in 60 mL toluene in a round bottom flask equipped with a Dean-Stark apparatus and reflux condenser. The solution was stirred at 150° C. for 16 h. The resulting solution was washed cooled to room temperature and washed with water and brine prior to drying with MgSO$_4$ and solvent removal under reduced pressure. The product was purified by fractional distillation under vacuum (31.4 g, b.p. 107-114° C.) to give a pale yellow oil. This was dissolved in dry MeCN in a two neck round bottom flask then equipped with a reflux condenser prior to drop wide addition of 26.8 mL propargyl bromide (80% in toluene, 37.0 g, 249 mmol) was then added drop-wise to the solution. The reaction was stirred under reflux over night then cooled to room temperature prior to removal of solvent under reduced pressure. 220 mL deionized water was added to the residue and the solution stirred under reflux for 1 h. The product was extracted with Et$_2$O then washed with brine and dried over MgSO$_4$. Fractional distillation under vacuum yielded an isomeric mixture of θ-propargyl-ε-nonalactone and α-propargyl-ε-caprolactone as a colorless oil (12.9 g, 94.7 mmol, b.p. 93-95° C./16 mbar). 160 mL of methylene chloride was cooled in an ice bath prior to addition of the θ-propargyl-ε-nonalactone and α-propargyl-ε-caprolactone mixture (12.9 g, 94.7 mmol) and m-chloroperoxybenzoic acid (24.5 g, 142.1 mmol). The reaction mixture was refluxed for 48 h and filtered after cooling to room temperature. The product was washed with a concentrated aqueous sodium sulfite solution and dried over MgSO$_4$ prior to removal of solvent using rotary evaporation. The final product was dried over calcium hydride overnight and distilled under vacuum before use. (See FIG. 33).

Example 3

Synthesis of magnesium
2,6-di-tert-butyl-4-methylphenoxide
(Mg(BHT)$_2$(THF)$_2$ Using standard Schlenk line techniques, a schlenk was filled with 2,6-di-tert-butyl-4-methylphenol (BHT) (6.66 g, 30 mmol) and dissolved into dry toluene (30 ml) added by cannula transfer. Di-n-butylmagnesium (1 M in hexane, 15 ml, 15 mmol) was added dropwise to the reaction with stirring. The reaction was stirred for a further 2 hours followed by removing solvent. Hexanes (12.5 ml) were added to the reaction vessel followed by addition of tetrahydrofuran (THF) (2.5 ml). After stirring for 2 hours under N$_2$, solvent can be removed, and final product was obtained as a solid (See, Scheme 11).

Scheme 11 Synthesis of magnesium 2,6-di-tert-butyl-4-methylphenoxide (Mg(BHT)₂(THF)₂)

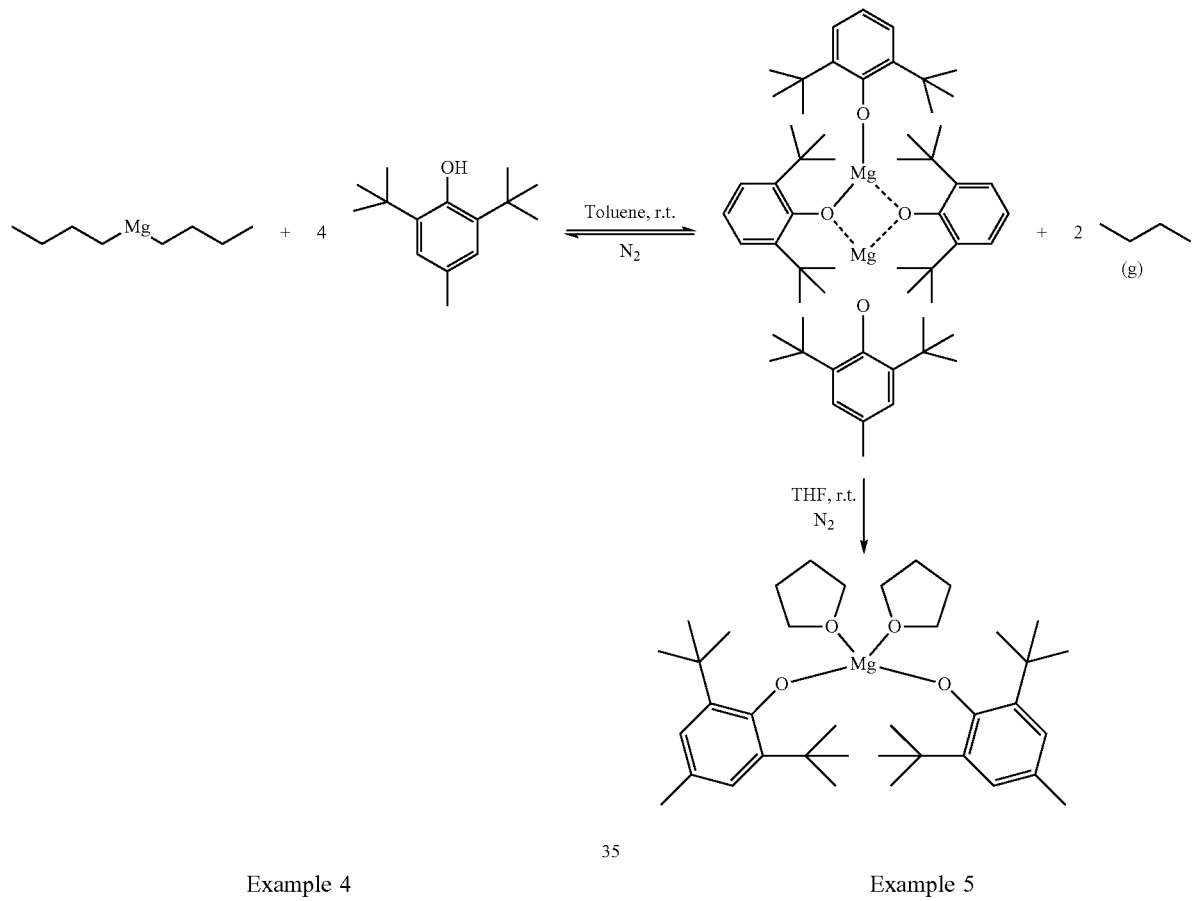

Example 4

General Procedure for Sequential Polymerization

Using standard Schlenk line techniques, an ampoule is filled with a magnesium catalyst, such as Mg(BHT)$_2$(THF)$_2$, an initiating alcohol such as benzyl alcohol and a lactone, such as ε-caprolactone. The reagents were dissolved into toluene to a total monomer concentration of 2 M. The ampoule was sealed and heated at about 80° C. for about 24 h or until all of the lactone has reacted. A 2 M solution of propylene oxide and maleic anhydride dissolved in toluene is then added to the polymerization via cannula and heating is continued at about 80° C. for a further 120 h. The resultant poly(lactone-b-propylene maleate)polymer is then recovered by precipitation in excess diethyl ether.

Example 5

General Synthesis of Poly(Lactone-b-Propylene Maleate) Copolymers

Using standard glovebox techniques, an ampoule was filled with a 2 M solution of Mg(BHT)$_2$(THF)$_2$, benzyl alcohol, and a lactone monomer in toluene. The sealed ampoule was heated at 80° C. After a defined period of time a 2 M solution of propylene oxide and maleic anhydride in toluene was added to the reaction ampoule in a N$_2$ environment. The resealed ampoule was heated back to 80° C. for 5 days. The resultant polymer was recovered by precipitation in hexanes. The specific reactions conditions for the various poly(lactone-b-propylene maleate) copolymers synthesized are set forth in Table 2, below.

TABLE 2

| Lactone monomer (L) | Time (h) | Moles of initator | Vol. of initiator (mL) | Moles of catalyst | Mass of catalyst (g) | Moles of lactone | Vol. of lactone (mL) | Moles of MAn | Mass of MAn (g) | Moles of PO | Vol. of PO (mL) | Molar concentration |
|---|---|---|---|---|---|---|---|---|---|---|---|---|
| δVL | 1 | 0.97 | 0.1 | 0.97 | 0.59 | 0.48 | 4.496 | 0.048 | 4.74 | 0.048 | 3.394 | 2 |
| εCL | 1 | | | | | | 5.375 | | | | | |
| εHL | 24 | | | | | | 6.216 | | | | | |
| γmεCL | 1 | | | | | | 6.216 | | | | | |
| ΘpεNL | 24 | | | | | | 6.765 | | | | | |
| εDL | 8 | | | | | | 8.460 | | | | | |
| ωPDL | 24 | | | | | | 24.25* | | | | | |

TABLE 2-continued

| Lactone monomer (L) | Time (h) | Moles of initator | Vol. of initiator (mL) | Moles of catalyst | Mass of catalyst (g) | Moles of lactone | Vol. of lactone (mL) | Moles of MAn | Mass of MAn (g) | Moles of PO | Vol. of PO (mL) | Molar concentration |
|---|---|---|---|---|---|---|---|---|---|---|---|---|
| δVL/εCL | 24 | | | | | | 2.248/ 2.768 | | | | | |

*ωPDL was made into a 2M solution in toluene prior to use. The volume shown is the volume of this solution used in the polymerization.

Figure 34:
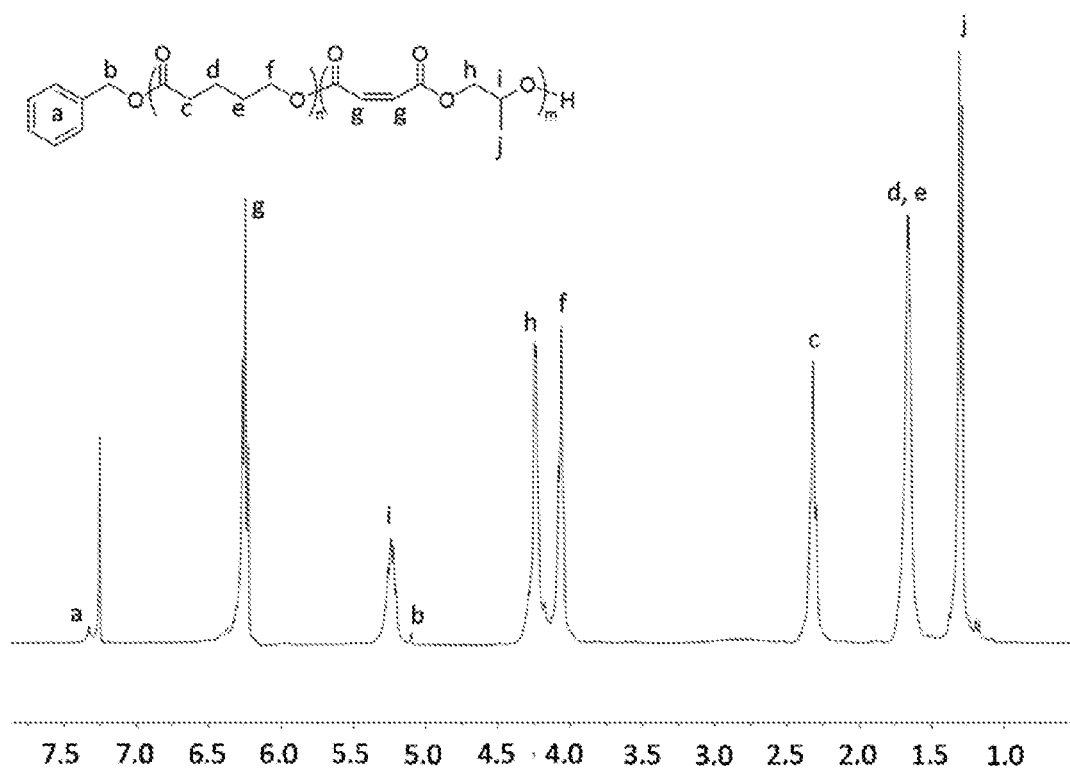
FIG. 34 is a ¹H NMR spectra of poly(δ-valerolactone-b-propylene maleate) (300 MHz, CDCl₃, 303 K).
Figure 35:
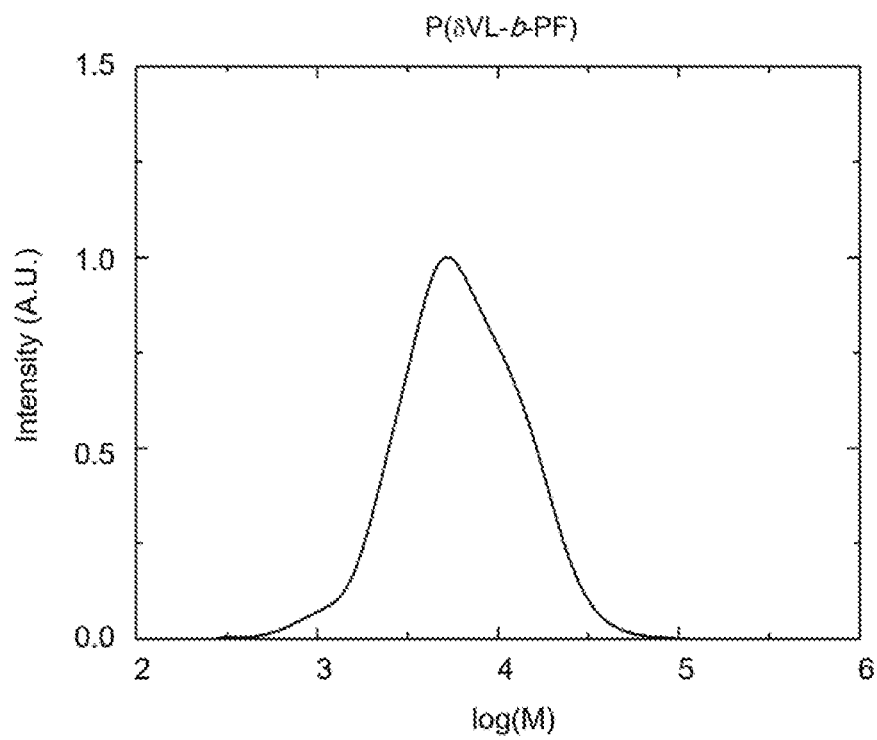
FIG. 35 is a SEC chromatogram for poly(δ-valerolactone-b-propylene maleate). The molecular mass determined against poly(styrene) standards.

P(δVL-b-PM):

The P(δVL-b-PM) polymer was produced as set forth above and characterized by: $^1$H NMR (300 MHz, 303 K, CDCl$_3$): δ=7.33 (m, Ar), 6.24 (m, OC(=O)H=CH(=O)O), 5.24 (m, CH$_2$CH(CH$_3$)O), 5.10 (s, C=OOCH$_2$Ar), 4.23 (m, PO CH$_2$OC=O), 4.06 (m, δVL CH$_2$OC=O), 2.31 (s, δVL CH$_2$C=OO), 1.30 (m, PO CH$_2$CH(CH$_3$)O), 1.66 (all remaining hydrogens) ppm (See FIG. 34); $^{13}$C NMR (125 MHz, 303K, CDCl$_3$): δ=173.32 (δVL*-δVL, OCOCH$_2$), 173.12 (δVL-PO, OCOCH$_2$), 165.15 (MAn*-δVL, OCOCH$_2$), 164.77 and 164.49 (MAn*-PO, OCOCH$_2$), 130.54 and 130.00 (MAn*-PO, O(O)C*CH=CH), 129.40 and 129.13 (MAn*-PO, O(O)C*CH=CH), 128.33 and 128.31 (εCL-MAn*, O(O)CCH=CH), 69.26 (MAn*-PO, OCH(CH$_3$)CH$_2$), 66.56 (MAn*-PO, OCH(CH$_3$)CH$_2$), 64.01 (δVL*-δVL, OCH$_2$), 33.81 (δVL*-δVL, OCOCH$_2$), 28.22 (δVL, OCH$_2$CH$_2$), 21.55 (δVL, OCOCH$_2$CH$_2$) and 16.34 (PO, CH$_2$CH(CH$_3$)O) ppm (See FIG. 7); and SEC (THF): M$_n$=6.5 kDa, M$_w$=8.3 kDa, Đ$_M$=1.85. Yield: 89% (See FIG. 35).

P(εHL-b-PM):

The P(εHL-b-PM) polymer was produced as set forth above and characterized by: $^1$H NMR (300 MHz, 303 K, CDCl$_3$): δ=7.32 (m, Ar), 6.23 (m, OC(=O)H=CH(=O)O), 5.22 (m, CH$_2$CH(CH$_3$)O), 5.07 (s, C=OOCH$_2$Ar), 4.85 (m, εHL CH$_2$OC=O), 4.23 (m, PO CH$_2$OC=O), 2.23 (s, CH$_2$C=OO), 1.16 (m, εHL CH$_3$), 1.63-1.22 (all remaining hydrogens) ppm (See FIG. 36); $^{13}$C NMR (125 MHz, 303K, CDCl$_3$): δ=173.10 (εHL*-εHL, OCOCH$_2$), 165.02 (MAn*-εHL, OCOCH$_2$), 164.63 and 164.39 (MAn*-PO, OCOCH$_2$), 130.40 and 129.91 (MAn*-PO, O(O)C*CH=CH), 129.77 and 129.24 (MAn*-PO, O(O)C*CH=CH), 125.43 (εHL-MAn*, O( )CCH=CH), 77.53, 70.37 (εHL*-εHL, OCH$_2$), 69.12 (MAn*-PO, OCH(CH$_3$)CH$_2$), 66.33 (MAn*-PO, OCH(CH$_3$)CH$_2$), 35.51 (εHL*-εHL, CH$_2$CH$_2$COO), 34.44 (εHL, CH$_2$CH$_2$CH(CH$_3$)), 16.17 (PO, CH$_2$CH(CH$_3$)O), 19.89 (εHL, CH$_3$CH(CH$_2$)$_2$), 30.29 and 24.89 (all remaining carbons) ppm (See FIG. 9); and SEC (THF): M$_n$=4.5 kDa, M$_n$=9.8 kDa, Đ$_M$=1.80. Yield: 92% (See FIG. 37).

Figure 38:
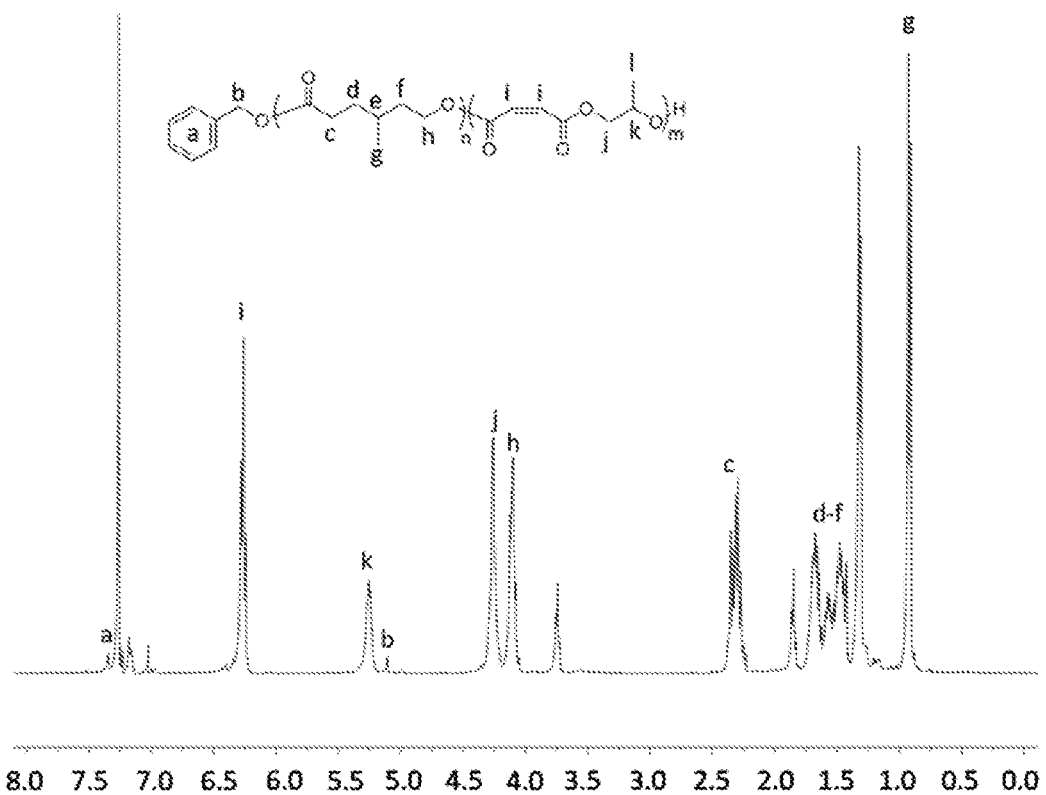
FIG. 38 is a ¹H NMR spectra of poly(γ-methyl-ε-caprolactone-b-propylene maleate) (300 MHz, CDCl₃, 303 K).
Figure 39:
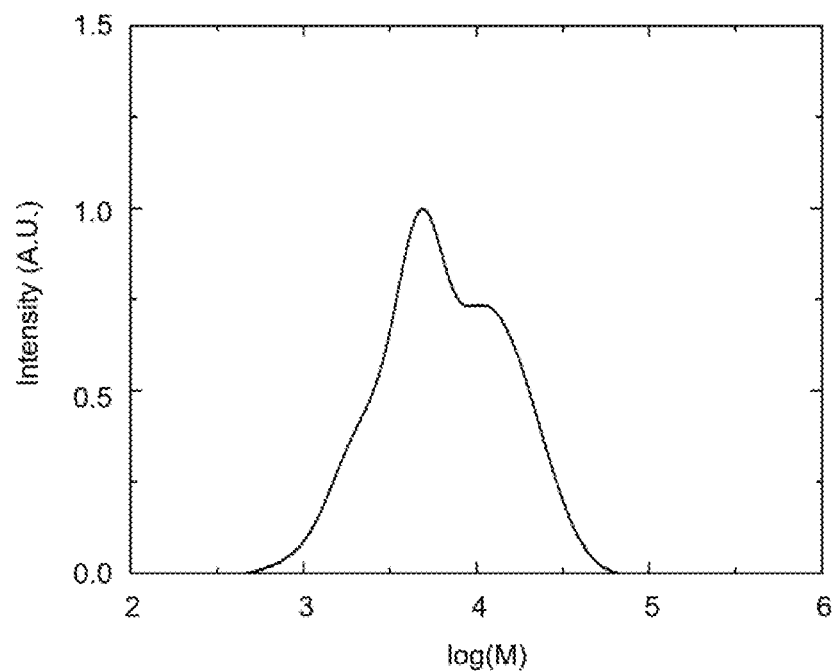
FIG. 39 is a SEC chromatogram for poly(γ-methyl-ε-caprolactone-b-propylene maleate). The molecular mass determined against poly(styrene) standards.

P(γmεCL-b-PM):

The P(γmεCL-b-PM) polymer was produced as set forth above and characterized by: $^1$H NMR (300 MHz, 303 K, CDCl$_3$): δ=7.32 (m, Ar), 6.26 (m, OC(=O)H=CH(=O)O), 5.26 (m, CH$_2$CH(CH$_3$)O), 5.11 (s, C=OOCH$_2$Ar), 4.26 (m, PO CH$_2$OC=O), 4.10 (m, γmεCL CH$_2$OC(=O)), 2.29 (s, CH$_2$C=OO), 1.16 (m, γmεCL CH(CH$_3$)), 1.63-1.22 (all remaining hydrogens) ppm (See FIG. 38); $^{13}$C NMR (125 MHz, 303K, CDCl$_3$): δ=173.53 (γmεCHL*-γmεCHL, OCOCH$_2$), 164.44 (MAn*-γmεCHL, OCOCH$_2$), 164.19 and 163.82 (MAn*-PO, OCOCH$_2$), 130.29 and 129.94 (MAn*-PO, O(O)C*CH=CH), 129.04 and 128.77 (MAn*-PO, O(O)C*CH=CH), 125.24 (γmεCHL-MAn*, O( )CCH=CH), 77.34, 69.12 (γmεCHL*-γmεCHL, OCH$_2$), 68.10 (MAn*-PO, OCH(CH$_3$)CH$_2$), 66.36 (MAn*-PO, OCH(CH$_3$)CH$_2$), 35.02 (γmεCHL*-γmεCHL, CH$_2$CH$_2$COO), 34.56 (γmεCHL, CH$_2$CH$_2$CH(CH$_3$)), 16.13 (PO, CH$_2$CH(CH$_3$)O), 18.87 (γmεCHL, CH$_3$CH), 31.66 and 29.36 (all remaining carbons) ppm (See FIG. 11); and SEC (THF): M$_n$=7.4 kDa, M$_w$=9.2 kDa, Đ$_M$=2.02. Yield: 87% (See FIG. 39).

P(θpεNL-b-PM):

The P(θpεNL-b-PM) polymer was produced as set forth above and characterized by: $^1$H NMR (300 MHz, 303 K, CDCl$_3$): δ=7.34 (m, Ar), 6.85 (m, OC(=O)H=CH(=O)O), 5.29 (m, CH$_2$CH(CH$_3$)O), 5.10 (s, C=OOCH$_2$Ar), 4.92 (m, CH(CH$_2$CCH)) 4.34 (m, PO CH$_2$OC=O), 4.05 (m, αpεCL, CH$_2$OC(=O)), 2.45 (m, CH$_2$CCH), 2.34 (s, CH$_2$C=OO), 2.01 (s, CCH), 1.65-1.39 (all remaining hydrogens) ppm; $^{13}$C NMR (125 MHz, 303K, CDCl$_3$): δ=174.12 (αpεCL*-αpεCL, OCOCH$_2$), 173.42 (εCL*-εCL, OCOCH2), 172.87 (θpεNL*-θpεNL), 164.36 and 163.98 (MAn*-PO, OCOCH$_2$), 133.99 and 133.75 (MAn*-PO, O(O)C*CH=CH), 133.50 and 133.26 (MAn*-PO, O(O)C*CH=CH), 81.21 (αpεCL and θpεNL, CH(CH$_2$CCH)), 78.57 (θpεNL, CH(CH$_2$CCH)), 71.25 (αpεCL, OC(=O)C), 70.53 (εCL, OC(=O)C), 70.07 (αpεCL and εCL, COC(=O)), 69.22 (MAn*-PO, OCH(CH$_3$)CH$_2$), 67.89 (αpεCL and θpεNL, CH(CH$_2$CCH)), 66.57 (MAn*-PO, OCH(CH$_3$)CH$_2$), 16.33 (PO, CH$_2$CH(CH$_3$)O), 36.42-21.08 (all remaining carbons) ppm; and SEC (THF): M$_n$=7.4 kDa, M$_w$=14.6 kDa, Đ$_M$=1.97. Yield: 86%.

P(εDL-b-PM):

The P(εDL-b-PM) polymer was produced as set forth above and characterized by: $^1$H NMR (300 MHz, 303 K, CDCl$_3$): δ=7.33 (m, Ar), 6.25 (m, OC(=O)H=CH(=O)O), 5.25 (m, CH$_2$CH(CH$_3$)O), 5.09 (s, C=OOCH$_2$Ar), 4.84 (m, εDL CH$_2$OC=O), 4.24 (m, PO CH$_2$OC=O), 2.26 (s, CH$_2$C=OO), 0.87 (m, εDL CH$_3$(CH$_2$)$_3$), 1.65-1.20 (all remaining hydrogens) ppm (See FIG. 40); $^{13}$C NMR (125 MHz, 303K, CDCl$_3$): δ=173.41 (εDL*-εDL, OCOCH$_2$), 164.81 and 164.53 (MAn*-PO, OCOCH$_2$), 130.59 and 130.11 (MAn*-PO, O(O)C*CH=CH), 129.96 and 129.47 (MAn*-PO, O(O)C*CH=CH), 125.65 (εDL-MAn*, O( )CCH=CH), 74.04 (εDL*-εDL, OCH$_2$), 69.30 (MAn*-PO, OCH(CH$_3$)CH$_2$), 66.58 (MAn*-PO, OCH(CH$_3$)CH$_2$), 34.64 (εDL*-εDL, OCOCH$_2$), 33.93 (εDL, CH$_2$CH$_2$CH(Bu)), 16.37 (PO, CH$_2$CH(CH$_3$)O), 14.12 (εDL, CH$_3$(CH$_2$)$_3$), 30.48, 27.60, 25.13 and 22.71 (all remaining carbons) ppm (See FIG. 15); and SEC (THF): M$_n$=2.6 kDa, M$_w$=4.0 kDa, Đ$_M$=1.56. Yield: 85% (See FIG. 41).

Figure 42:
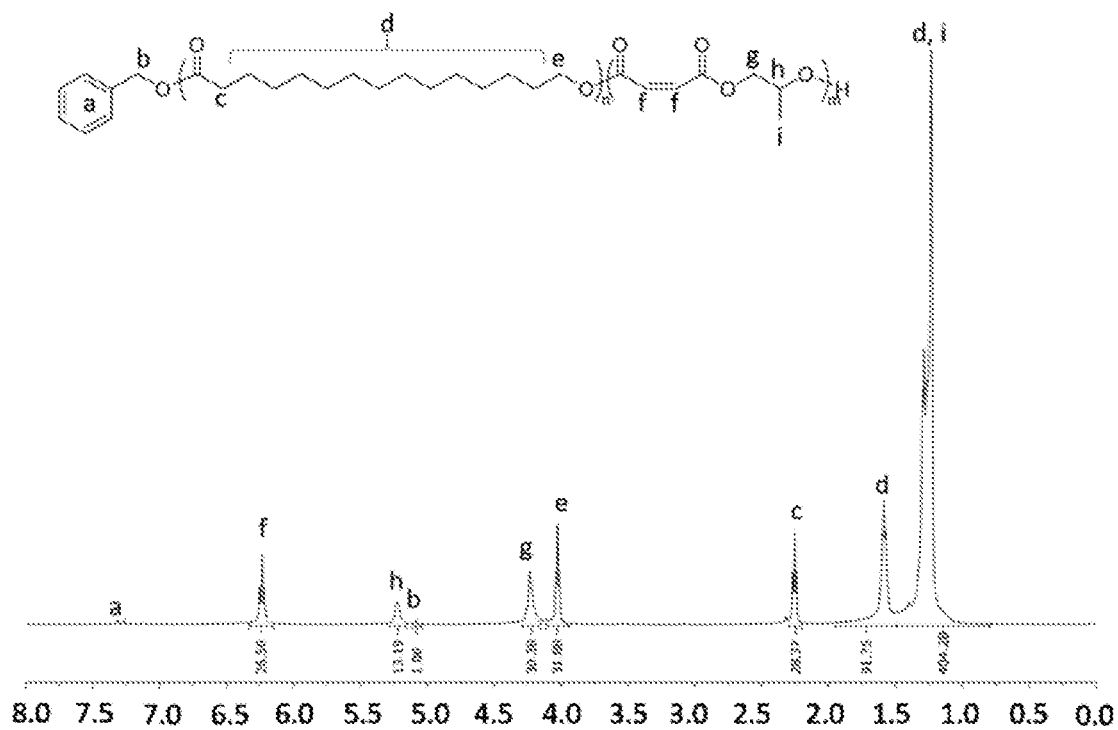
FIG. 42 is a ¹H NMR spectra of poly(ω-pentadecalactone-b-propylene maleate) (300 MHz, CDCl₃, 303 K).

P(PDL-b-PM):

The P(PDL-b-PM) polymer was produced as set forth above and characterized by: $^1$H NMR (300 MHz, 303 K, CDCl$_3$): δ=7.32 (m, Ar), 6.24 (m, OC(=O)H=CH(=O)O), 5.23 (m, CH$_2$CH(CH$_3$)O), 5.08 (s, C=OOCH$_2$Ar), 4.23 (m, PO CH$_2$OC=O), 4.02 (m, PDL CH$_2$OC=O), 2.25 (s, PDL CH$_2$C=OO), 1.60-1.23 (all remaining hydrogens) ppm (See FIG. 42); $^{13}$C NMR (125 MHz, 303K, CDCl$_3$): δ=173.93 (PDL*-PDL, OCOCH$_2$), 173.63 (PDL-PO, OCOCH$_2$), 165.12 (MAn*-PDL, OCOCH$_2$), 164.69 and 164.41 (MAn*-PO, OCOCH$_2$), 129.97 and 129.82 (MAn*-PO, O(O)C*CH=CH), 129.35 and 129.27 (MAn*-PO, O(O)C*CH=CH), 128.55 and 128.18 (PDL-MAn*, O(O)CCH=CH), 69.18 (MAn*-PO, OCH(CH$_3$)CH$_2$), 66.45

Figure 43:
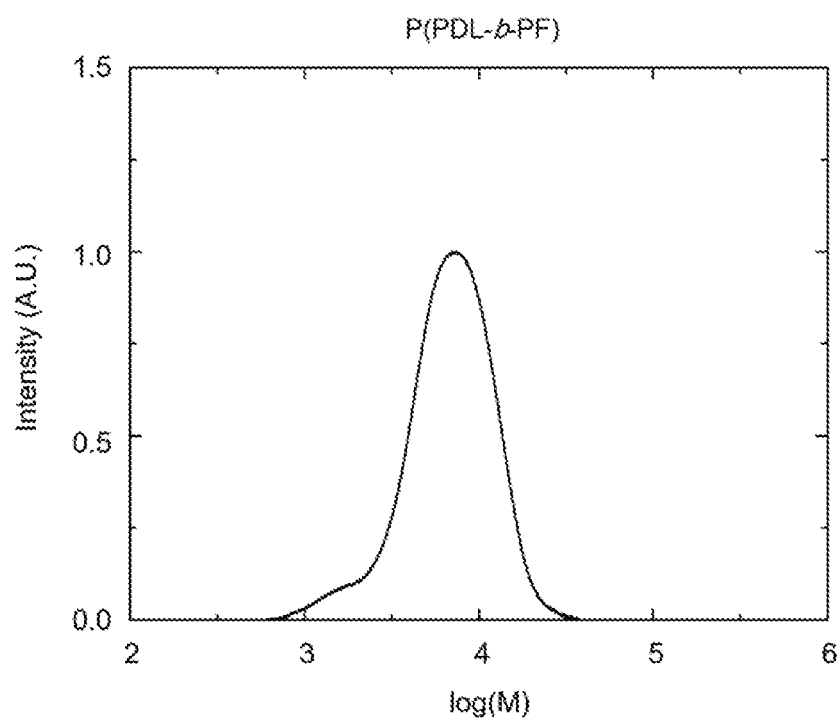
FIG. 43 is a SEC chromatogram for poly(ω-pentadecalactone-b-propylene maleate). The molecular mass determined against poly(styrene) standards.

(MAn*-PO, OCH(CH$_3$)CH$_2$), 64.13 (PDL*-PDL, OCH$_2$), 34.12 (PDL*-PDL, OCOCH$_2$), 30.34 (PDL, OCH$_2$CH$_2$), and 16.22 (PO, CH$_2$CH(CH$_3$)O) ppm (See FIG. 17); and SEC (THF): M$_n$=5.5 kDa, M$_w$=7.8 kDa, Đ$_M$=1.41. Yield: 84% (See FIG. 43).

Figure 44:
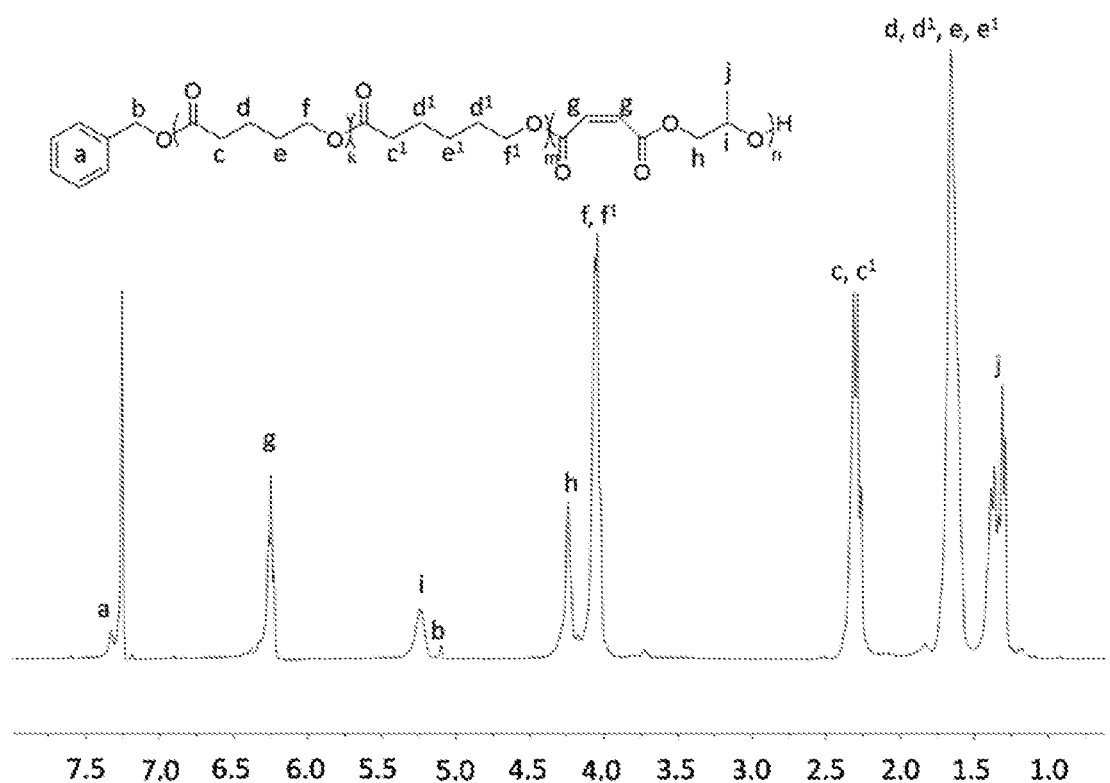
FIG. 44 is a ¹H NMR spectra of poly(δ-valerolactone-co-ε-caprolactone-b-propylene maleate) (300 MHz, CDCl₃, 303 K).
Figure 45:
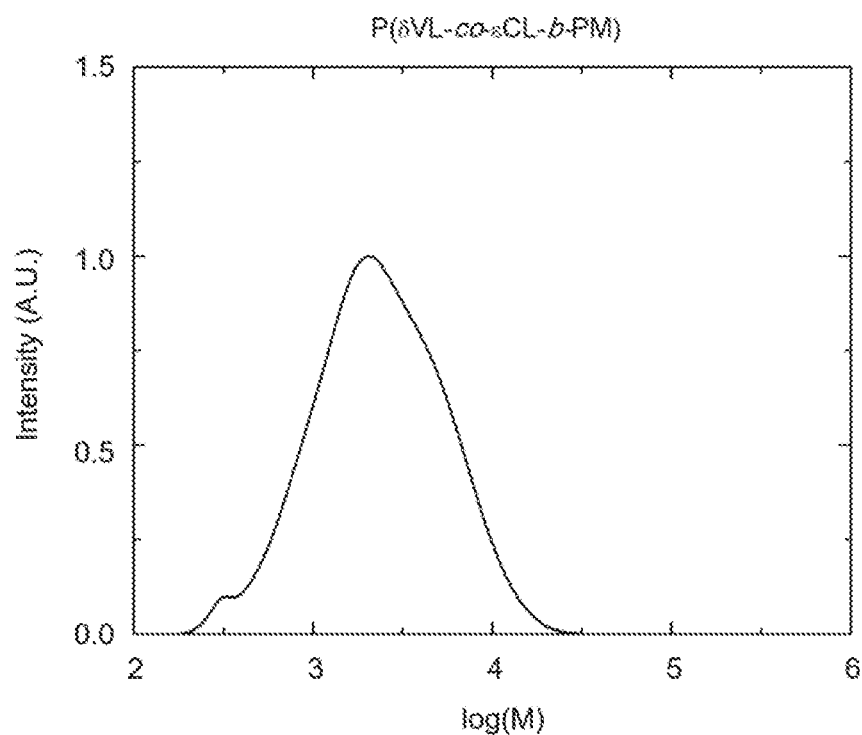
FIG. 45 is a SEC chromatogram for poly(δ-valerolactone-co-ε-caprolactone-b-propylene maleate). The molecular mass determined against poly(styrene) standards.

P(δVL-co-εCL-b-PM):

The P(δL-co-εCL-b-PM) polymer was produced as set forth above and characterized by: $^1$H NMR (300 MHz, 303 K, CDCl$_3$): δ=7.32 (m, Ar), 6.24 (m, OC(=O)H=CH(=O)O), 5.21 (m, CH$_2$CH(CH$_3$)O), 5.08 (s, C=OOCH$_2$Ar), 4.26 (m, PO CH$_2$OC=O), 4.03 (m, CH$_2$OC=O), 2.28 (s, CH$_2$C=OO), 1.65-1.28 (all remaining hydrogens) ppm (See FIG. 44); $^{13}$C NMR (125 MHz, 303K, CDCl$_3$): δ=173.49 (εCL*-εCL, OCOCH$_2$), 173.46 (εCL*-δVL, OCOCH$_2$), 173.25 (δVL*-εCL, OCOCH$_2$), 173.23 (δVL*-δVL, OCOCH$_2$), 173.01 (δVL*-PO or εCL*-PO, OCOCH$_2$), 165.06 (MAn*-δVL or MAn*-εCL, OCOCH$_2$), 164.68 and 164.40 (MAn*-PO, OCOCH$_2$), 130.54 and 130.00 (MAn*-PO, O(O)C*CH=CH), 129.40 and 129.13 (MAn*-PO, O(O)C*CH=CH), 128.33 and 128.31 (εCL-MAn* or δVL-MAn*, O(O)CCH=CH), 69.26 (MAn*-PO, OCH(CH$_3$)CH$_2$), 66.56 (MAn*-PO, OCH(CH$_3$)CH$_2$), 64.01 (δVL or εCL, OCH$_2$), 33.81 (δVL or εCL, OCOCH$_2$), 28.22 (δVL or εCL, OCH$_2$CH$_2$), 21.55 (δVL or εCL, OCOCH$_2$CH$_2$) and 16.34 (PO, CH$_2$CH(CH$_3$)O) ppm (See FIG. 19); and SEC (DMF): M$_n$=1.6 kDa, M$_w$=3.2 kDa, Đ$_M$=1.97. Yield: 82% (See FIG. 45).

Example 6

Synthesis of Poly(δ-Valerolactone-b-Propylene Maleate)

Poly(δ-valerolactone-b-propylene maleate) was synthesized using the general method set forth in Example 4 using δ-valerolactone as shown in Scheme 12, below and the using reaction parameters shown in Table 3, below.

Scheme 12
Sequential polymerization of δ-valerolactone followed by
the copolymerization of maleic anhydride and propylene oxide.

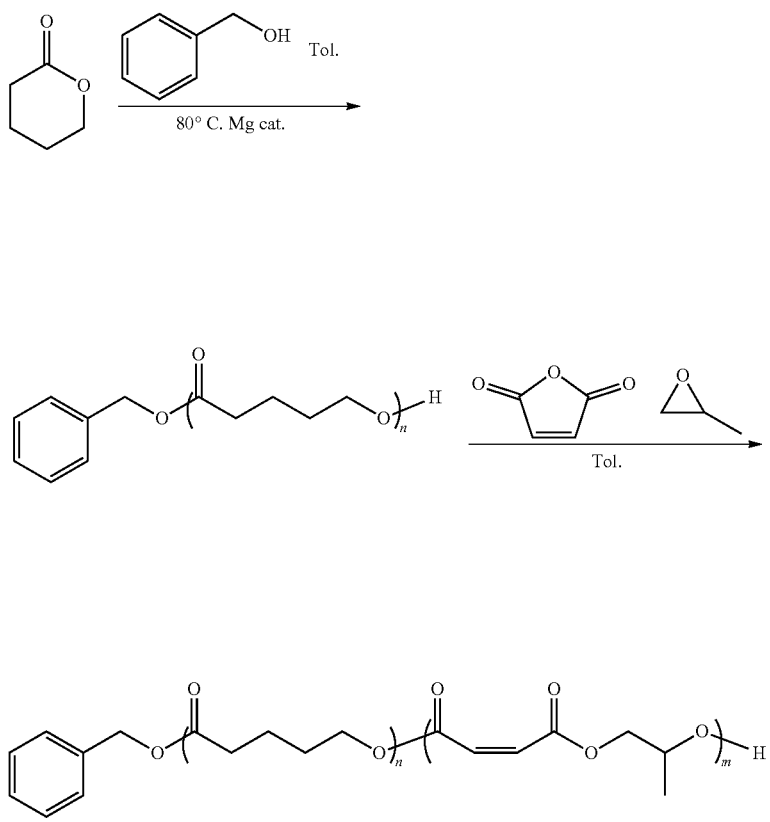

TABLE 3

| Initiator | mol. eq. δVL | mol. eq. PO | mol. eq. MA | T (° C.) | Time 1 (h) | Time 2 (h) | M$_{n, NMR}$ (kDa) | M$_{n, GPC}$ (kDa) | Đ$_M$ |
|---|---|---|---|---|---|---|---|---|---|
| BnOH | 50 | 50 | 50 | 80 | 24 | 120 | 8.5 | 6.5 | 1.90 |

The presence of a Poly(δ-valerolactone-b-propylene maleate) product was confirmed by ¹H NMR (300 MHz, 303 K, CDCl₃): δ=7.33 (m, Ar), 6.24 (m, OC(=O)H=CH(=O)O), 5.24 (m, CH₂CH(CH₃)O), 5.10 (s, C=OOCH₂Ar), 4.23 (m, PO CH₂OC=O), 4.06 (m, δVL CH₂OC=O), 2.31 (s, δVL CH₂C=OO), 1.30 (m, PO CH₂CH(CH₃)O), 1.66 (all remaining hydrogens) ppm (see, FIG. 34); ¹³C NMR (125 MHz, 303K, CDCl₃): δ=173.32 (δVL*-δVL, OCOCH₂), 173.12 (δVL*-PO, OCOCH₂), 165.15 (MAn*-δVL, OCOCH₂), 164.77 (MAn*-PO, OCOCH₂), 164.49 (MAn*-εCL, OCOCH₂), 130.54 and 130.00 (MAn*-PO, O(O)C*CH=CH), 129.40 and 129.13 (MAn*-PO, O(O)C*CH=CH), 128.33 and 128.31 (εCL-MAn*, O(O)CCH=CH), 69.26 (MAn*-PO, OCH(CH₃)CH₂), 66.56 (MAn*-PO, OCH(CH₃)CH₂), 64.01 (δVL*-δVL, OCH₂), 33.81 (δVL*-δVL, OCOCH₂), 28.22 (δVL, OCH₂CH₂), 21.55 (δVL, OCOCH₂CH₂) and 16.34 (PO, CH₂CH(CH₃)O) ppm (see, FIG. 7); and SEC (DMF): $M_n$=6.5 kDa, $M_w$=12.5 kDa, $Đ_M$=1.90. A DOSY NMR spectrum of poly (δ-valerolactone-b-propylene maleate) (500 MHz, 303 K, CDCl₃) is attached as FIG. 8.

Example 7

Synthesis of Poly(ε-Caprolactone-b-Propylene Maleate)

Poly(ε-caprolactone-b-propylene maleate) was synthesized using the general method set forth in Example 4 using ε-caprolactone as shown in Scheme 13, below and the using reaction parameters shown in Table 4, below.

Scheme 13
Sequential polymerization of ε-caprolactone followed by the copolymerization of maleic anhydride and propylene oxide.

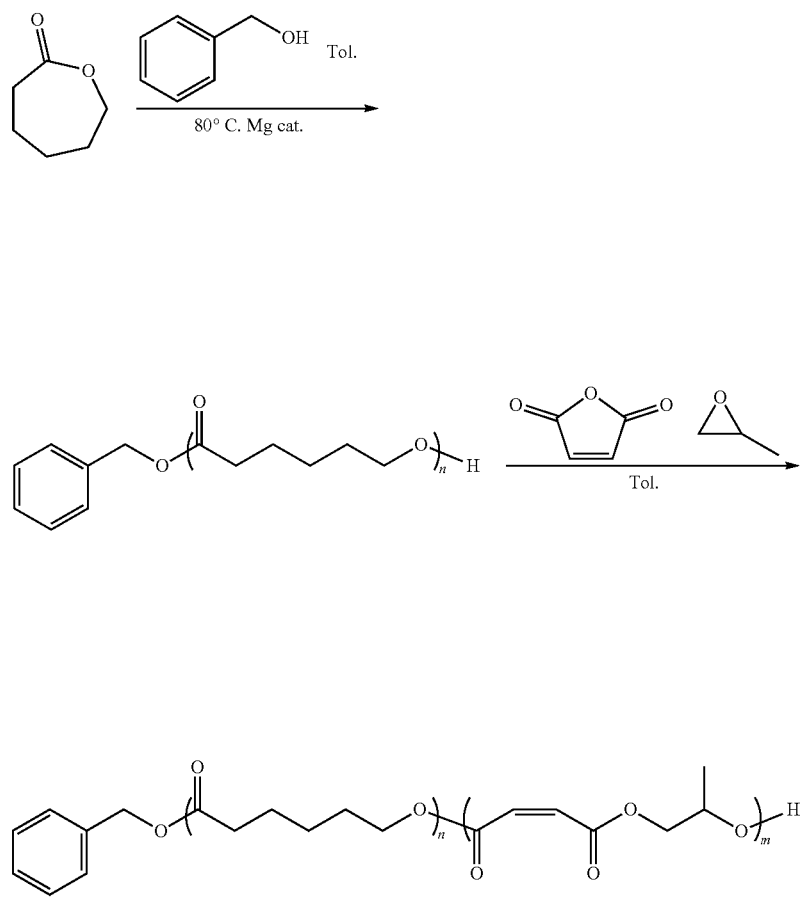

TABLE 4

| Initiator | mol. eq. εCL | mol. eq. PO | mol. eq. MA | T (° C.) | Time 1 (h) | Time 2 (h) | $M_{n, NMR}$ (kDa) | $M_{n, GPC}$ (kDa) | $Đ_M$ |
|---|---|---|---|---|---|---|---|---|---|
| BnOH | 25 | 25 | 25 | 80 | 24 | 120 | 8.8 | 12.5 | 1.24 |

Figure 2:
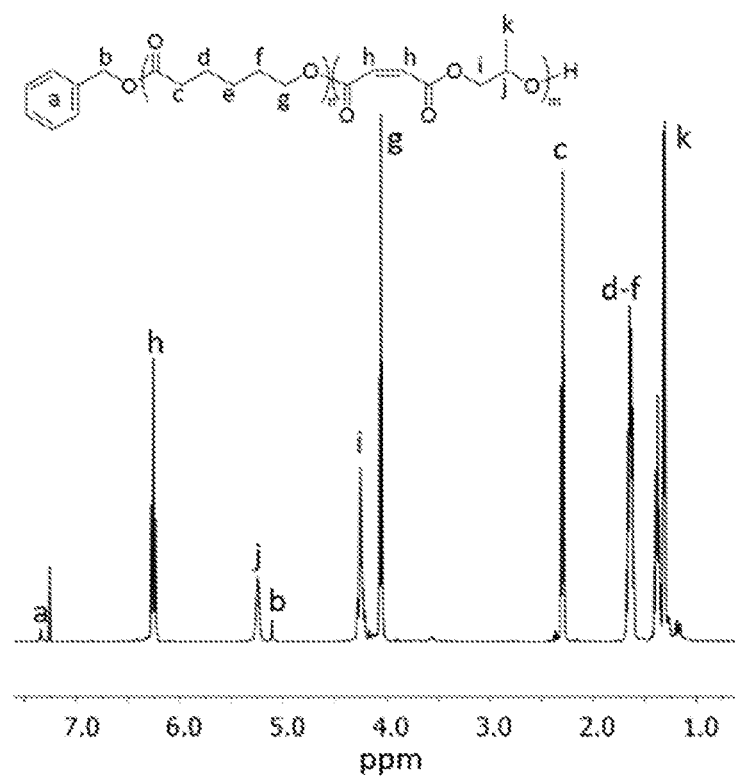
FIG. 2 is a $^1$H NMR spectrum of DP 100 poly(ε-caprolactone-b-propylene maleate) (500 MHz, CDCl$_3$, 303 K).
Figure 46:
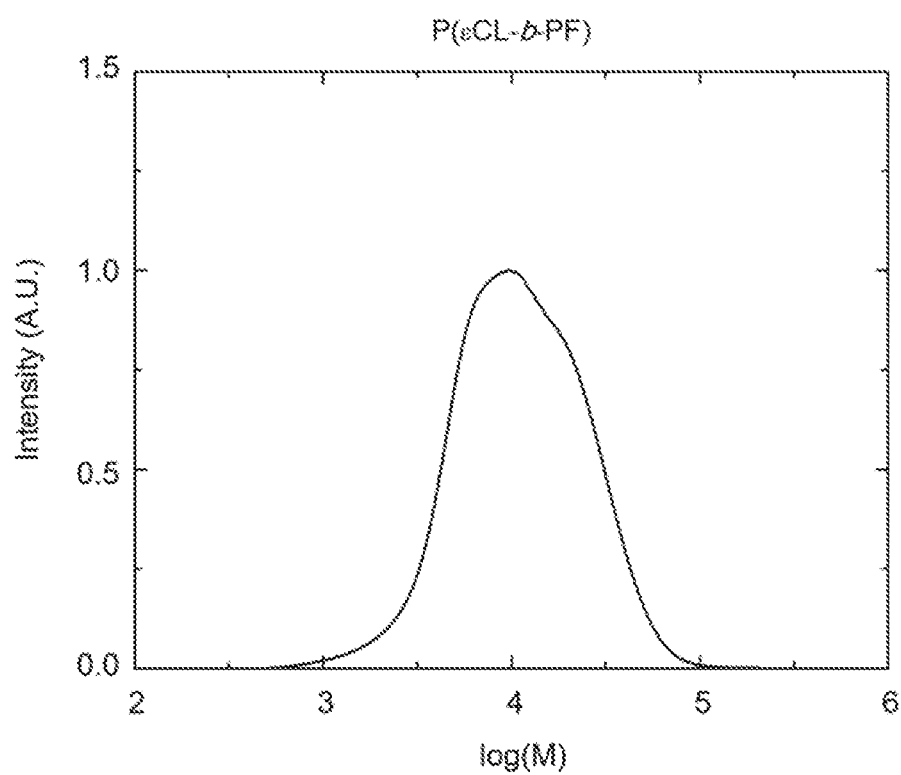
FIG. 46 is a SEC chromatogram for poly(ε-caprolactone-b-propylene maleate). The molecular mass determined against poly(styrene) standards.

The presence of a poly(ε-caprolactone-b-propylene maleate) product was confirmed by $^1$H NMR (300 MHz, 303 K, CDCl$_3$): δ=7.29 (m, Ar), 6.22 (m, OC(=O)H=CH(=O)O), 5.19 (m, CH$_2$CH(CH$_3$)O), 5.06 (s, C=OOCH$_2$Ar), 4.20 (m, CH$_2$OC=O), 2.25 (s, εCL CH$_2$C=OO), 1.26 (m, CH$_2$CH(CH$_3$)O), 1.60 and 1.33 (all remaining hydrogens) ppm (see, FIG. 2); $^{13}$C NMR (125 MHz, 303K, CDCl$_3$): δ=173.35 (εCL*-εCL, OCOCH$_2$), 173.11 (εCL*-PO, OCOCH$_2$), 164.97 (MAn*-εCL, OCOCH$_2$), 164.57 (MAn*-PO, OCOCH$_2$), 164.29 (MAn*-εCL, OCOCH$_2$), 130.33 and 129.72 (MAn*-PO, O(O)C*CH=CH), 129.86 and 129.20 (MAn*-PO, O(O)C*CH=CH), 128.42 and 128.03 (εCL-MAn*, O(O)CCH=CH), 69.03 (MAn*-PO, OCH(CH$_3$)CH$_2$), 66.29 (MAn*-PO, OCH(CH$_3$)CH$_2$), 65.98 (MAn*-εCL, OCH$_2$), 63.99 (εCL*-εCL, OCH$_2$), 33.99 (εCL*-εCL, OCOCH$_2$), 28.23 (εCL, OCH$_2$CH$_2$), 25.41 (εCL, OCOCH$_2$CH$_2$), 24.46 (εCL, OCOCH$_2$CH$_2$CH$_2$) and 16.10 (PO, CH$_2$CH(CH$_3$)O) ppm (see, FIG. 3); and SEC (DMF): M$_n$=12.5 kDa, M$_w$=15.5 kDa, Đ$_M$=1.24 (see, FIG. 46).

Example 8

Synthesis of Poly(ε-Caprolactone-b-Propylene Maleate)

Using standard Schlenk line techniques, an ampoule was filled with Mg(BHT)$_2$(THF)$_2$ (586.8 mg, 0.97 mmol), benzyl alcohol (0.1 mL, 0.97 mmol) and ε-caprolactone (5.35 mL, 48.3 mmol). The reagents were dissolved into toluene to a total monomer concentration of 2 M. The ampoule was sealed and heated at 80° C. for 24 h. A 2 M solution of propylene oxide (3.38 mL, 48.3 mmol) and maleic anhydride (4.74 g, 48.3 mmol) in toluene was added to the polymerization via cannula and heating continued at 80° C. for a further 120 h. The resultant polymer was recovered by precipitation in excess diethyl ether.

Example 9

Synthesis of Poly(ε-Heptalactone-b-Propylene Maleate)

Poly(ε-heptalactone-b-propylene maleate) was synthesized using the method set forth in Example 4 using ε-heptalactone as shown in Scheme 14, below and the using reaction parameters shown in Table 5, below.

Scheme 14
Sequential polymerization of ε-heptalactone followed by the copolymerization of maleic anhydride and propylene oxide.

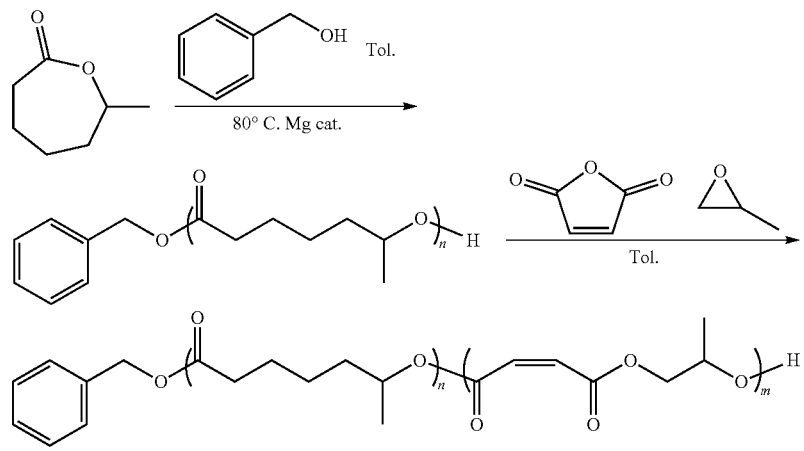

TABLE 5

| Initiator | mol. eq. εHL | mol. eq. PO | mol. eq. MA | T (° C.) | Time 1 (h) | Time 2 (h) | M$_{n, NMR}$ (kDa) | M$_{n, GPC}$ (kDa) | Đ$_M$ |
|---|---|---|---|---|---|---|---|---|---|
| BnOH | 50 | 50 | 50 | 80 | 24 | 120 | 9.6 | 13.5 | 1.27 |

Figure 36:
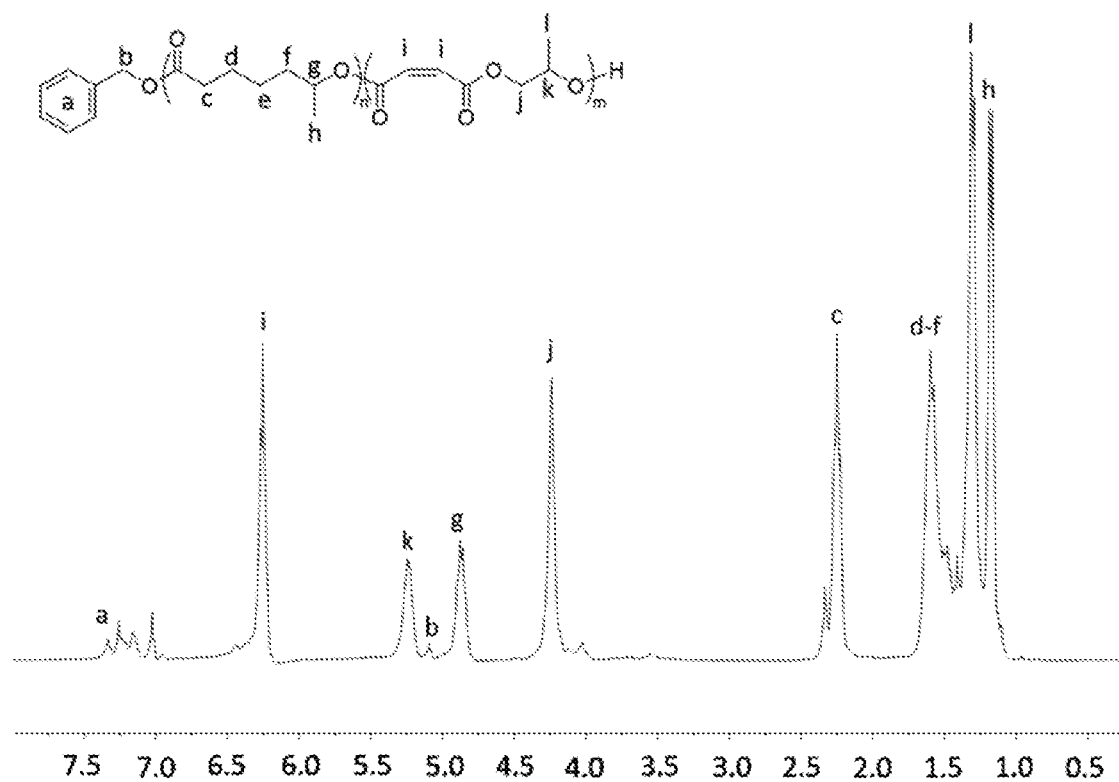
FIG. 36 is a ¹H NMR spectra of poly(ε-heptalactone-b-propylene maleate) (300 MHz, CDCl₃, 303 K).
Figure 37:
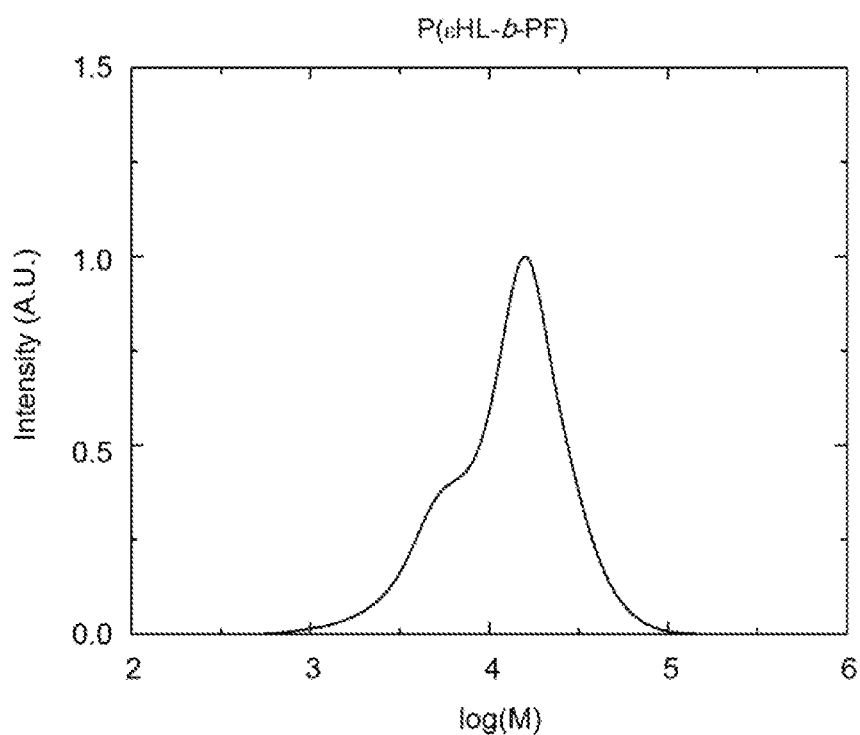
FIG. 37 is a SEC chromatogram for poly(ε-heptalactone-b-propylene maleate). The molecular mass was determined against poly(styrene) standards.

The presence of a poly(ε-heptalactone-b-propylene maleate) product was confirmed by $^1$H NMR (300 MHz, 303 K, CDCl$_3$): δ=7.32 (m, Ar), 6.23 (m, OC(=O)H=CH(=O)O), 5.22 (m, CH$_2$CH(CH$_3$)O), 5.07 (s, C=OOCH$_2$Ar), 4.85 (m, εHL CH$_2$OC=O), 4.23 (m, PO CH$_2$OC=O), 2.23 (s, CH$_2$C=OO), 1.16 (m, εHL CH$_3$), 1.63-1.22 (all remaining hydrogens) ppm (see, FIG. 36); $^{13}$C NMR (125 MHz, 303K, CDCl$_3$): δ=173.13 (εHL*-εHL, OCOCH$_2$), 164.83 (MAn*-εHL, OCOCH$_2$), 164.66 and 164.39 (MAn*-PO, OCOCH$_2$), 130.43 and 129.94 (MAn*-PO, O(O)C*CH=CH), 129.80 and 129.20 (MAn*-PO, O(O)C*CH=CH), 125.46 (εDL-MAn*, O( )CCH=CH), 77.36, 70.56 (εHL*-εHL, OCH$_2$), 69.13 (MAn*-PO, OCH(CH$_3$)CH$_2$), 66.39 (MAn*-PO, OCH(CH$_3$)CH$_2$), 35.54 (εHL*-εHL, CH$_2$CH$_2$COO), 34.47 (εHL, CH$_2$CH$_2$CH(CH$_3$)), 16.20 (PO, CH$_2$CH(CH$_3$)O), 19.92 (εHL, CH$_3$CH(CH$_2$)$_2$), 30.32 and 24.87 (all remaining carbons) ppm (see, FIG. 9); and SEC (DMF): M$_n$=13.5 kDa, M$_w$=17.1 kDa, Đ$_M$=1.27. A DOSY NMR spectrum of poly (ε-heptalactone-b-propylene maleate) (500 MHz, 303 K, CDCl$_3$) is attached as FIG. 37.

Example 10

Synthesis of Poly(ε-Decalactone-b-Propylene Maleate)

Poly(ε-decalactone-b-propylene maleate) was synthesized using the method set forth in Example 4 using ε-decalactone as shown in Scheme 15, below and the using reaction parameters shown in Table 6, below.

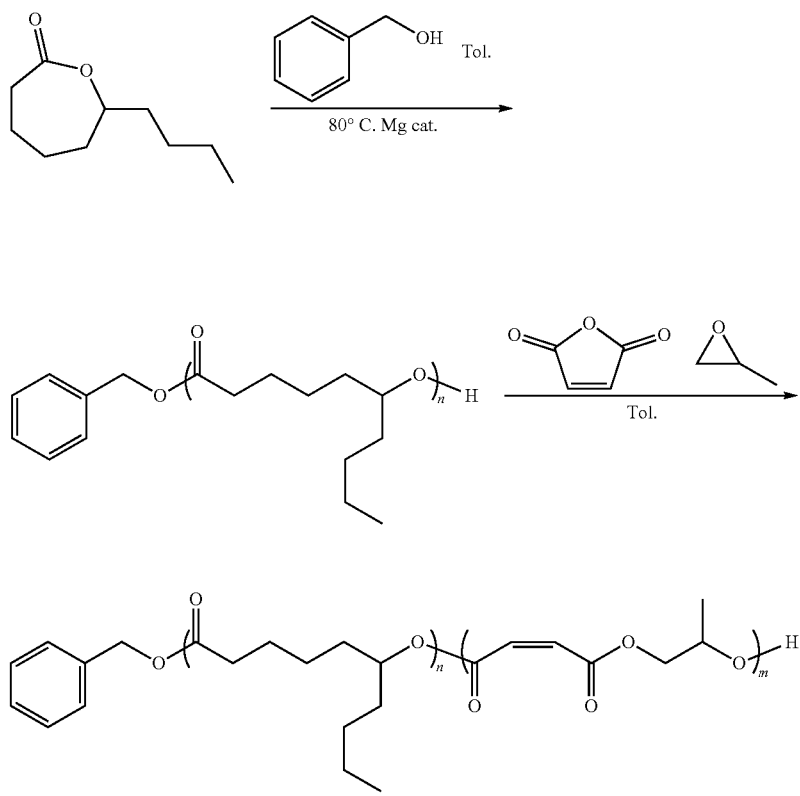

Scheme 15
Sequential polymerization of ε-decalactone followed by the copolymerization of maleic anhydride and propylene oxide.

TABLE 6

| Initiator | mol. eq. εDL | mol. eq. PO | mol. eq. MA | T (° C.) | Time 1 (h) | Time 2 (h) | $M_{n, NMR}$ (kDa) | $M_{n, GPC}$ (kDa) | $Đ_M$ |
|---|---|---|---|---|---|---|---|---|---|
| BnOH | 50 | 50 | 50 | 80 | 24 | 120 | 10.7 | 10.8 | 2.10 |

Figure 40:
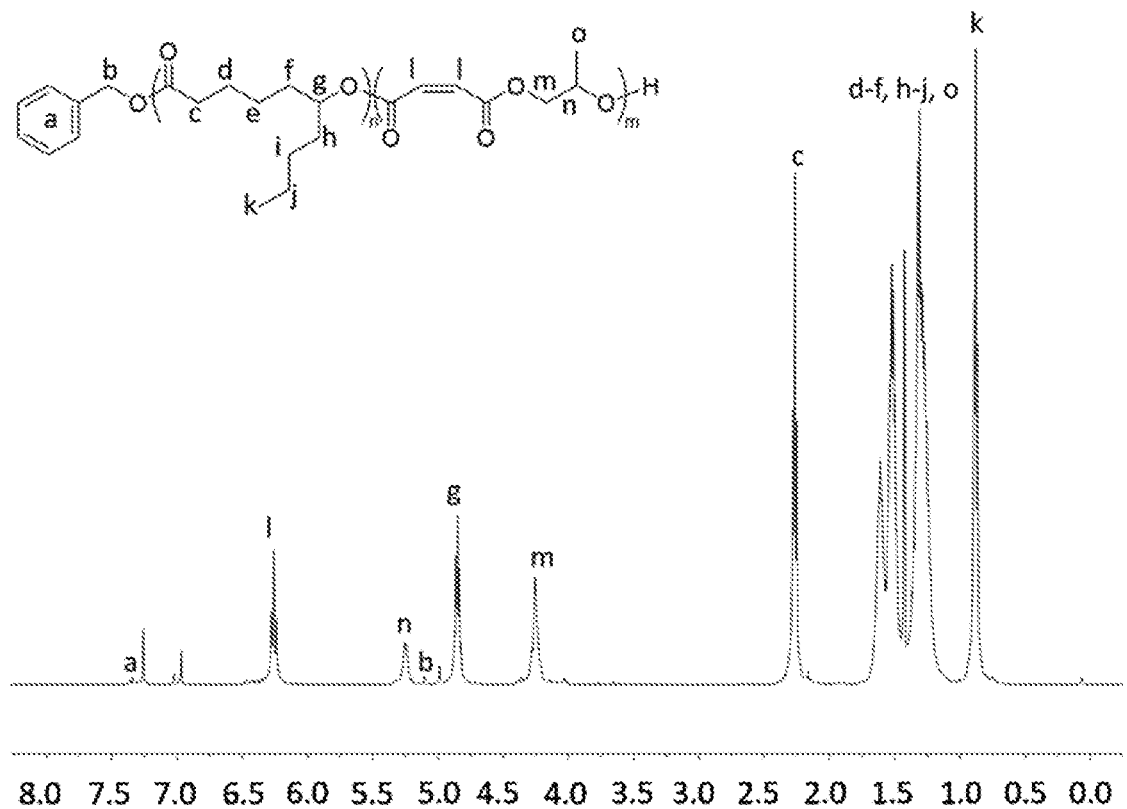
FIG. 40 is a ¹H NMR spectra of poly(ε-decalactone-b-propylene maleate) (300 MHz, CDCl₃, 303 K).
Figure 41:
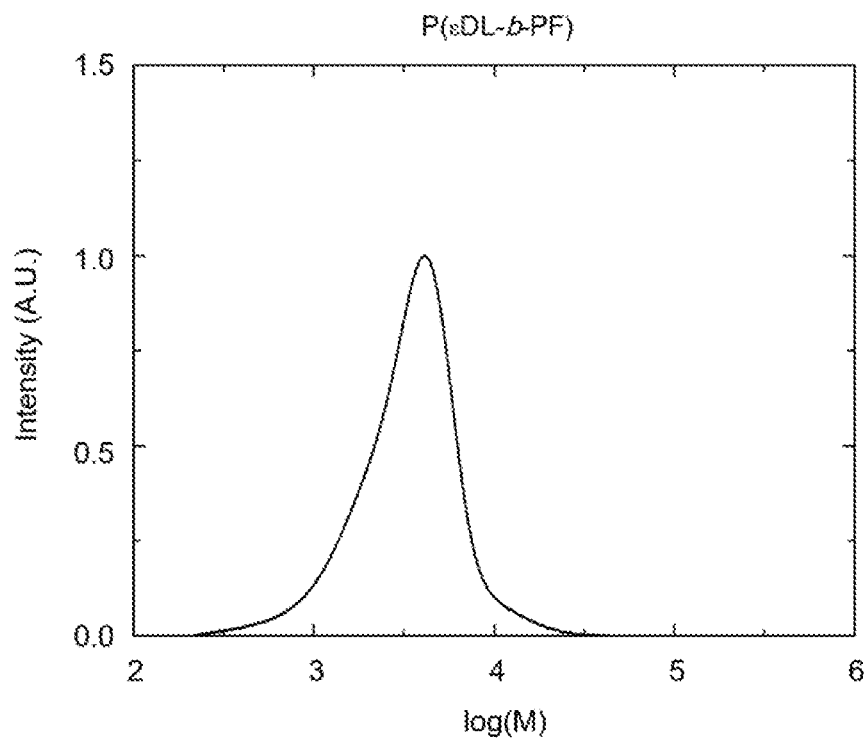
FIG. 41 is a SEC chromatogram for poly(ε-decalactone-b-propylene maleate). The molecular mass determined against poly(styrene) standards.

The presence of a Poly(ε-decalactone-b-propylene maleate) product was confirmed by $^1$H NMR (300 MHz, 303 K, CDCl$_3$): δ=7.33 (m, Ar), 6.25 (m, OC(=O)H=CH(=O) O), 5.25 (m, CH$_2$CH(CH$_3$)O), 5.09 (s, C=OOCH$_2$Ar), 4.84 (m, εDL CH$_2$OC=O), 4.24 (m, PO CH$_2$OC=O), 2.26 (s, CH$_2$C=OO), 0.87 (m, εDL CH$_3$(CH$_2$)$_3$), 1.65-1.20 (all remaining hydrogens) ppm (see, FIG. 40); $^{13}$C NMR (125 MHz, 303K, CDCl$_3$): δ=173.41 (εDL*-εDL, OCOCH$_2$), 164.81 (MAn*-εDL, OCOCH$_2$), 164.53 (MAn*-PO, OCOCH$_2$), 130.59 and 130.11 (MAn*-PO, O(O) C*CH=CH), 129.96 and 129.47 (MAn*-PO, O(O) C*CH=CH), 125.65 (εDL-MAn*, O( )CCH=CH), 74.04 (εDL*-εDL, OCH$_2$), 69.30 (MAn*-PO, OCH(CH$_3$)CH$_2$), 66.58 (MAn*-PO, OCH(CH$_3$)CH$_2$), 34.64 (εDL*-εDL, OCOCH$_2$), 33.93 (εDL, CH$_2$CH$_2$CH(Bu)), 16.37 (PO, CH$_2$CH(CH$_3$)O), 14.12 (εDL, CH$_3$(CH$_2$)$_3$), 30.48, 27.60, 25.13 and 22.71 (all remaining carbons) ppm (see, FIG. 15); and SEC (DMF): $M_n$=10.8 kDa, $M_w$=22.3 kDa, $Đ_M$=2.10 (see, FIG. 41). A DOSY NMR spectrum of poly(ε-decalactone-b-propylene maleate) (500 MHz, 303 K, CDCl$_3$) is attached as FIG. 16.

Example 11

General Procedure for the Isomerization of Poly(Lactone-b-Propylene Maleate)

Poly(ε-caprolactone)-b-(propylene maleate) (1.0 g, 12 mol. eq. olefin) was dissolved into chloroform (50 mL) and diethylamine (0.01 mL, 0.15 mol. eq. olefin) was added. The solution was refluxed for 24 h under a nitrogen atmosphere. After cooling to room temperature, the organic solution was washed with a 0.5 M phosphate buffer solution (150 mL, pH=6) prior to removal of solvent via rotary evaporation.

In light of the foregoing, it should be appreciated that the present invention significantly advances the art by providing a poly(lactone-b-propylene fumarate) block copolymer that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A diblock copolymer comprising a poly(lactone) segment having a first end comprising an end group comprising the residue of an initiating alcohol and a second end comprising a terminal hydroxyl group, and a poly(propylene fumarate) segment connected to the second end of said poly(lactone) segment and formed by ring-opening copolymerization of propylene oxide and maleic anhydride initiated by said terminal hydroxyl group on said poly(lactone) segment, followed by isomerization, said diblock copolymer having a polydispersity index (Đm) of from about 1.1 to about 1.9.

2. The diblock copolymer of claim 1 wherein said poly (lactone) segment comprises the residue of a lactone selected from the group consisting of δ-valerolactone, ε-caprolactone, α-chloro-ε-caprolactone, 4-chloro-ε-caprolactone, 4-methyl-7-isopropyl-ε-caprolactone (menthide), 2,5-oxepanedione (OPD), 7-methyl-4-(1-methylethenyl)-2-oxepanone (dihydrocarvide), 7-(prop-2-ynyl) oxepan-2-one, alkyl-substituted lactones, γ-methyl-ε-caprolactone, ε-heptalactone, ε-decalactone macrolactones, ω-pentadecalactone (PDL), functional lactones, θ-propargyl-ε-nonalactone (θpεNL), α-propargyl-ε-caprolactone (αpεCL), and combinations thereof.

3. The diblock copolymer of claim 1 wherein said residue of an initiating alcohol further comprises a functional end group selected from the group consisting of benzyl groups, alkyne groups, propargyl groups, allyl groups, alkene groups, 4-dibenzocyclooctyne groups, cyclooctyne groups, ketone groups, aldehyde groups, tertiary halogen groups and poly(ethylene glycol) groups, and combinations thereof to form an end-functionalized block co-polymer.

4. The diblock copolymer of claim 1 wherein said poly (propylene fumarate) segment comprises from about 0.1 mole percent to about 99 mole percent of said end functionalized block co-polymer.

5. The diblock copolymer of claim 1 wherein said poly (lactone) segment comprises from about 0.1 mole percent to about 99 mole percent of said end functionalized block co-polymer.

6. The copolymer of claim 1 having a number average molecular weight ($M_n$) of from about 0.5 kDa to about 500 kDa.

7. The diblock copolymer of claim 1 having the formula:

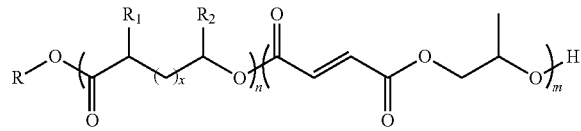

wherein n is an integer from about 1 to about 1000; m is an integer from about 1 to about 1000;

x is an integer from about 1 to about 20; R is an end functional group selected from the group consisting of benzyl groups, alkyne groups, propargyl groups, allyl groups, alkene groups, 4-dibenzocyclooctyne groups, cyclooctyne groups, ketone groups, aldehyde groups, tertiary halogen groups, poly(ethylene glycol) groups, and combinations thereof; $R_1$ is a hydrogen atom, a propargyl group, or a $C_1$-$C_{10}$ alkyl group; and $R_2$ is a hydrogen atom, a methyl group, a butyl group, a propargyl group or a $C_1$-$C_{10}$ alkyl group.

8. The diblock copolymer of claim 1 having the formula:

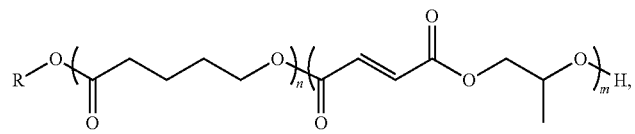

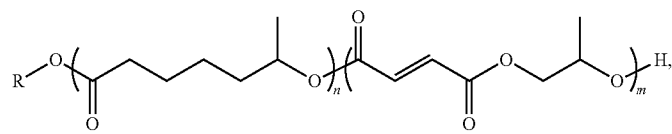

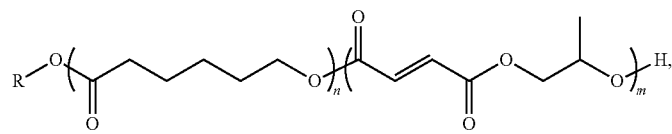

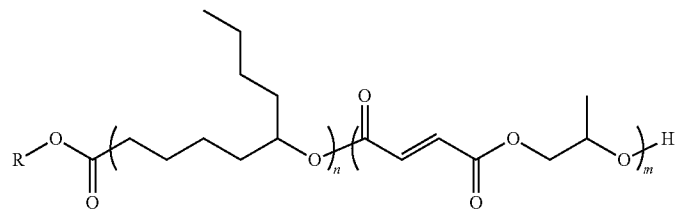

-continued

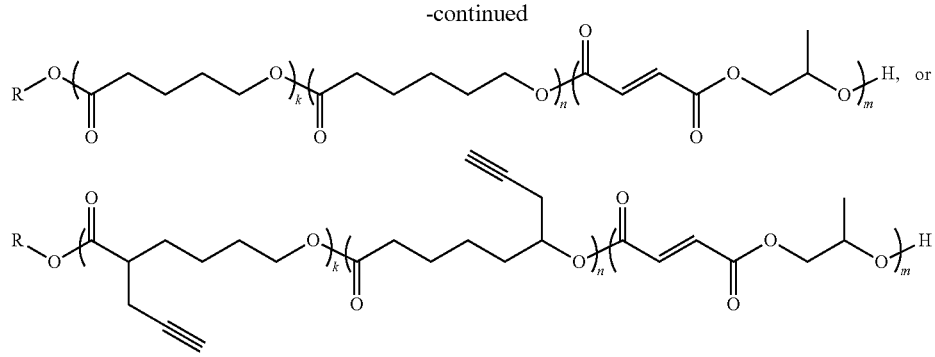

where n is an integer from about 1 to about 500; and m is an integer from about 1 to about 500;

k is an integer from about 1 to about 500 and R is an end functional group.

9. A method for making the diblock copolymer as claimed in claim 1 comprising:
A. preparing an initiating alcohol;
B. combining said initiating alcohol, $Mg(BHT)_2(THF)_2$ catalyst, and a lactone in a suitable reaction vessel;
C. dissolving the contents of said reaction vessel with a suitable solvent;
D. sealing and then heating the solution of Step C to cause or maintain the ring opening polymerization of said lactone, initiated by said initiating alcohol, thereby forming a poly(lactone) polymer having a first end comprising the residue of said initiating alcohol and a second end comprising a hydroxyl group;
E. dissolving maleic anhydride and propylene oxide in a suitable solvent and adding them to said reaction vessel;
F. heating the solution of Step E to initiate ring opening polymerization of said maleic anhydride and propylene oxide at said hydroxyl group to form a diblock copolymer intermediate comprising poly(lactone) segments and poly(propylene maleate) segments connected to the second end of said poly(lactone) segment; and
G. isomerizing said poly(propylene maleate) intermediate to form the poly(lactone-b-propylene fumarate) diblock copolymer.

10. The method of claim 9 wherein said initiating alcohol is selected from the group consisting of benzyl alcohol, propargyl alcohol, allyl alcohol, 4-dibenzylcyclooctanol, 4-hydroxybutan-2-one, 3-hydroxypropan-2-one, 5-hydroxypentan-2-one, 6-hydroxyhexan-2-one, 7-hydroxyheptan-2-one, 8-hydroxyoctan-2-one, 5-norbornen-2-ol, PEG diol, α-bromoisobutyryl 4-methanol benzylmethanoate, and combinations thereof.

11. The method of claim 9 wherein the initiating alcohol of Step A is end functionalized, the poly(lactone) polymer formed in step D is an end functionalized lactone polymer, the diblock copolymer intermediate comprising poly(lactone) segments and poly(propylene maleate) segments of step F is end functionalized, and the poly(lactone-b-propylene fumarate) polymer produced in Step G is an end functionalized poly(lactone-b-propylene fumarate) diblock copolymer.

12. The method of claim 11 wherein said end functionalized poly(lactone-b-propylene fumarate) diblock copolymer comprises an end functional group selected from the group consisting of benzyl groups, alkyne groups, propargyl groups, allyl groups, alkene groups, 4-dibenzocyclooctyne groups, cyclooctyne groups, ketone groups, aldehyde groups, tertiary halogen groups and poly(ethylene glycol) groups and combinations thereof.

13. The method of claim 9 wherein said lactone is selected from the group consisting of δ-valerolactone, ε-caprolactone, α-chloro-ε-caprolactone, 4-chloro-ε-caprolactone, 4-methyl-7-isopropyl-ε-caprolactone (menthide), 2,5-oxepanedione (OPD), 7-methyl-4-(1-methylethenyl)-2-oxepanone (dihydrocarvide), 7-(prop-2-ynyl) oxepan-2-one, alkyl-substituted lactones, γ-methyl-ε-caprolactone, ε-heptalactone, ε-decalactone macrolactones, ω-pentadecalactone (PDL), functional lactones, θ-propargyl-ε-nonalactone (θpεNL), α-propargyl-ε-caprolactone (αpεCL), and combinations thereof.

14. The method of claim 9 wherein the concentration of said lactone in the solution of Step C is from about 0.5 M to about 10 M.

15. The method of claim 9 wherein the total concentration of said maleic anhydride and said propylene oxide in the solution of Step E is from about 0.5 M to about 10 M.

16. The method of claim 9 wherein the solution of Step C is heated (Step D) to a temperature of from about 40° C. to about 100° C. and the solution of Step E is heated (Step F) to a temperature of from about 40° C. to about 100° C.

17. The method of claim 9 wherein the solution of Step C is heated (Step D) for from about 1 hour to about 96 hours and the solution of Step E is heated (Step F) for from about 1 hours to about 96 hours.

* * * * *